United States Patent
Peris et al.

(10) Patent No.: US 9,399,767 B2
(45) Date of Patent: *Jul. 26, 2016

(54) MUTANT RB69 DNA POLYMERASE

(71) Applicant: LIFE TECHNOLOGIES CORPORATION, Carlsbad, CA (US)

(72) Inventors: Marian Peris, Belmont, CA (US); Michael Phelan, Hayward, CA (US); Barnett Rosenblum, San Jose, CA (US); Stephen Hendricks, Los Gatos, CA (US)

(73) Assignee: LIFT TECHNOLOGIES CORPORATION, Carlsbad, CA (US)

( * ) Notice: Subject to any disclaimer, the term of this patent is extended or adjusted under 35 U.S.C. 154(b) by 38 days.

This patent is subject to a terminal disclaimer.

(21) Appl. No.: 14/191,997

(22) Filed: Feb. 27, 2014

(65) Prior Publication Data

US 2014/0234940 A1 Aug. 21, 2014

Related U.S. Application Data

(63) Continuation of application No. 13/600,416, filed on Aug. 31, 2012, now Pat. No. 8,703,461, which is a continuation of application No. 12/790,768, filed on May 28, 2010, now abandoned, application No. 14/191,997, which is a continuation of application No. 14/108,166, filed on Dec. 16, 2013, now Pat. No. 9,255,258, which is a continuation of application No. 12/790,760, filed on May 28, 2010, now Pat. No. 8,632,975.

(60) Provisional application No. 61/184,774, filed on Jun. 5, 2009, provisional application No. 61/242,762, filed on Sep. 15, 2009, provisional application No. 61/263,320, filed on Nov. 20, 2009, provisional application No. 61/295,533, filed on Jan. 15, 2010.

(51) Int. Cl.
*C12N 9/12* (2006.01)
*C12Q 1/68* (2006.01)

(52) U.S. Cl.
CPC ............ *C12N 9/1252* (2013.01); *C12Q 1/6804* (2013.01); *C12Q 1/6827* (2013.01); *C12Q 1/6869* (2013.01); *C12Q 1/6872* (2013.01); *G01N 2500/00* (2013.01)

(58) Field of Classification Search
None
See application file for complete search history.

(56) References Cited

U.S. PATENT DOCUMENTS

| | | | |
|---|---|---|---|
| 5,143,854 A | 9/1992 | Pirrung et al. |
| 5,151,507 A | 9/1992 | Hobbs et al. |
| 5,412,087 A | 5/1995 | McGall et al. |
| 5,558,991 A | 9/1996 | Trainor |
| 5,773,308 A | 6/1998 | Conrad et al. |
| 6,818,425 B2 | 11/2004 | Hjorleifsdottir et al. |
| 7,264,934 B2 | 9/2007 | Fuller |
| 7,270,951 B1 | 9/2007 | Stemple et al. |
| 7,279,563 B2 | 10/2007 | Kwiatkowski |
| 7,393,640 B2 | 7/2008 | Kumar et al. |
| 7,405,281 B2 | 7/2008 | Xu et al. |
| 7,416,844 B2 | 8/2008 | Korlach et al. |
| 7,427,673 B2 | 9/2008 | Balasubramanian et al. |
| 7,476,504 B2 | 1/2009 | Turner |
| 7,485,424 B2 | 2/2009 | Korlach et al. |
| 7,541,444 B2 | 6/2009 | Milton et al. |
| 2007/0196846 A1 | 8/2007 | Hanzel et al. |
| 2008/0009007 A1 | 1/2008 | Lyle et al. |
| 2008/0050780 A1 | 2/2008 | Lee et al. |
| 2008/0103053 A1 | 5/2008 | Siddiqi et al. |
| 2008/0108082 A1 | 5/2008 | Rank et al. |
| 2008/0132692 A1 | 6/2008 | Wu et al. |
| 2008/0227970 A1 | 9/2008 | Siddiqi et al. |
| 2008/0269476 A1 | 10/2008 | Siddiqi |
| 2008/0286837 A1 | 11/2008 | Siddiqi |
| 2008/0287305 A1 | 11/2008 | Fuller et al. |
| 2008/0293071 A1 | 11/2008 | Gelfand et al. |
| 2009/0061437 A1 | 3/2009 | Efcavitch et al. |
| 2009/0176233 A1 | 7/2009 | Clark et al. |
| 2010/0255487 A1 | 10/2010 | Beechem et al. |
| 2010/0311144 A1 | 12/2010 | Peris et al. |
| 2010/0330570 A1 | 12/2010 | Vander Horn et al. |

FOREIGN PATENT DOCUMENTS

| | | |
|---|---|---|
| WO | WO-91/06678 | 5/1991 |
| WO | WO-2007/048033 | 4/2007 |
| WO | WO-2010/141391 | 12/2010 |
| WO | WO-2010/141391 A3 | 4/2011 |

OTHER PUBLICATIONS

Bai, Xiaopeng et al., "Design and synthesis of a photocleavable biotinylated nucleotide for DNA analysis by mass spectrometry", *Nucleic Acids Research*, vol. 32, No. 2, 2004, 535-541.
Bakhtina, Marina et al., "Contribution of the Reverse Rate of the Conformational Step to Polymerase B Fidelity", *Biochem.*, vol. 48, 2009, 3197-3208.
Beese, Lorena et al., "Structural basis for the 3'-5' exonuclease activity of *Escherichia coli* DNA polymerase I: a two metal ion mechanism", *The EMBO Journal*, vol. 10 No. 1, 1991, 25-33.
Bentley, D. et al., "Accurate whole human genome sequencing using reversible terminator chemistry", *Nature*, vol. 456(6), (7218), 2008, pp. 53-59.
Berman, Andrea J. et al., "Structures of phi29 DNA polymerase complexed with substrate: the mechanism of translocation in B-family polymerases", *The EMBO Journal*, vol. 26, 2007, 3494-3505.

(Continued)

*Primary Examiner* — Richard Hutson

(57) ABSTRACT

Provided herein are mutant DNA-dependent polymerases which are derived from, or otherwise related to, wild type RB69 DNA polymerase. These mutant polymerases are capable of selectively binding labeled nucleotides. These mutant polymerases are also capable of incorporating a variety of naturally occurring and modified nucleotides, including, for example, terminator nucleotides.

9 Claims, 37 Drawing Sheets

(56) References Cited

OTHER PUBLICATIONS

Castro, Christian et al., "Nucleic acid polymerases use a general acid for nucleotidyl transfer", *Nature Structural & Molecular Biology*, vol. 16 No. 2, 2009, 212-218.

Dunaway-Mariano, Debra et al., "Investigations of Substrate Specificity and Reaction Mechanism of Several Kinases Using Chromium(III) Adenosine 5'-Triphosphate and Chromium(III) Adenosine 5'-Diphosphate", *Biochemistry*, 19, 1980, 1506-1515.

Dunaway-Mariano, Debra et al., "Preparation and Properties of Chromium(III) Adenosine 5'-Triphosphate, Chromium(III) Adenosine 5'-Diphosphate, and Related Chromium(III) Complexes", *Biochemistry*, 19, 1980, 1496-1505.

Flemer, Stevenson et al., "Strategies for the Solid-Phase Diversification of Poly-L-proline-Type II Peptide Minic Scaffolds and Peptide Scaffolds Through Guanidinylation", *J. Org. Chem.*, vol. 73, 2008, 7593-7602.

Gangurde, Rajiv et al., "Participation of Active-Site Carboxylates of *Escherichia coli* DNA Polymerase I (Klenow Fragment) in the Formation of a Prepolymerase Ternary Complex", *Biochemistry*, 41, 2002, 14552-14559.

Gao, Xiaohu et al., "In vivo cancer targeting and imaging with semiconductor quantum dots", *Nature Biotechnology*, vol. 22, No. 8, 2004, 969-976.

Gardner, Andrew et al., "Determinants of nucleotide sugar recognition in an archaeon DNA polymerase", *Nucl. Acids Res.*, 27(12), doi:10.1093/nar/27.12.2545, 1999, 2545-2553.

Gardner, Andrew F. et al., "Acyclic and dideoxy terminator preferences denote divergent sugar recognition by archaeon and Taq DNA polymerases", *Nucleic Acids Research*, vol. 30, No. 2, 2002, 605-613.

Guo, Jia et al., "Four-color DNA sequencing with 3'-O-modified nucleotide reversible terminators and chemically cleavable fluorescent dideoxynucleotides", *PNAS*, vol. 105, No. 27, Jul. 8, 2008, 9145-9150.

Jacewicz, Agata et al., "The Roles of Tyr391 and Tyr619 in RB69 DNA Polymerase Replication Fidelity", *Journal of Molecular Biology*. vol. 368, No. 1, 2007, pp. 18-29.

Johnson, K., "Rapid kinetic analysis of mechanochemical adenosinetriphosphatases", *Methods Enzymol.*, vol. 134, 1986, pp. 677-705.

Joyce, Catherine et al., "Fingers-Closing and Other Rapid Conformational Changes in DNA Polymerase I (Klenow Fragment) and Their role in Nucleotide Selectivity",*Biochemistry*, 47, 2008, 6103-6116.

Ju, J et al., "Four-color DNA sequencing by synthesis using cleavable fluorescent nucleotide reversible terminators", *PNAS*, vol. 103 (52), 2006, pp. 19635-19640.

Kaushik, Neerja et al., "Biochemical Analysis of Catalytically Crucial Aspartate Mutants of Human Immunodeficiency Virus Type 1 Reverse Transcriptase", *Biochemistry*, 35, 1996, 11536-11546.

Kumar, Amarendra et al., "Inhibition of T7 RNA Polymerase: Transcription Initiation and Transition from Initiation to Elongation Are Inhibited by T7 Lysozyme via a Ternary Complex with RNA Polymerase and Promoter DNA", *Biochemistry*, vol. 36, No. 45, 1997, pp. 13954-13962.

Lee, Harold et al., "The Reopening Rate of the Fingers Domain Is a Determinant of Base Selectivity for RB69 DNA Polymerase", *Biochemistry*, 48, 2009, 2087-2098.

Megiatto, Jackson D. et al., "General Method for Synthesis of Functionalized Macrocycles and Catenanes Utilizing "Click" Chemistry", *J. Am. Chem. Soc.*, vol. 130, 2008, 12872-12873.

Ngo, et al., "The Protein Folding Problem and Tertiary Structure Predict ion", Merz et al. (ed .), Birkhauser, Boston, MA, 1994, pp. 433 and 492-495.

Patel, et al., "Insights into DNA Polymerization Mechanisms from Structure and Function Analysis of HIV-1 Reverse Transcriptase", *Biochemistry*, vol. 34, No. 16, Apr. 1995, 5351-5363.

PCTUS201036760, International Search Report and Written Opinion Received mailed on Feb. 21, 2011, 12 pgs.

Pelletier, Huguette et al., "Structures of Ternary Complexes of Rat DNA Polymerase beta, a DNA Template-Primer, and ddCTP", *Science*, vol. 264, Jun. 24, 1994, 1891-1903.

Rienitz, Axel et al., "On the fidelity of DNA polymerase alpha: the influence of alpha-thio dNTPs, Mn2+ and mismatch repair",*Nucleic Acids Research*, vol. 13, No. 15, 1985, 5685-5695.

Roettger, Michelle P. et al., "Mismatched and Matched dNTP Incorporation by DNA Polymerase # Proceed via Analogous Kinetic Pathways", *Biochemistry*, vol. 47, No. 37, 2008, 9718-9727.

Ruparel, H. et al., "Design and synthesis of a 3'-a-allyl photocleavable fluorescent nucleotide as a reversible terminator for DNA sequencing by synthesis", vol. 102 (17), Apr. 1, 2005, 5932-5937.

Sanger, F. et al., "DNA sequencing with chain-terminating inhibitors", *Proc. Natl. Acad. Sci. USA*, vol. 74(12), 1977, 5463-5467.

Sawaya, Michael et al., "Crystal Structures of Human DNA Polymerase B Complexed with Gapped and Nicked DNA: Evidence for an induced Fit Mechanism", *Biochemistry*, 36, 1997, 11205-11215.

Seo, Tae Seok et al., "Four-color DNA sequencing by synthesis on a chip using photocleavable fluorescent nucleotides", *PNAS*, vol. 102, No. 17, 2005, 5926-5931.

Shimkus, M et al., "A chemically cleavable biotinylated nucleotide: Usefulness in the recovery of protein-DNA complexes from avidin affinity columns", *PNAS*, vol. 82, 1985, pp. 2593-2597.

Steitz, Thomas et al., "A general two-metal-ion mechanism for catalytic RNA", *Proc. Natl. Acad. Sci. USA*, vol. 90, 1993, 6498-6502.

Steitz, Thomas , "A mechanism for all polymerases", *Nature*, vol. 391, 1998, 231-232.

Trzemecka, Anna et al., "Different Behaviors In Vivo of Mutations in the B Hairpin Loop of the DNA Polymerases of the Closely Related Phages T4 and RB69", *Journal of Molecular Biology*. vol. 389, No. 5, 2009, pp. 797-807.

Tsai, Yu-Chih et al., "A New Paradigm for DNA Polymerase Specificity", *Biochemistry*, vol. 45, No. 32, 2006, 9675-9687.

Turcatti, Gerardo et al., "A new class of cleavable fluorescent nucleotides: synthesis and optimization as reversible terminators for DNA sequencing by synthesis", *Nucleic Acids Research*, vol. 36, No. 4, e25, 2008, 1-13.

Wang, Mina et al., "Effect of A and B Metal Ion Site Occupancy on Conformational Changes in an RB69 DNA Polymerase Ternary Complex", *Biochemistry*, 48, 2009, 2075-2086.

Werts, Michel P., "Mechanically Linked Polyrotaxanes: A Stepwise Approach", *Macromolecules*, vol. 36, Iss. 19, 2003, 7004-7013.

Wu, J et al., "3'-O-modified nucleotides as reversible terminators for pyrosequencing", *PNAS*, vol. 104 (42), 2007, pp. 16462-16467.

Wu, J et al., "Termination of DNA synthesis by N6-alkylated, not 3'-O-alkylated, photocleavable 2'-deoxyadenosine triphosphates", *Nuc Acids Research*, vol. 35(19), 2007, pp. 6339-6349.

Zhang, Hong et al., "The L561A Substitution in the Nascent Base-Pair Binding Pocket of RB69 DNA Polymerase Reduces Base Discrimination", *Biochemistry*. vol. 45, No. 7, 2006, pp. 2211-2220.

Zhong, Xuejun et al., "Characterization of a replicative DNA polymerase mutant with reduced fidelity and increased translesion synthesis capacity", *Nucleic Acids Research*. vol. 36, No. 12, 2008, pp. 3892-3904.

Zhong, Xuejun et al., "DNA Polymerase B. 5. Dissecting the Functional Roles of the Two Metal Ions with Cr(III)dTTP", *J. Am. Chem. Soc.*, 120, 1998, 235-236.

```
ATGAAAGAATTTTACTTAACGGTTGAACAGATTGGTGATTCAATTTTTGAACGTTACATC
 M  K  E  F  Y  L  T  V  E  Q  I  G  D  S  I  F  E  R  Y  I

GATTCTAATGGCCGTGAACGTACTCGTGAAGTAGAATATAAACCATCACTGTTTGCTCAT
 D  S  N  G  R  E  R  T  R  E  V  E  Y  K  P  S  L  F  A  H

TGTCCAGAAAGTCAGGCTACGAAATATTTCGATATCTACGGTAAACCGTGTACTCGTAAG
 C  P  E  S  Q  A  T  K  Y  F  D  I  Y  G  K  P  C  T  R  K

TTGTTCGCTAATATGCGTGATGCCTCCCAATGGATTAAACGCATGGAAGATATCGGACTT
 L  F  A  N  M  R  D  A  S  Q  W  I  K  R  M  E  D  I  G  L

GAAGCACTTGGCATGGACGATTTCAAATTGGCGTATTTGTCTGACACTTATAACTATGAA
 E  A  L  G  M  D  D  F  K  L  A  Y  L  S  D  T  Y  N  Y  E

ATCAAATACGACCATACAAAAATTCGTGTGGCTAACTTCGACATCGAAGTAACATCTCCG
 I  K  Y  D  H  T  K  I  R  V  A  N  F  D  I  E  V  T  S  P

GATGGGTTCCCTGAGCCGTCACAAGCAAAACATCCGATTGATGCTATCACCCATTATGAC
 D  G  F  P  E  P  S  Q  A  K  H  P  I  D  A  I  T  H  Y  D

TCAATTGACGACAGGTTCTACGTATTTGATCTATTGAATTCTCCATATGGTAATGTAGAA
 S  I  D  D  R  F  Y  V  F  D  L  L  N  S  P  Y  G  N  V  E

GAATGGTCTATTGAAATCGCTGCTAAGCTTCAAGAACAAGGTGGTGATGAAGTTCCATCT
 E  W  S  I  E  I  A  A  K  L  Q  E  Q  G  G  D  E  V  P  S

GAAATTATTGATAAAATCATTTATATGCCGTTCGATAACGAAAAGAATTGTTGATGGAA
 E  I  I  D  K  I  I  Y  M  P  F  D  N  E  K  E  L  L  M  E

TATCTCAACTTCTGGCAACAGAAAACTCCTGTCATTTTGACTGGATGGAACGTTGAGTCA
 Y  L  N  F  W  Q  Q  K  T  P  V  I  L  T  G  W  N  V  E  S

TTTGATATTCCGTACGTGTATAACCGAATCAAGAATATTTTTGGCGAATCAACTGCGAAA
 F  D  I  P  Y  V  Y  N  R  I  K  N  I  F  G  E  S  T  A  K

CGTTTATCACCACATCGTAAAACTCGTGTTAAAGTTATCGAAAACATGTATGGTTCTCGT
 R  L  S  P  H  R  K  T  R  V  K  V  I  E  N  M  Y  G  S  R

GAAATCATTACATTGTTCGGTATCTCTGTTCTTGATTACATTGACCTTTACAAAAAATTC
 E  I  I  T  L  F  G  I  S  V  L  D  Y  I  D  L  Y  K  K  F

TCTTTTACCAATCAACCGTCGTATTCTCTGGATTACATTTCAGAATTTGAATTGAACGTT
 S  F  T  N  Q  P  S  Y  S  L  D  Y  I  S  E  F  E  L  N  V
```

FIG. 1A

```
GGTAAACTGAAATATGACGGCCCTATTTCTAAGCTTCGTGAAAGCAATCACCAACGATAT
 G   K   L   K   Y   D   G   P   I   S   K   L   R   E   S   N   H   Q   R   Y

ATTTCTTATAACATTATCGACGTGTATCGTGTATTGCAAATTGATGCTAAGCGTCAGTTC
 I   S   Y   N   I   I   D   V   Y   R   V   L   Q   I   D   A   K   R   Q   F

ATCAACTTGAGTTTGGACATGGGTTATTATGCTAAGATACAGATTCAATCTGTGTTTAGC
 I   N   L   S   L   D   M   G   Y   Y   A   K   I   Q   I   Q   S   V   F   S

CCAATTAAAACATGGGATGCTATTATTTTTAATAGCCTTAAAGAGCAGAACAAGGTGATT
 P   I   K   T   W   D   A   I   I   F   N   S   L   K   E   Q   N   K   V   I

CCACAAGGTCGTTCTCACCCGGTTCAACCTTATCCCGGCGCTTTTGTTAAGGAACCTATT
 P   Q   G   R   S   H   P   V   Q   P   Y   P   G   A   F   V   K   E   P   I

CCAAATCGATACAAATATGTAATGAGTTTCGACCTTACATCTCTATATCCAAGTATTATT
 P   N   R   Y   K   Y   V   M   S   F   D   L   T   S   L   Y   P   S   I   I

CGCCAAGTGAATATTAGCCCAGAAACAATAGCAGGAACGTTTAAAGTAGCTCCATTGCAT
 R   Q   V   N   I   S   P   E   T   I   A   G   T   F   K   V   A   P   L   H

GATTATATTAACGCTGTTGCTGAACGTCCTTCTGATGTGTACAGTTGTTCTCCTAACGGC
 D   Y   I   N   A   V   A   E   R   P   S   D   V   Y   S   C   S   P   N   G

ATGATGTATTATAAAGACCGTGATGGTGTAGTTCCAACTGAAATCACTAAGGTCTTTAAT
 M   M   Y   Y   K   D   R   D   G   V   V   P   T   E   I   T   K   V   F   N

CAACGTAAAGAACATAAAGGTTACATGCTTGCAGCTCAACGTAATGGTGAAATAATTAAA
 Q   R   K   E   H   K   G   Y   M   L   A   A   Q   R   N   G   E   I   I   K

GAGGCATTGCATAATCCTAATCTTTCTGTTGACGAACCATTAGATGTTGATTATCGTTTC
 E   A   L   H   N   P   N   L   S   V   D   E   P   L   D   V   D   Y   R   F

GACTTCAGCGATGAGATTAAAGAAAAGATTAAAAAGTTGTCTGCTAAATCTCTTAATGAA
 D   F   S   D   E   I   K   E   K   I   K   K   L   S   A   K   S   L   N   E

ATGTTGTTTAGAGCTCAACGTACTGAAGTTGCAGGTATGACTGCACAAATTAACCGTAAA
 M   L   F   R   A   Q   R   T   E   V   A   G   M   T   A   Q   I   N   R   K

TTGCTTATCAACTCACTTTATGGTGCACTTGGCAACGTTTGGTTCCGTTATTATGATTTG
 L   L   I   N   S   L   Y   G   A   L   G   N   V   W   F   R   Y   Y   D   L

CGTAATGCTACTGCAATCACAACATTCGGGCAAATGGCTTTACAGTGGATTGAACGTAAA
 R   N   A   T   A   I   T   T   F   G   Q   M   A   L   Q   W   I   E   R   K
```

FIG. 1B

```
GTTAATGAATATCTGAATGAAGTTTGTGGTACAGAAGGTGAAGCTTTCGTTCTTTATGGT
 V  N  E  Y  L  N  E  V  C  G  T  E  G  E  A  F  V  L  Y  G

GATACAGACTCTATTTACGTATCTGCTGATAAAATTATCGATAAGGTTGGTGAATCTAAA
 D  T  D  S  I  Y  V  S  A  D  K  I  I  D  K  V  G  E  S  K

TTCCGTGATACCAACCATTGGGTAGACTTCTTAGATAAGTTTGCACGTGAACGTATGGAA
 F  R  D  T  N  H  W  V  D  F  L  D  K  F  A  R  E  R  M  E

CCAGCTATTGATAGAGGTTTCCGTGAAATGTGTGAATACATGAACAATAAACAACACTTA
 P  A  I  D  R  G  F  R  E  M  C  E  Y  M  N  N  K  Q  H  L

ATGTTCATGGACCGAGAAGCTATCGCTGGGCCTCCGCTTGGTTCTAAAGGTATTGGCGGA
 M  F  M  D  R  E  A  I  A  G  P  P  L  G  S  K  G  I  G  G

TTTTGGACTGGTAAGAAACGTTATGCATTAAACGTGTGGGATATGGAAGGTACTCGTTAC
 F  W  T  G  K  K  R  Y  A  L  N  V  W  D  M  E  G  T  R  Y

GCTGAGCCTAAACTCAAAATCATGGGTCTAGAGACTCAGAAATCTTCGACTCCTAAAGCA
 A  E  P  K  L  K  I  M  G  L  E  T  Q  K  S  S  T  P  K  A

GTACAGAAAGCTCTTAAAGAATGTATTCGTCGTATGCTTCAAGAAGGTGAAGAATCATTA
 V  Q  K  A  L  K  E  C  I  R  R  M  L  Q  E  G  E  E  S  L

CAAGAATATTTTAAAGAGTTTGAAAAAGAATTCCGTCAATTGAATTATATTAGCATCGCG
 Q  E  Y  F  K  E  F  E  K  E  F  R  Q  L  N  Y  I  S  I  A

TCGGTATCTTCTGCGAATAACATTGCTAAATATGACGTAGGTGGATTCCCTGGTCCCAAA
 S  V  S  S  A  N  N  I  A  K  Y  D  V  G  G  F  P  G  P  K

TGCCCGTTCCATATTCGTGGAATTCTGACATATAACCGAGCTATCAAAGGTAATATTGAT
 C  P  F  H  I  R  G  I  L  T  Y  N  R  A  I  K  G  N  I  D

GCACCACAAGTTGTAGAAGGTGAAAAAGTATATGTTCTGCCTTTACGTGAAGGAAACCCA
 A  P  Q  V  V  E  G  E  K  V  Y  V  L  P  L  R  E  G  N  P

TTCGGTGATAAATGTATCGCATGGCCTTCTGGTACTGAAATCACAGATTTAATTAAAGAC
 F  G  D  K  C  I  A  W  P  S  G  T  E  I  T  D  L  I  K  D

GACGTACTTCATTGGATGGACTACACTGTTCTCCTTGAGAAGACATTTATTAAACCACTT
 D  V  L  H  W  M  D  Y  T  V  L  L  E  K  T  F  I  K  P  L

GAAGGATTCACATCAGCAGCGAAACTCGATTACGAGAAGAAAGCATCTCTGTTCGATATG
 E  G  F  T  S  A  A  K  L  D  Y  E  K  K  A  S  L  F  D  M

TTCGATTTT
 F  D  F
```

FIG. 1C

```
ATGAAAGAATTTTACTTAACGGTTGAACAGATTGGTGATTCAATTTTTGAACGTTACATC
 M  K  E  F  Y  L  T  V  E  Q  I  G  D  S  I  F  E  R  Y  I

GATTCTAATGGCCGTGAACGTACTCGTGAAGTAGAATATAAACCATCACTGTTTGCTCAT
 D  S  N  G  R  E  R  T  R  E  V  E  Y  K  P  S  L  F  A  H

TGTCCAGAAAGTCAGGCTACGAAATATTTCGATATCTACGGTAAACCGTGTACTCGTAAG
 C  P  E  S  Q  A  T  K  Y  F  D  I  Y  G  K  P  C  T  R  K

TTGTTCGCTAATATGCGTGATGCCTCCCAATGGATTAAACGCATGGAAGATATCGGACTT
 L  F  A  N  M  R  D  A  S  Q  W  I  K  R  M  E  D  I  G  L

GAAGCACTTGGCATGGACGATTTCAAATTGGCGTATTTGTCTGACACTTATAACTATGAA
 E  A  L  G  M  D  D  F  K  L  A  Y  L  S  D  T  Y  N  Y  E

ATCAAATACGACCATACAAAAATTCGTGTGGCTAACTTCGACATCGAAGTAACATCTCCG
 I  K  Y  D  H  T  K  I  R  V  A  N  F  D  I  E  V  T  S  P

GATGGGTTCCCTGAGCCGTCACAAGCAAAACATCCGATTGATGCTATCACCCATTATGAC
 D  G  F  P  E  P  S  Q  A  K  H  P  I  D  A  I  T  H  Y  D

TCAATTGACGACAGGTTCTACGTATTTGATCTATTGAATTCTCCATATGGTAATGTAGAA
 S  I  D  D  R  F  Y  V  F  D  L  L  N  S  P  Y  G  N  V  E

GAATGGTCTATTGAAATCGCTGCTAAGCTTCAAGAACAAGGTGGTGATGAAGTTCCATCT
 E  W  S  I  E  I  A  A  K  L  Q  E  Q  G  G  D  E  V  P  S

GAAATTATTGATAAAATCATTTATATGCCGTTCGATAACGAAAAGAATTGTTGATGGAA
 E  I  I  D  K  I  I  Y  M  P  F  D  N  E  K  E  L  L  M  E

TATCTCAACTTCTGGCAACAGAAAACTCCTGTCATTTTGACTGGATGGAACGTTGAGTCA
 Y  L  N  F  W  Q  Q  K  T  P  V  I  L  T  G  W  N  V  E  S

TTTGCTATTCCGTACGTGTATAACCGAATCAAGAATATTTTTGGCGAATCAACTGCGAAA
 F  A  I  P  Y  V  Y  N  R  I  K  N  I  F  G  E  S  T  A  K

CGTTTATCACCACATCGTAAAACTCGTGTTAAAGTTATCGAAAACATGTATGGTTCTCGT
 R  L  S  P  H  R  K  T  R  V  K  V  I  E  N  M  Y  G  S  R

GAAATCATTACATTGTTCGGTATCTCTGTTCTTGATTACATTGACCTTTACAAAAAATTC
 E  I  I  T  L  F  G  I  S  V  L  D  Y  I  D  L  Y  K  K  F

TCTTTTACCAATCAACCGTCGTATTCTCTGGATTACATTTCAGAATTTGAATTGAACGTT
 S  F  T  N  Q  P  S  Y  S  L  D  Y  I  S  E  F  E  L  N  V
```

FIG. 2A

```
GGTAAACTGAAATATGACGGCCCTATTTCTAAGCTTCGTGAAAGCAATCACCAACGATAT
 G   K   L   K   Y   D   G   P   I   S   K   L   R   E   S   N   H   Q   R   Y

ATTTCTTATAACATTATCGCTGTGTATCGTGTATTGCAAATTGATGCTAAGCGTCAGTTC
 I   S   Y   N   I   I   A   V   Y   R   V   L   Q   I   D   A   K   R   Q   F

ATCAACTTGAGTTTGGACATGGGTTATTATGCTAAGATACAGATTCAATCTGTGTTTAGC
 I   N   L   S   L   D   M   G   Y   Y   A   K   I   Q   I   Q   S   V   F   S

CCAATTAAAACATGGGATGCTATTATTTTTAATAGCCTTAAAGAGCAGAACAAGGTGATT
 P   I   K   T   W   D   A   I   I   F   N   S   L   K   E   Q   N   K   V   I

CCACAAGGTCGTTCTCACCCGGTTCAACCTTATCCCGGCGCTTTTGTTAAGGAACCTATT
 P   Q   G   R   S   H   P   V   Q   P   Y   P   G   A   F   V   K   E   P   I

CCAAATCGATACAAATATGTAATGAGTTTCGACCTTACATCTTCAGCTGTAAGTATTATT
 P   N   R   Y   K   Y   V   M   S   F   D   L   T   S   S   A   V   S   I   I

CGCCAAGTGAATATTAGCCCAGAAACAATAGCAGGAACGTTTAAAGTAGCTCCATTGCAT
 R   Q   V   N   I   S   P   E   T   I   A   G   T   F   K   V   A   P   L   H

GATTATATTAACGCTGTTGCTGAACGTCCTTCTGATGTGTACAGTTGTTCTCCTAACGGC
 D   Y   I   N   A   V   A   E   R   P   S   D   V   Y   S   C   S   P   N   G

ATGATGTATTATAAAGACCGTGATGGTGTAGTTCCAACTGAAATCACTAAGGTCTTTAAT
 M   M   Y   Y   K   D   R   D   G   V   V   P   T   E   I   T   K   V   F   N

CAACGTAAAGAACATAAAGGTTACATGCTTGCAGCTCAACGTAATGGTGAAATAATTAAA
 Q   R   K   E   H   K   G   Y   M   L   A   A   Q   R   N   G   E   I   I   K

GAGGCATTGCATAATCCTAATCTTTCTGTTGACGAACCATTAGATGTTGATTATCGTTTC
 E   A   L   H   N   P   N   L   S   V   D   E   P   L   D   V   D   Y   R   F

GACTTCAGCGATGAGATTAAAGAAAAGATTAAAAAGTTGTCTGCTAAATCTCTTAATGAA
 D   F   S   D   E   I   K   E   K   I   K   K   L   S   A   K   S   L   N   E

ATGTTGTTTAGAGCTCAACGTACTGAAGTTGCAGGTATGACTGCACAAATTAACCGTAAA
 M   L   F   R   A   Q   R   T   E   V   A   G   M   T   A   Q   I   N   R   K

TTGCTTATCAACTCACTTTATGGTGCACTTGGCAACGTTTGGTTCCGTTATTATGATTTG
 L   L   I   N   S   L   Y   G   A   L   G   N   V   W   F   R   Y   Y   D   L

CGTAATGCTACTGCAATCACAACATTCGGGCAAATGGCTTTACAGTGGATTGAACGTAAA
 R   N   A   T   A   I   T   T   F   G   Q   M   A   L   Q   W   I   E   R   K
```

FIG. 2B

```
GTTAATGAATATCTGAATGAAGTTTGTGGTACAGAAGGTGAAGCTTTCGTTCTTTATGGT
 V  N  E  Y  L  N  E  V  C  G  T  E  G  E  A  F  V  L  Y  G

GATACAGACTCTATTTACGTATCTGCTGATAAAATTATCGATAAGGTTGGTGAATCTAAA
 D  T  D  S  I  Y  V  S  A  D  K  I  I  D  K  V  G  E  S  K

TTCCGTGATACCAACCATTGGGTAGACTTCTTAGATAAGTTTGCACGTGAACGTATGGAA
 F  R  D  T  N  H  W  V  D  F  L  D  K  F  A  R  E  R  M  E

CCAGCTATTGATAGAGGTTTCCGTGAAATGTGTGAATACATGAACAATAAACAACACTTA
 P  A  I  D  R  G  F  R  E  M  C  E  Y  M  N  N  K  Q  H  L

ATGTTCATGGACCGAGAAGCTATCGCTGGCCTCCGCTTGGTTCTAAAGGTATTGGCGGA
 M  F  M  D  R  E  A  I  A  G  P  P  L  G  S  K  G  I  G  G

TTTTGGACTGGTAAGAAACGTTATGCATTAAACGTGTGGGATATGGAAGGTACTCGTTAC
 F  W  T  G  K  K  R  Y  A  L  N  V  W  D  M  E  G  T  R  Y

GCTGAGCCTAAACTCAAAATCATGGGTCTAGAGACTCAGAAATCTTCGACTCCTAAAGCA
 A  E  P  K  L  K  I  M  G  L  E  T  Q  K  S  S  T  P  K  A

GTACAGAAAGCTCTTAAAGAATGTATTCGTCGTATGCTTCAAGAAGGTGAAGAATCATTA
 V  Q  K  A  L  K  E  C  I  R  R  M  L  Q  E  G  E  E  S  L

CAAGAATATTTTAAAGAGTTTGAAAAAGAATTCCGTCAATTGAATTATATTAGCATCGCG
 Q  E  Y  F  K  E  F  E  K  E  F  R  Q  L  N  Y  I  S  I  A

TCGGTATCTTCTGCGAATAACATTGCTAAATATGACGTAGGTGGATTCCCTGGTCCCAAA
 S  V  S  S  A  N  N  I  A  K  Y  D  V  G  G  F  P  G  P  K

TGCCCGTTCCATATTCGTGGAATTCTGACATATAACCGAGCTATCAAAGGTAATATTGAT
 C  P  F  H  I  R  G  I  L  T  Y  N  R  A  I  K  G  N  I  D

GCACCACAAGTTGTAGAAGGTGAAAAAGTATATGTTCTGCCTTTACGTGAAGGAAACCCA
 A  P  Q  V  V  E  G  E  K  V  Y  V  L  P  L  R  E  G  N  P

TTCGGTGATAAATGTATCGCATGGCCTTCTGGTACTGAAATCACAGATTTAATTAAAGAC
 F  G  D  K  C  I  A  W  P  S  G  T  E  I  T  D  L  I  K  D

GACGTACTTCATTGGATGGACTACACTGTTCTCCTTGAGAAGACATTTATTAAACCACTT
 D  V  L  H  W  M  D  Y  T  V  L  L  E  K  T  F  I  K  P  L

GAAGGATTCACATCAGCAGCGAAACTCGATTACGAGAAGAAAGCATCTCTGTTCGATATG
 E  G  F  T  S  A  A  K  L  D  Y  E  K  K  A  S  L  F  D  M

TTCGATTTT
 F  D  F
```

MUTANT RB69 DNA POLYMERASE

CROSS-REFERENCE TO RELATED APPLICATIONS

This application is a continuation of U.S. Nonprovisional Application No. 13/600,416, filed on Aug. 31, 2012, now issued U.S. Patent No. 8,703,461, which is a continuation of U.S. Nonprovisional Application No. 12/790,768, filed on May 28, 2010, now abandoned, which claims the filing date benefit of U.S. Provisional Application No. 61/263,320, filed on Nov. 20, 2009; and the subject application claims the filing date benefit of U.S. Non-provisional Application No. 14/108, 166, filed on Dec. 16, 2013, which is a continuation of U.S. Non-provisional Application No. 12/790,760, filed on May 28, 2010, now issued U.S. Patent No. 8,632,975, which claims the filing date benefit of U.S. Provisional Application Nos.: 61/184,774, filed on Jun. 5, 2009; 61/242,762, filed on Sep. 15, 2009; and 61/295,533, filed on Jan. 15, 2010. The contents of each of the foregoing patent applications are incorporated by reference in their entirety for all their purposes.

FIELD

The disclosure relates generally to mutant DNA-dependent polymerases which are derived from or otherwise related to RB69 polymerases. The mutant RB69 polymerases disclosed herein are capable of binding and/or incorporating labeled nucleotides. Typically, the nucleotide binding and/or incorporation properties of these mutant polymerases are altered, e.g., increased or decreased, relative to the corresponding nucleotide binding and/or incorporation properties of wild type RB69 polymerase.

BACKGROUND

DNA polymerases typically catalyze nucleic acid synthesis using polynucleotide templates and employ Watson-Crick base pairing interactions between the template-based-nucleotide and incoming nucleotides which bind at the polymerase active site. DNA polymerases are useful in a variety of biological applications, including DNA sequencing applications.

Certain single molecule DNA sequencing methods encompass two steps, relying on nucleotide transient-binding to the polymerase, instead of nucleotide incorporation (e.g., Vander Horn, et al., U.S. Ser. No. 61/184,774; 61/242,763; and 61/295,533). The first step includes transiently-binding an incoming nucleotide (e.g., labeled nucleotide) with a polymerase under conditions which inhibit incorporation of the bound nucleotide, and the identifying the transiently-bound nucleotide. The second step includes incorporating a single nucleotide (e.g., terminator nucleotide) so as to translocate the polymerase to the next position on the DNA template. The transiently-bound nucleotide can be replaced with the nucleotide to be incorporated.

It is desirable to perform the first and second steps under moderate temperature conditions (e.g., room temperature) with one type of DNA polymerase. It is also desirable to use a DNA polymerase which binds incorporating incoming nucleotides that are complementary to the template-based-nucleotide. It is also desirable to use a DNA polymerase which exhibits increased transient-binding duration (without nucleotide incorporation) for the incoming nucleotides, to increase the binding duration of a labeled nucleotide to a polymerase, so as to increase detection and identity of the bound nucleotide.

However, existing polymerases cannot be used to perform the first and second steps because they lack certain properties. For example, many DNA polymerases do not selectively bind labeled nucleotides. Similarly, many DNA polymerases do not efficiently incorporate terminator nucleotides. Some DNA polymerases can exhibit short nucleotide binding duration, or can catalyze nucleotide incorporation under conditions when transient nucleotide binding is desired. Additionally, some DNA polymerases can exhibit undesirable behaviors such as binding non-complementary incoming nucleotides, or incorporating non-complementary incoming nucleotides.

Thus, existing polymerases offer limited utility for conducting certain two-step, single molecule sequencing methods. These and other desirable properties can be enhanced via modifying and selecting a DNA polymerase. Provided herein are mutant RB69 DNA polymerases which are useful for conducting these two-step DNA sequencing methods. In some embodiments, these mutant DNA polymerases can selectively and transiently bind labeled nucleotides. In some embodiments, the mutant DNA polymerases can incorporate terminator nucleotides.

SUMMARY

Provided herein are novel DNA polymerase compositions, methods of making such compositions and methods of using such compositions in various biological applications.

Provided herein are isolated mutant DNA polymerases capable of selectively transiently-binding a labeled nucleotide and selectively incorporating a terminator nucleotide. In one embodiment, the isolated mutant DNA polymerase comprises a mutant RB69 DNA polymerase. In another embodiment, the isolated mutant DNA polymerase comprises the amino acid sequence according to any one of SEQ ID NOS: 1-8. In another embodiment, the isolated mutant DNA polymerase further comprises a reporter moiety. In another embodiment, the reporter moiety can be an energy transfer donor moiety. In another embodiment, the energy transfer donor moiety can be a fluorescent dye or a nanoparticle.

Also provided herein are systems comprising a mutant DNA polymerase bound to a DNA template and a primer, and a nucleotide transiently-bound to the mutant DNA polymerase, where the mutant DNA polymerase may be capable of selectively transiently-binding a labeled nucleotide and selectively incorporating a terminator nucleotide. In one embodiment, the system comprises a mutant DNA polymerase which can be a mutant RB69 DNA polymerase. In another embodiment, the system comprises a mutant DNA polymerase having the amino acid sequence according to any one of SEQ ID NOS:1-8. In another embodiment, the system comprises a mutant DNA polymerase which further includes a reporter moiety. In another embodiment, the reporter moiety can be an energy transfer donor moiety. In another embodiment, the energy transfer donor moiety can be a fluorescent dye or a nanoparticle.

Also provided are nucleic acid molecules encoding the mutant DNA polymerase which may be capable of selectively transiently-binding a labeled nucleotide and selectively incorporating a terminator nucleotide. In one embodiment, the nucleic acid molecule can be DNA or RNA.

Also provided herein are vectors, comprising the nucleic acid molecule which encodes the mutant DNA polymerase which may be capable of selectively transiently-binding a labeled nucleotide and selectively incorporating a terminator nucleotide. In one embodiment, the vector further comprising a promoter sequence joined with the nucleic acid molecule encoding the mutant DNA polymerase. In one embodiment, the promoter can be constitutive or inducible.

Also provided herein are host cells carrying the vector which comprises the nucleic acid molecule which encodes the mutant DNA polymerase which may be capable of selectively transiently-binding a labeled nucleotide and selectively incorporating a terminator nucleotide. In one embodiment, the host cell can be a phage, a prokaryote cell or a eukaryote cell.

Also provided herein are methods for producing a mutant DNA polymerase polypeptide, comprising culturing host cells under conditions suitable for the host cell to produce the mutant DNA polymerase polypeptide. In one embodiment, the host cells carry the vector which comprises the nucleic acid molecule which encodes the mutant DNA polymerase which may be capable of selectively transiently-binding a labeled nucleotide and selectively incorporating a terminator nucleotide. Also provided are mutant DNA polymerase produced by this method.

BRIEF DESCRIPTION OF THE DRAWINGS

FIGS. 1A-C shows the nucleotide and amino acid sequences of native RB69 polymerase (amino acid: SEQ ID NO:1) (nucleotide: SEQ ID NO:9).

FIGS. 2A-C shows the nucleotide and amino acid sequences of an exemplary mutant RB69 polymerase called "3PDX" according to the present disclosure (amino acid: SEQ ID NO:2) (nucleotide: SEQ ID NO:10).

Figure 3A:
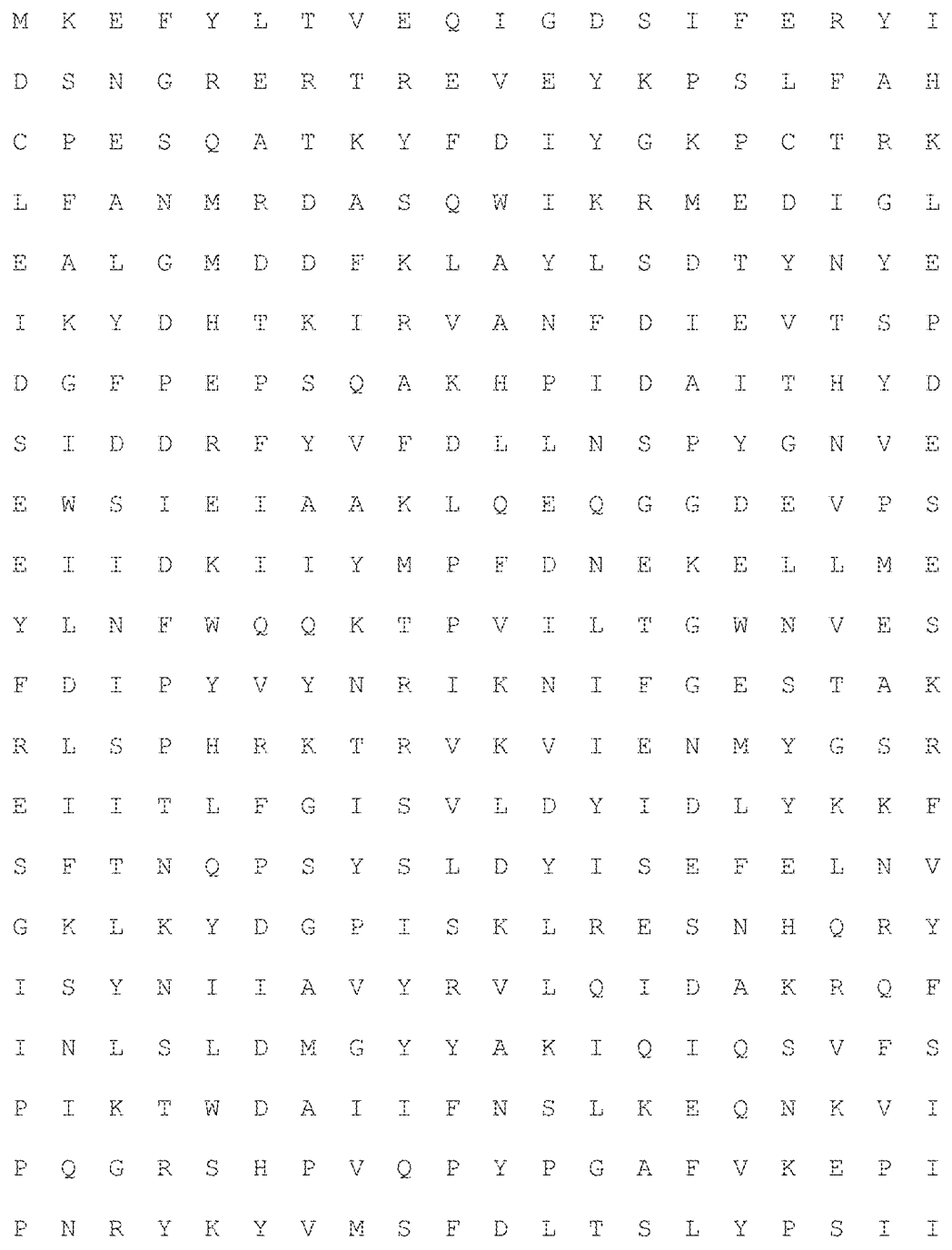
Figure 3B:
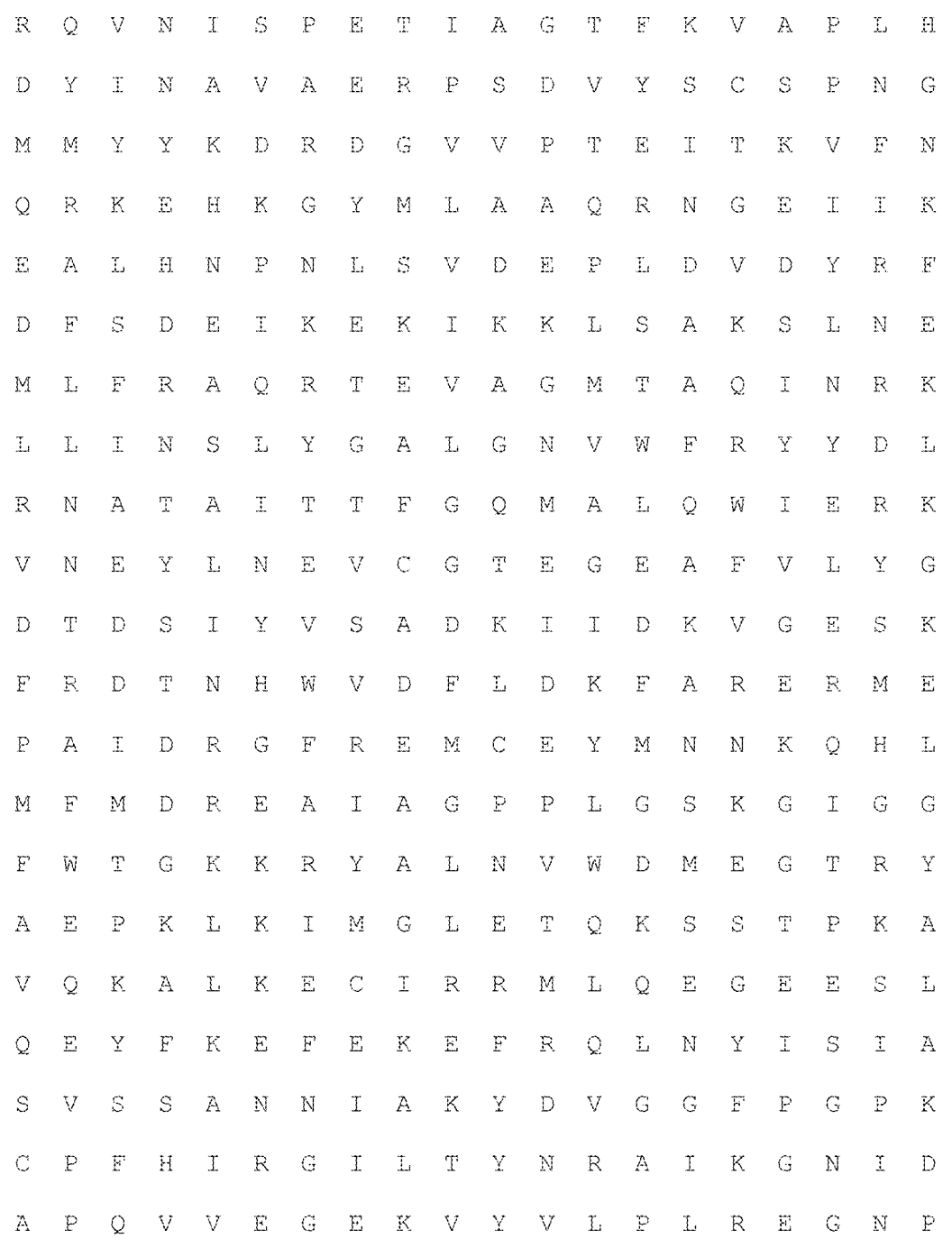
Figure 3C:
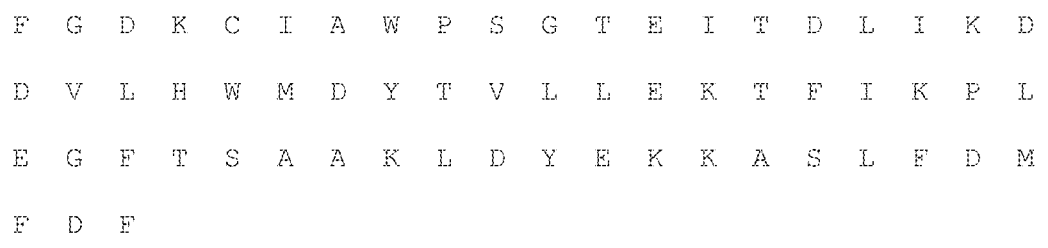

FIGS. 3A-C shows the amino acid sequences of an exemplary mutant RB69 polymerase called "SX" according to the present disclosure (amino acid: SEQ ID NO:3).

Figure 4A:
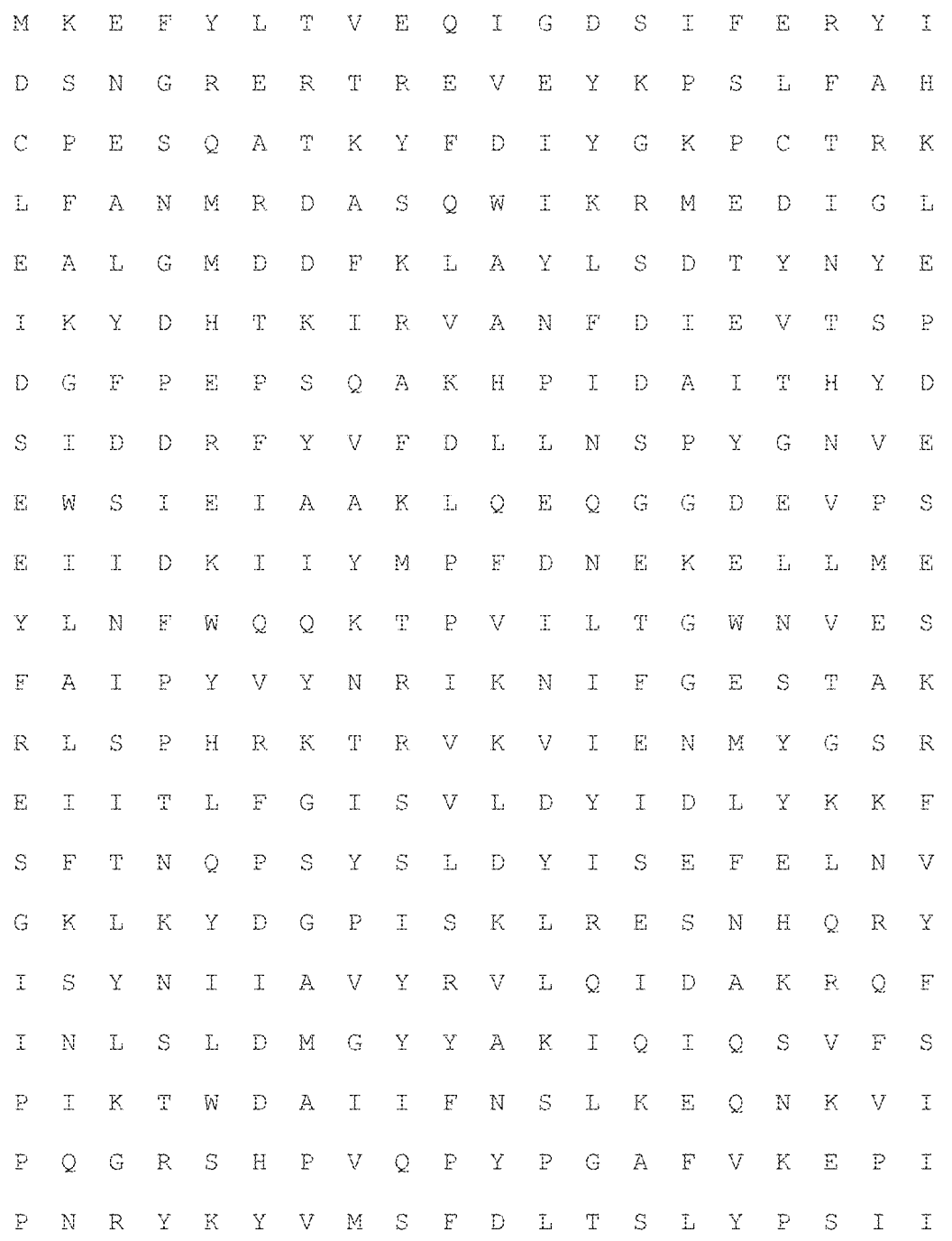
Figure 4B:
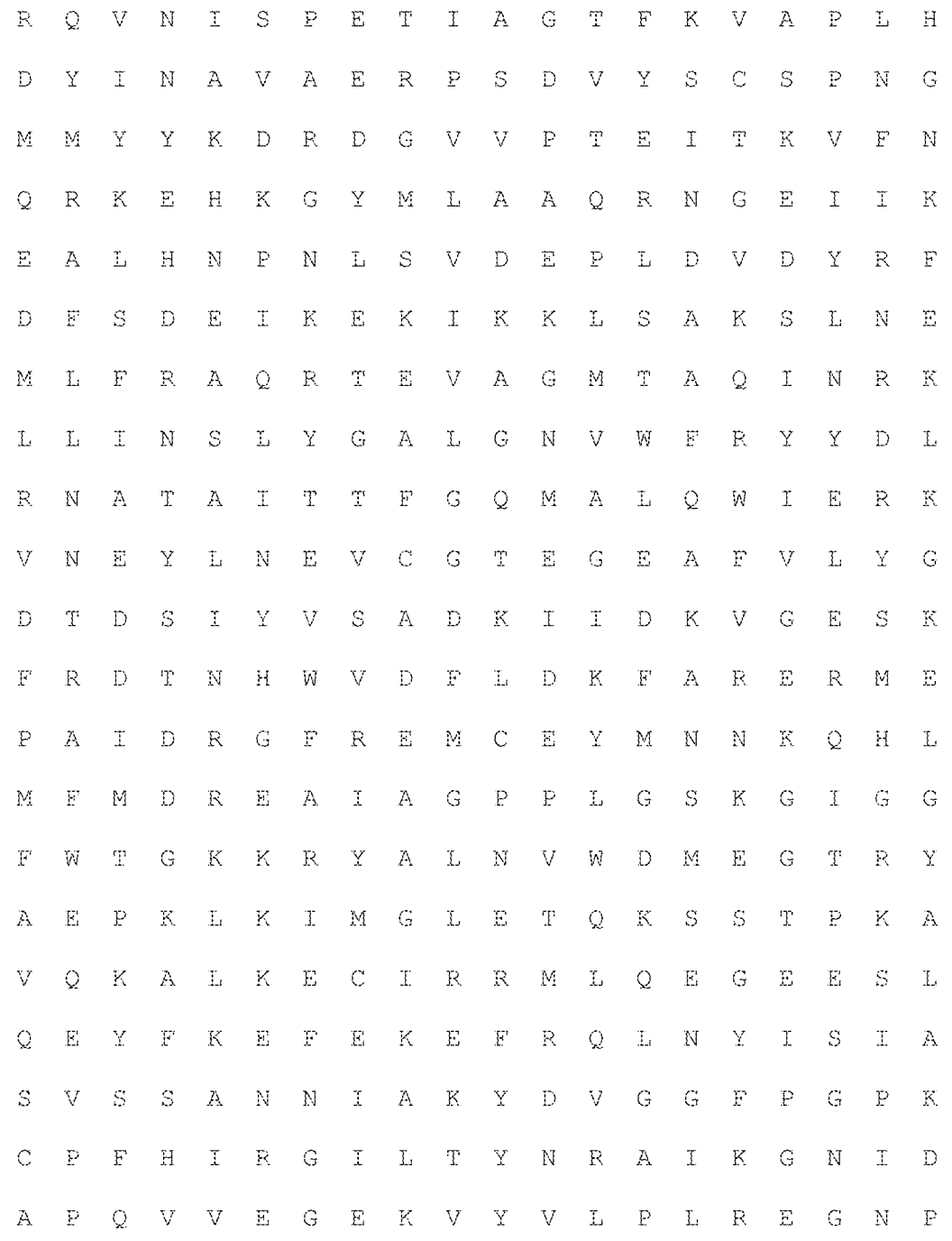
Figure 4C:
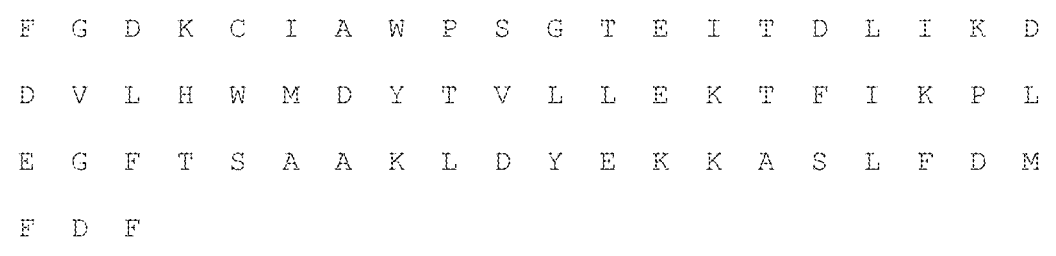

FIGS. 4A-C shows the amino acid sequences of an exemplary mutant RB69 polymerase called "DX" according to the present disclosure (amino acid: SEQ ID NO:4).

Figure 5A:
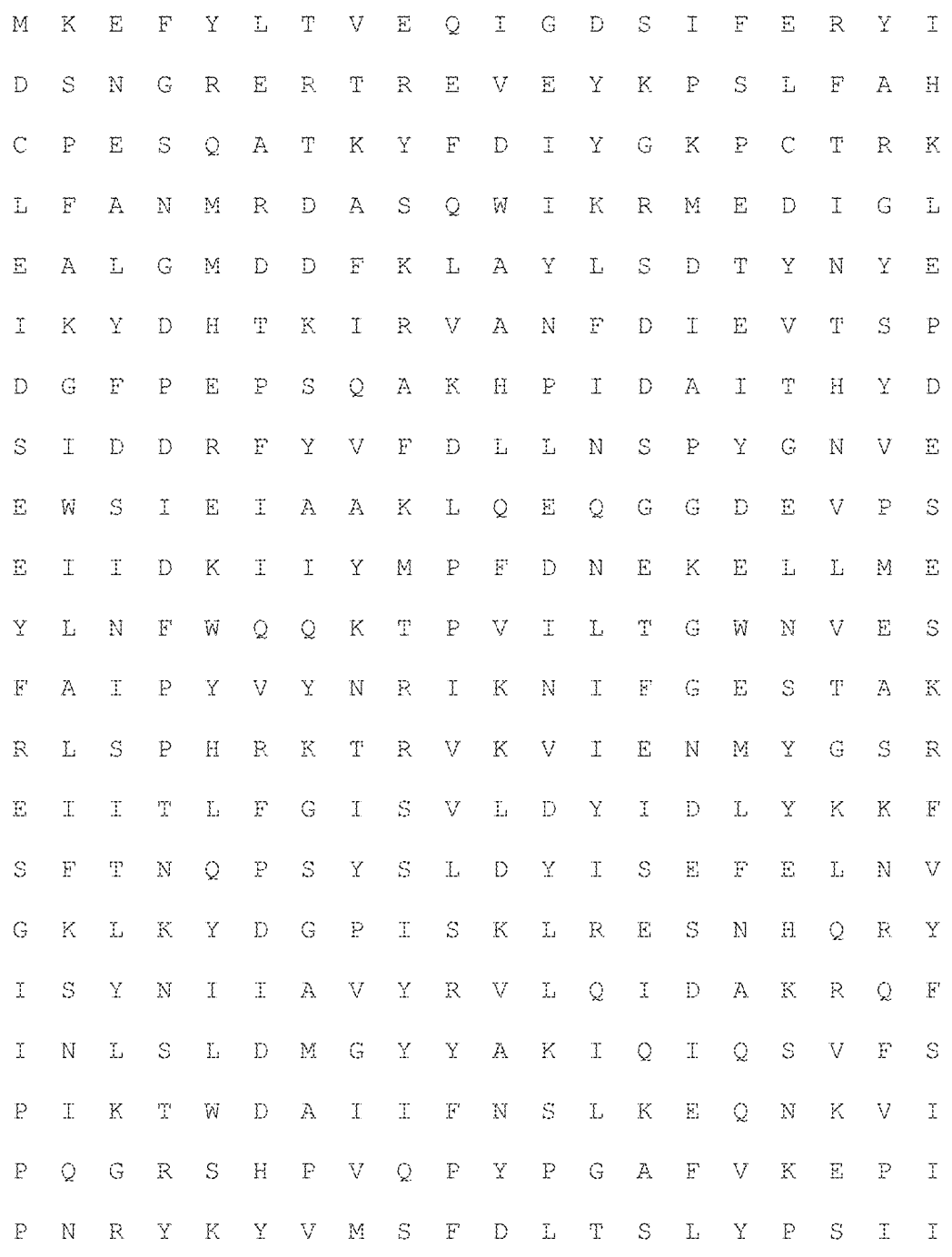
Figure 5B:
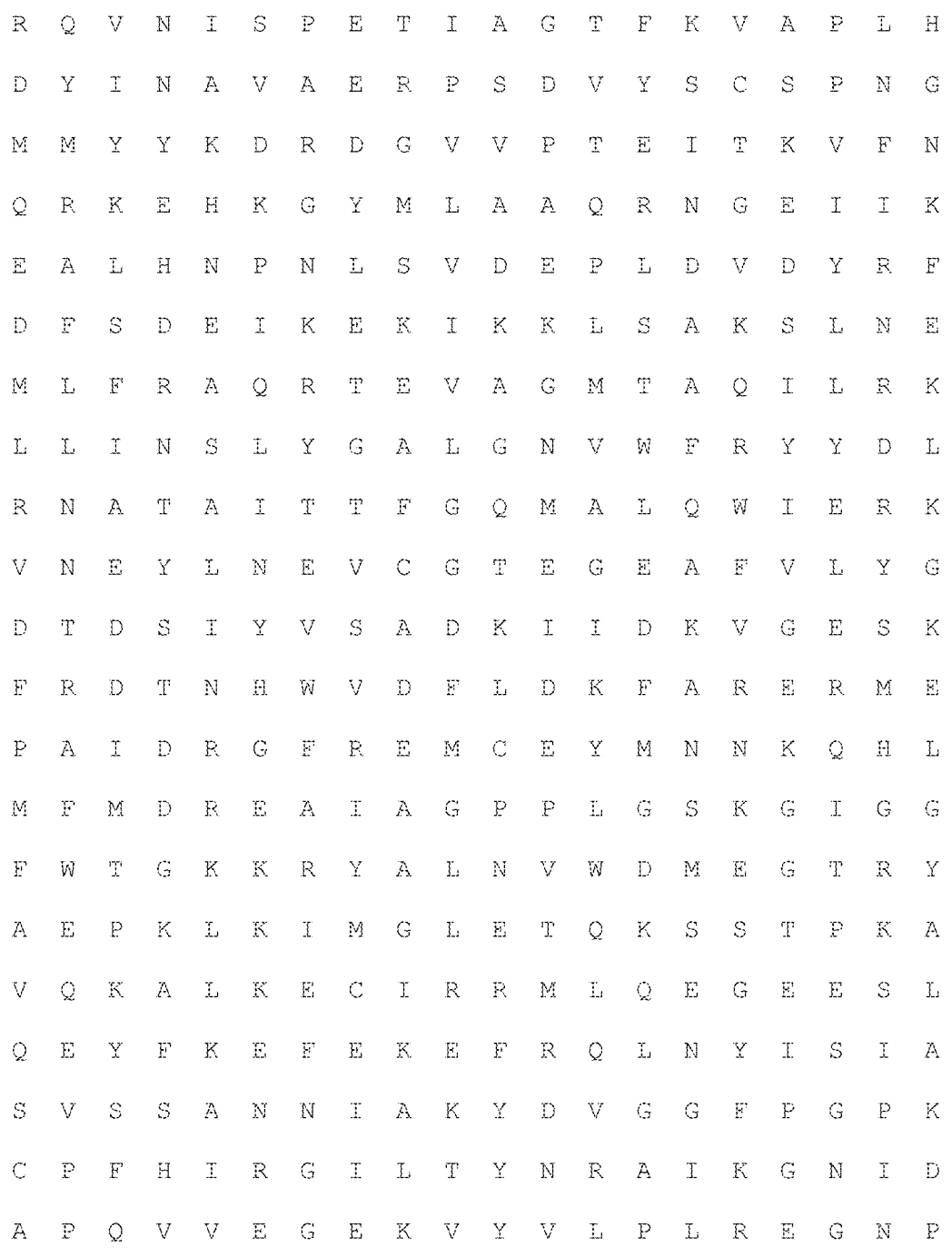
Figure 5C:
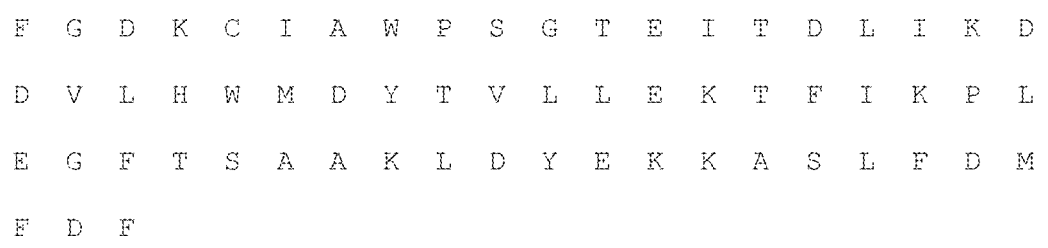

FIGS. 5A-C shows the amino acid sequences of an exemplary mutant RB69 polymerase called "FDX" according to the present disclosure (amino acid: SEQ ID NO:5).

Figure 6A:
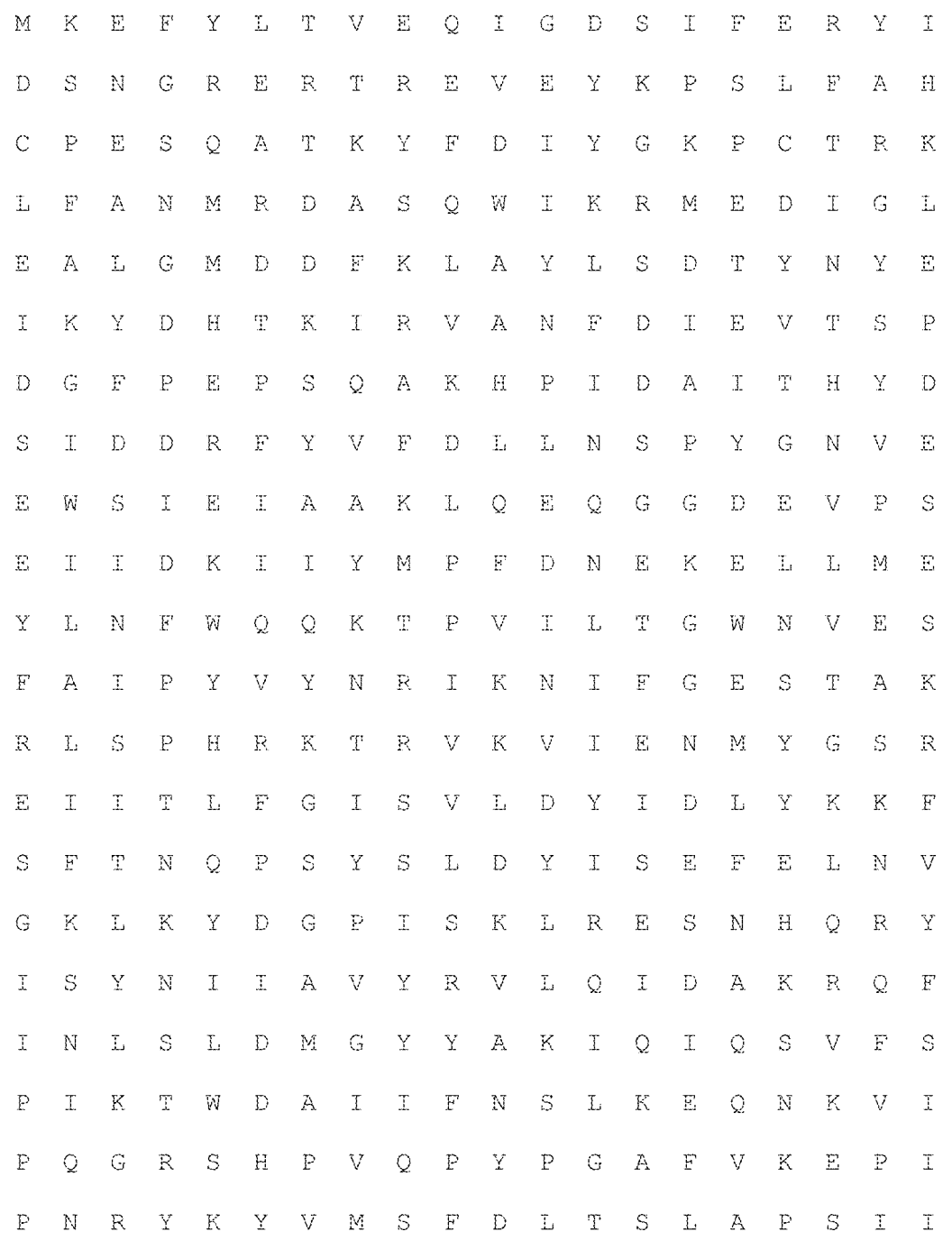
Figure 6B:
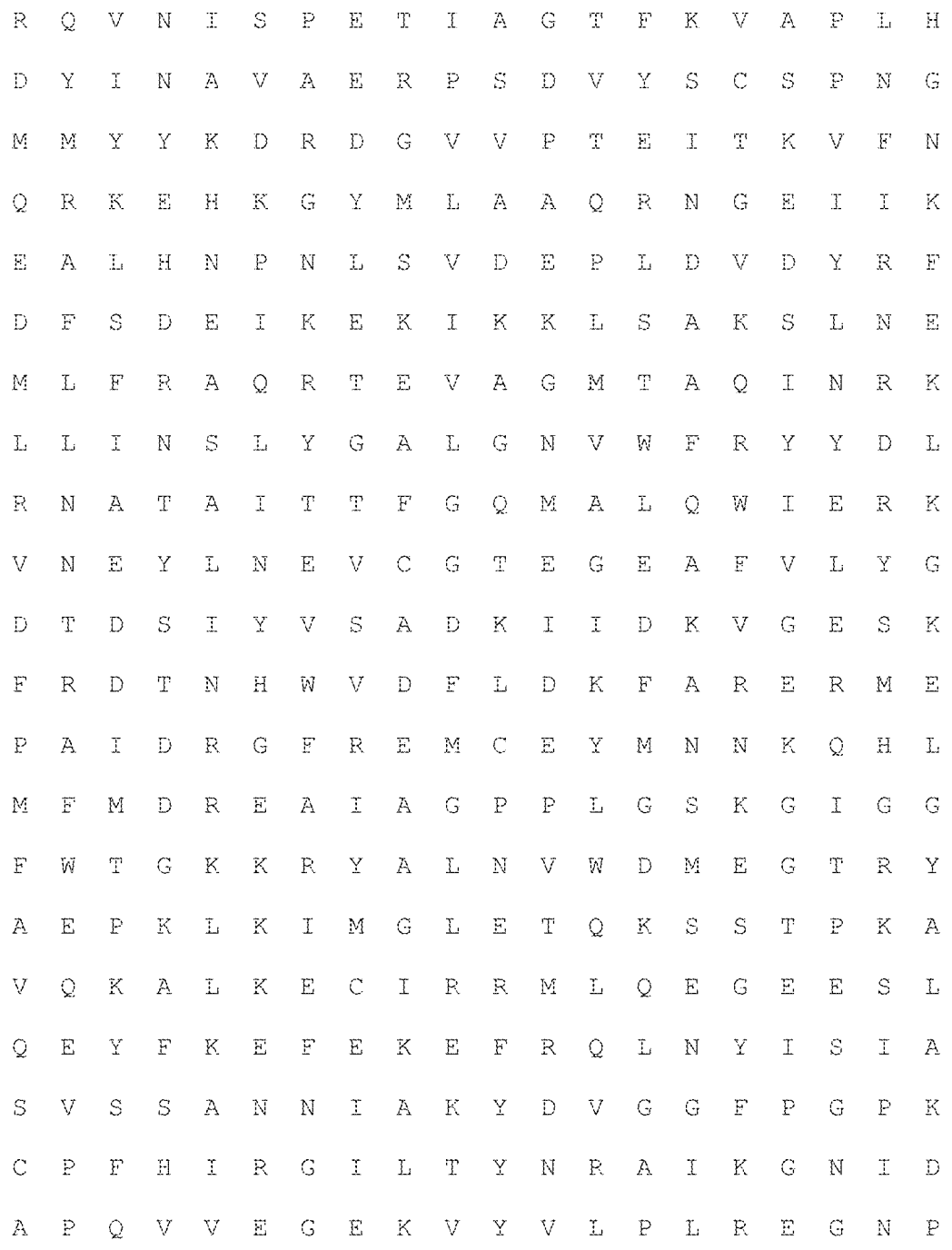
Figure 6C:
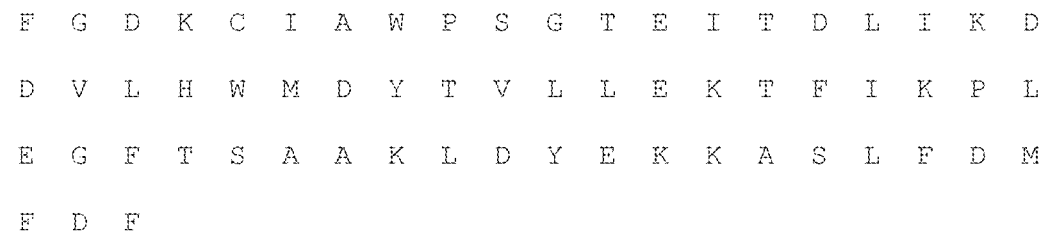

FIGS. 6A-C shows the amino acid sequences of an exemplary mutant RB69 polymerase called "PDX" according to the present disclosure (amino acid: SEQ ID NO:6).

Figure 7A:
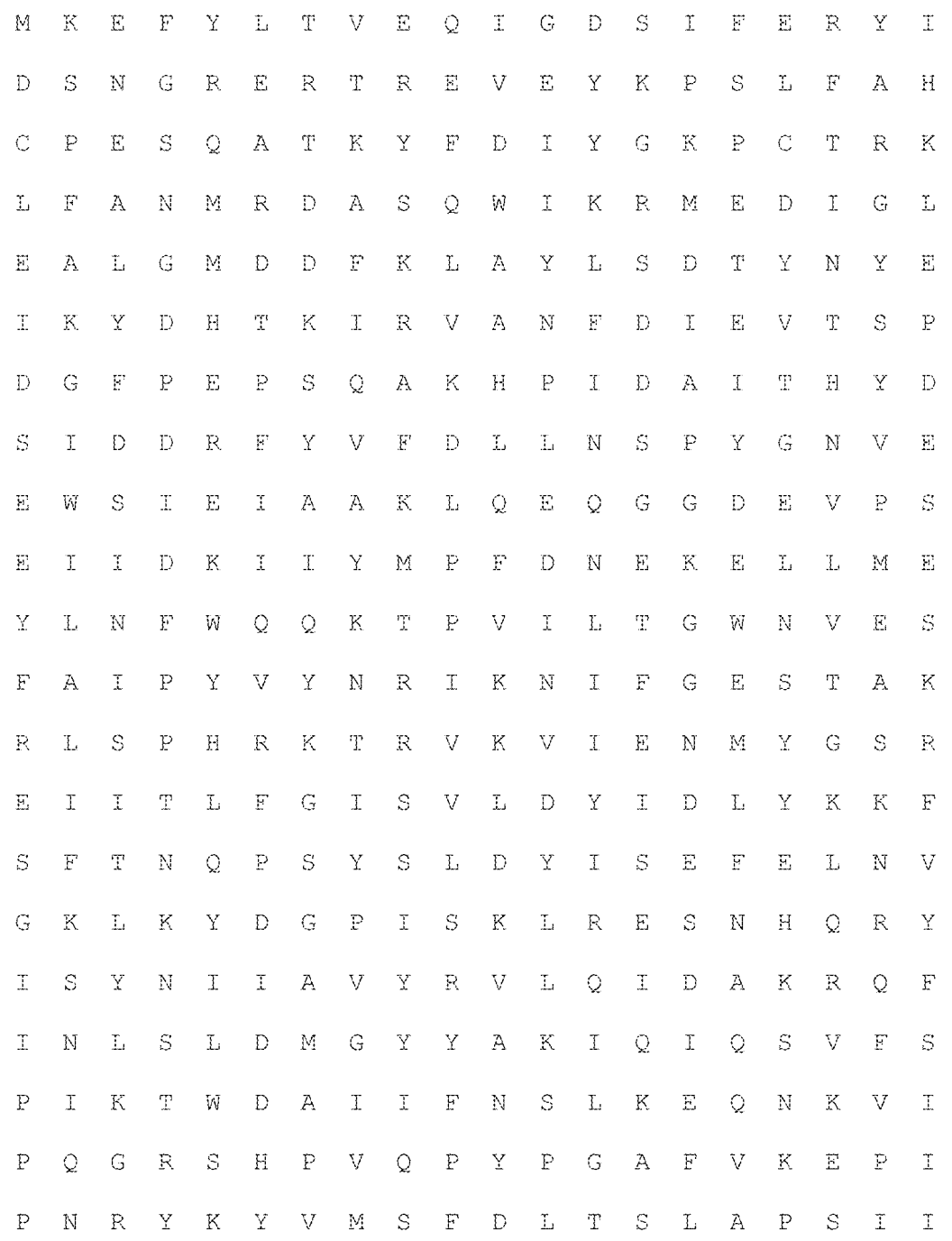
Figure 7B:
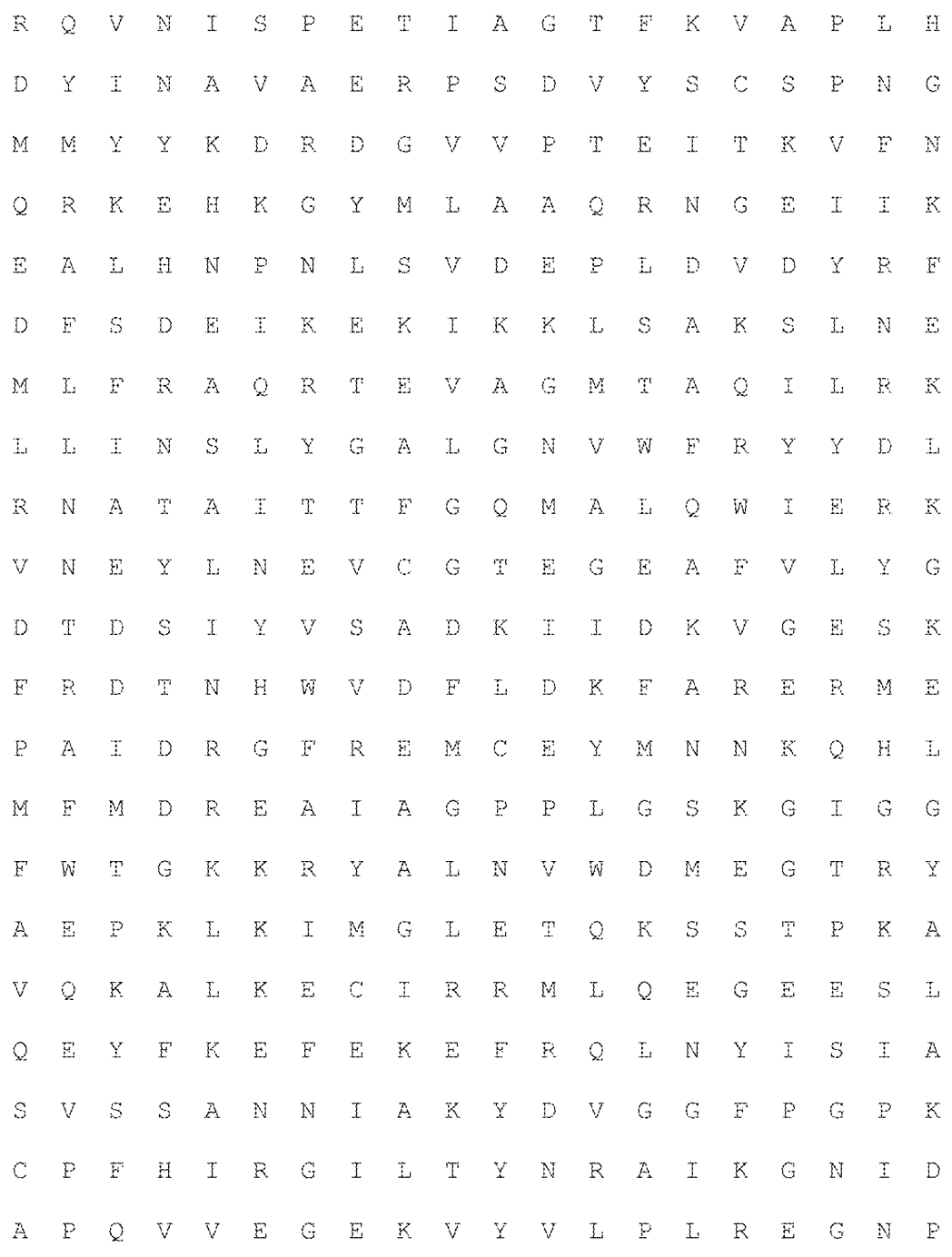
Figure 7C:
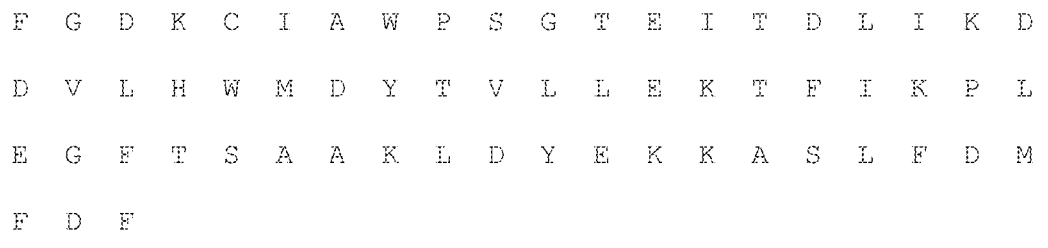

FIGS. 7A-C shows the amino acid sequences of an exemplary mutant RB69 polymerase called "FPDX" according to the present disclosure (amino acid: SEQ ID NO:7).

Figure 8A:
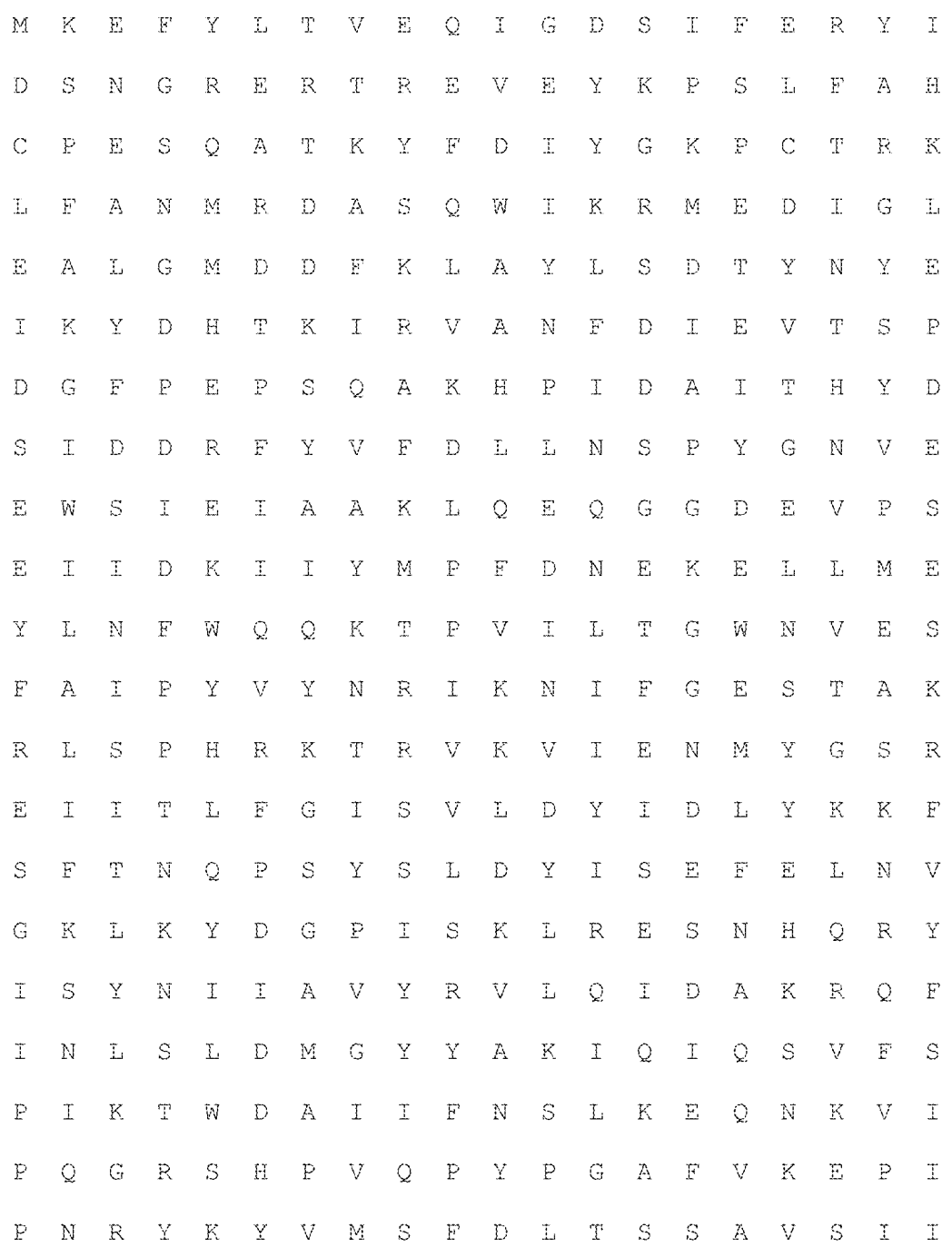
Figure 8B:
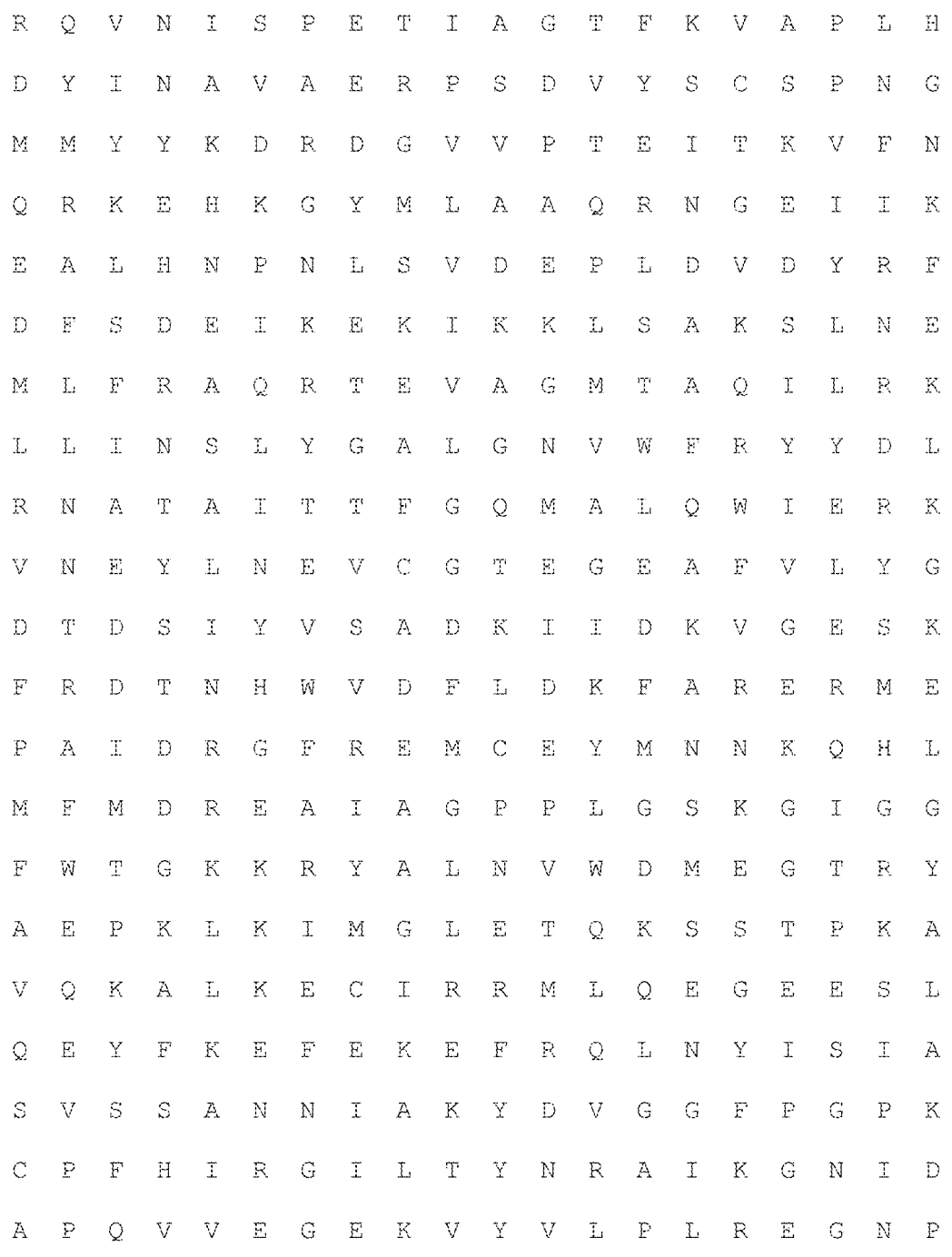
Figure 8C:
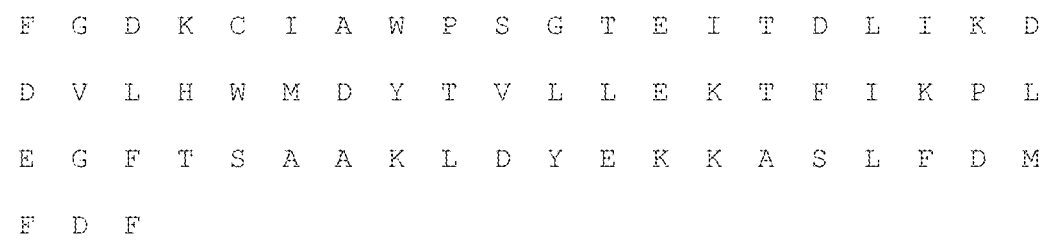

FIGS. 8A-C shows the amino acid sequences of an exemplary mutant RB69 polymerase called "F3PDX" according to the present disclosure (amino acid: SEQ ID NO:8).

DETAILED DESCRIPTION

Figure 9A:
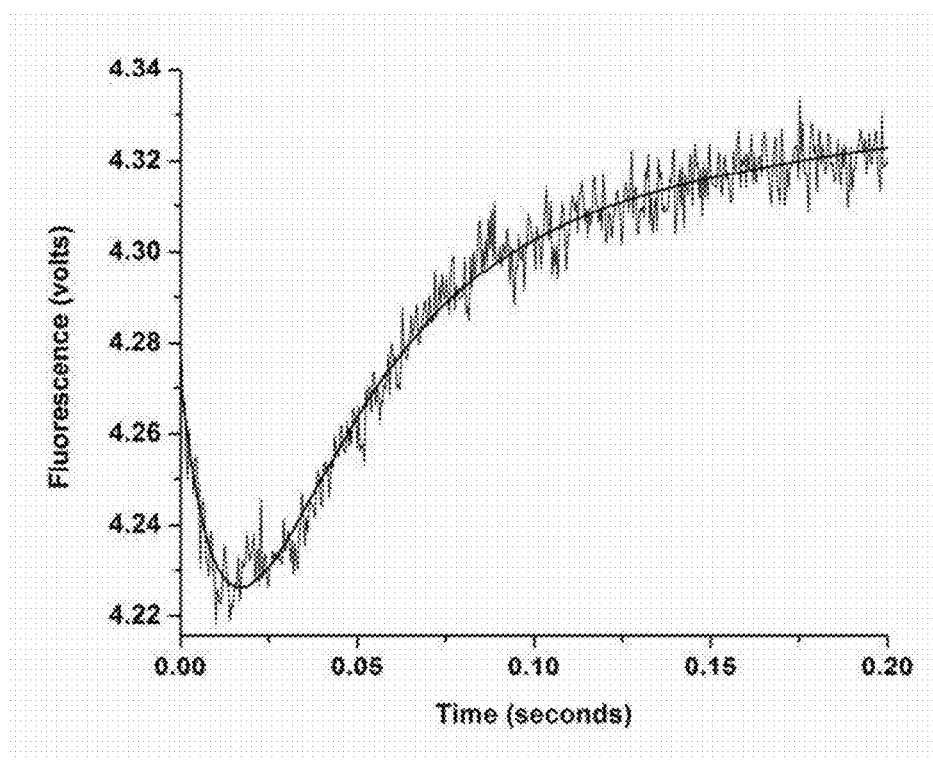
FIG. 9A shows a stopped-flow fluorescence trace ($t_{pol}$) for Phi29 (exo-) polymerase and terminal phosphate labeled dN4P nucleotides in the presence of manganese (Example 2).

Provided herein are mutant DNA-dependent polymerases which are derived from, or otherwise related to, wild type RB69 DNA polymerase. These mutant polymerases are capable of selectively binding labeled nucleotides. These mutant polymerases are also capable of incorporating a variety of naturally occurring and modified nucleotides, including, for example, terminator nucleotides, dideoxynucleotides, acyclo-nucleotides, 3' modified nucleotides (e.g., 3' azido-modified nucleotides), and/or ribonucleotides. These mutant RB69 polymerases can be used for various nucleotide incorporation methods and sequencing methods, including but not limited to the methods disclosed in U.S. Ser. Nos. 61/164,324, filed on Mar. 27, 2009; 61/184,774, filed on Jun. 5, 2009; and 61/242,762, filed on Sep. 15, 2009.

Also provided herein are DNA sequencing methods using the mutant DNA polymerases. The methods encompass two steps: a nucleotide binding step, and a nucleotide incorporation step. In the nucleotide binding step, the nucleotide binds the active site of the polymerase and dissociates as an intact nucleotide (i.e., no cleavage and release of the phosphate groups).

Unless defined otherwise, all technical and scientific terms used herein have the same meaning as is commonly understood by one of ordinary skill in the art to which these inventions belong. All patents, patent applications, published applications, treatises and other publications referred to herein, both supra and infra, are incorporated by reference in their entirety. If a definition and/or description is explicitly or implicitly set forth herein that is contrary to or otherwise inconsistent with any definition set forth in the patents, patent applications, published applications, and other publications that are herein incorporated by reference, the definition and/or description set forth herein prevails over the definition that is incorporated by reference.

The practice of the present disclosure will employ, unless otherwise indicated, conventional techniques of molecular biology, microbiology and recombinant DNA techniques, which are within the skill of the art. Such techniques are explained fully in the literature. See, for example, Sambrook, J., and Russell, D. W., 2001, *Molecular Cloning: A Laboratory Manual*, Third Edition; Ausubel, F. M., et al., eds., 2002, *Short Protocols In Molecular Biology*, Fifth Edition.

As used herein, the terms "comprising" (and any form or variant of comprising, such as "comprise" and "comprises"), "having" (and any form or variant of having, such as "have" and "has"), "including" (and any form or variant of including, such as "includes" and "include"), or "containing" (and any form or variant of containing, such as "contains" and "contain"), are inclusive or open-ended and do not exclude additional, unrecited additives, components, integers, elements or method steps.

As used herein, the terms "a," "an," and "the" and similar referents used herein are to be construed to cover both the singular and the plural unless their usage in context indicates otherwise. Accordingly, the use of the word "a" or "an" when used in the claims or specification, including when used in conjunction with the term "comprising", may mean "one," but it is also consistent with the meaning of "one or more," "at least one," and "one or more than one."

As used herein, the term "operably linked" and its variants refer to chemical fusion or bonding or association of sufficient stability to withstand conditions encountered in the nucleotide incorporation methods utilized, between a combination of different compounds, molecules or other entities such as, but not limited to: between a mutant polymerase and a reporter moiety (e.g., fluorescent dye or nanoparticle), or between a nucleotide and a reporter moiety (e.g., fluorescent dye).

As provided herein, the terms "polymerase" and "polymerases" are biologically active polypeptide molecules, or fragments thereof, that catalyze transfer of a nucleoside monophosphate from a nucleoside polyphosphate (or analog thereof) to the terminal 3' hydroxyl group of the polymerization initiation site (i.e., nucleotide polymerization). The terminal 3' hydroxyl group of a primer, or a gap or nick, or of a self-priming template, provides the polymerization initiation site for DNA polymerase.

Other objects, features and advantages of the disclosed methods, systems and compositions will become apparent from the following detailed description. It should be understood, however, that the detailed description and the specific examples, while indicating specific embodiments, are given by way of illustration only, since various changes and modifications within the spirit and scope of the inventions provided herein will become apparent to those skilled in the art from this detailed description.

Mutant RB69 Polymerases

In some embodiments, provided herein are mutant RB69 DNA polymerases which are mutated versions of a wild-type RB69 polymerase comprising the amino acid sequence of SEQ ID NO: 1 as shown in FIG. 1. These mutant DNA polymerases offer various advantages not provided by other DNA polymerases. In some embodiments, the mutant polymerases of the present disclosure exhibit altered nucleotide binding and/or nucleotide incorporation behavior compared to wild type RB69 polymerase. For example, in some embodiments the mutant polymerases can exhibit increased affinity or duration of nucleotide binding in the presence of labeled nucleotides. In some embodiments, the mutant polymerases can exhibit increased ability to incorporate labeled nucleotides and/or terminator nucleotides.

The mutant polymerases provided herein can be used, for example, in certain single molecule DNA sequencing methods which encompass two steps: a nucleotide binding step, and/or a nucleotide incorporation step. Some single molecule sequencing methods require transient binding of the nucleotide to the polymerase (see e.g., Vander Horn, et al., U.S. Ser. No. 61/184,774; 61/242,763; 61/295,533; and "Mutant DNA Polymerases", concurrently filed with this application on May 28, 2010, by P. Vander Horn, et al.).

In the transient-binding step, an incoming nucleotide (e.g., labeled nucleotide) binds with the polymerase under conditions which inhibit incorporation of the bound nucleotide, and the identity of the transiently-bound nucleotide is determined. In the second step, a single nucleotide is incorporated (e.g., terminator nucleotide) so as to translocate the polymerase to the next position on the DNA template.

The mutant DNA polymerases provided herein can be used for the first and/or second steps and can provide improved performance in the first and/or second steps relative to wild-type RB69 polymerase. In certain embodiments, the labeled nucleotide in step one can be replaced with a terminator nucleotide in step two.

In some embodiments, the mutant polymerases can be mesophilic polymerases. For example, the mesophilic polymerases can transiently-bind a nucleotide and/or catalyze nucleotide polymerization at moderate temperatures. The moderate temperatures can range from about 15-40° C., or about 15-30° C., or about 15-25° C.

In some embodiments, the mutant polymerases can selectively bind an incoming nucleotide which is complementary to the template-based-nucleotide to form base-pairing interactions.

Typically, the complementary incoming nucleotides and template-based-nucleotides used in the methods of the present disclosure can form hydrogen bonds by Watson-Crick or Hoogstein binding to form a duplex nucleic acid structure. The complementary base pairing can be the standard A-T or C-G base pairing, or can be other forms of base-pairing interactions.

In some embodiments and under suitable conditions, the mutant polymerases can transiently-bind a nucleotide, without incorporating the bound nucleotide. The suitable conditions include transiently-binding a nucleotide to the mutant polymerase in the presence of any combination of: (1) reduced levels or omission of a metal cation that permits nucleotide incorporation (e.g., manganese and/or magnesium) and/or addition of a cation that inhibits nucleotide incorporation (e.g., calcium); and/or (2) the transiently-bound nucleotide is a non-incorporatable nucleotide. In some embodiments, the mutant polymerases can transiently bind to a nucleotide with higher affinity and/or for longer duration than a wild type RB69 polymerase comprising the amino acid sequence of SEQ ID NO: 1.

In some embodiments, the mutant polymerases can transiently-bind a nucleotide which is unlabeled, or a nucleotide which is operably linked to a reporter moiety. In some embodiments, the mutant polymerases can transiently-bind to a labeled nucleotide with higher affinity and/or for longer duration than a wild type RB69 polymerase comprising the amino acid sequence of SEQ ID NO: 1. An exemplary assay for transient-binding to a labeled nucleotide is provided herein in Example 2; however, any other suitable assay can also be employed.

In some embodiments, the mutant polymerases can exhibit an enhanced ability to incorporate nucleotides, such as terminator nucleotides (Gardner and Jack 1999 Nucleic Acids Research 27:2545-2555; Gardner and Jack 2002 Nucleic Acids Research 30:605-613), including dideoxynucleotides, acyclo-nucleotides, 3' mutant nucleotides including 3' azidomutant nucleotides, and/or ribonucleotides. In some embodiments, the mutant polymerases can incorporate a terminator nucleotide with higher efficiency than a wild RB69 polymerase comprising the amino acid sequence of SEQ ID NO: 1. An exemplary assay for incorporation of a labeled nucleotide is provided herein in Example 2; however, any other suitable assay can also be employed.

The mutant polymerases are useful in methods involving successive nucleotide incorporation events, such as DNA sequencing. The mutant polymerase can be used for partial ribosubstitution (WF Barnes 1978 Journal of Molecular Biology 119: 83-99), chain terminating DNA sequencing using dideoxynucleotides (Sanger, Nicklen, and Coulson 1977 Proc. Natl. Acad. Sci. USA 74:5463-5467) or acyclo-nucleotides (GL Trainor 1996 U.S. Pat. No. 5,558,991), and/or SNP analysis using dideoxynucleotides or acyclo-nucleotides (Haff and Simirnov 1997 Genome Methods 7:378-388).

Isolated Mutant Polymerases

Provided herein are mutant polymerases which include intact subunits, biologically-active fragments, mutant variants, fusion variants, naturally occurring polymerases, or non-naturally occurring polymerases. The mutations can include amino acid substitutions, insertions, or deletions.

In yet another aspect, the mutant polymerases can be isolated from a cell, or generated using recombinant DNA technology or chemical synthesis methods. In another aspect, the mutant polymerases can be expressed in prokaryote, eukaryote, viral, or phage organisms. In another aspect, the mutant polymerases can be post-translationally mutant proteins or fragments thereof.

In one aspect, the mutant polymerase can be a recombinant protein which is produced by a suitable expression vector/host cell system. The mutant polymerases can be produced by suitable recombinant expression vectors carrying inserted nucleotide sequences that encode the mutant polymerases. A nucleic acid molecule encoding the mutant polymerase sequence can be operably linked to a suitable expression vector. The nucleic acid molecule can be inserted in-frame into the suitable expression vector. The suitable expression vector, having the inserted nucleic acid molecule, can enter a host cell. The suitable expression vector can replicate in the host cell, such as a phage host, or a prokaryotic or eukaryotic host cell. The suitable expression vector can replicate autonomously in the host cell, or can be inserted into the host cell's genome and be replicated as part of the host genome. The suitable expression vector can carry a selectable marker that confers resistance to drugs (e.g., kanamycin, ampicillin, tetracycline, chloramphenicol, or the like), or confers a nutrient requirement. The suitable expression vector can have one or more restriction sites for inserting the nucleic acid molecule of interest. The suitable expression vector can include expression control sequences for regulating transcription and/or translation of the encoded sequence. The expression control sequences can include: promoters (e.g., inducible or constitutive), enhancers, transcription terminators, and secretion signals. The expression vector can be a plasmid, cosmid, or phage vector. Many expression vectors and suitable host cells are known. The expression vector can enter a host cell which can replicate the vector, produce an RNA transcript of the inserted sequence, and/or produce protein encoded by the inserted sequence. The recombinant mutant polymerase can include an affinity tag for enrichment or purification, including a poly-amino acid tag (e.g., poly His tag), GST, and/or HA sequence tag.

Methods for Preparing the Mutant Polymerases

Provided herein are methods for preparing the mutant polymerases using the suitable recombinant expression vectors and host cells. Preparing recombinant proteins by expressing the RNA and/or protein encoded by the inserted sequences are well known (Sambrook et al, *Molecular Cloning* (1989)). For example, the host cell which carries the expression vector which is capable of producing the mutant polymerase, can be cultured in a suitable growth medium (e.g., liquid or semi-solid) having antibiotics for selection. The host cell can be cultured for a suitable amount of time (e.g., 8-48 hours), under a suitable temperature range (e.g., 15-40° C.), with or without aeration. The cultured host cells can be harvested, and the mutant polymerases produced in the host cell can be extracted from the host cell. The extracted mutant polymerases can be separated from non-desirable components of the host cell (e.g., cell wall, DNA, RNA, other proteins) to form an enriched preparation of mutant DNA polymerases. The enriched preparation can be concentrated using well-known methods. One exemplary method for isolating a mutant polymerase of the present disclosure is provided herein in Example 1; however, any other suitable method can be employed.

Selecting Mutant Polymerases

Selecting the mutant polymerases for use in nucleotide transient-binding and/or the nucleotide incorporation methods can be based on certain desired polymerase kinetics. For example, the desired polymerase kinetics can be evaluated with respect to any of the following aspects of polymerase behavior: nucleotide transient-binding (e.g., association), nucleotide dissociation (intact nucleotide), nucleotide fidelity, nucleotide incorporation (e.g., catalysis), and/or release of the cleavage product.

In some embodiments, the mutant polymerases may be selected which retain the ability to selectively bind complementary nucleotides. In some embodiments, the mutant polymerases may be selected that exhibit a modulated rate (faster or slower) of nucleotide association or dissociation. In some embodiments, the mutant polymerases may be selected that exhibit a reduced rate of nucleotide incorporation activity (e.g., catalysis) and/or a reduced rate of dissociation of the cleavage product. Examples of other preparing and selecting mutant polymerases that exhibit nucleotide binding and a reduced rate of nucleotide incorporation have been described (Rank, U.S. published patent application No. 2008/0108082; Hanzel, U.S. published patent application No. 2007/0196846).

In some embodiments, the mutant polymerase can be selected based on the combination of the mutant polymerase and nucleotides, and the reaction conditions, used to conduct the nucleotide binding and/or nucleotide incorporation reactions.

In some embodiments, the mutant polymerases, nucleotides, and reaction conditions, can be screened for their suitability for use in the nucleotide binding and/or nucleotide incorporation methods, using well known screening techniques. For example, the suitable mutant polymerase may be capable of binding nucleotides and/or incorporating nucleotides. The reaction kinetics for nucleotide binding, association, incorporation, and/or dissociation rates, can be determined using rapid kinetics techniques (e.g., stopped-flow or quench flow techniques). Using stopped-flow or quench flow techniques, the binding kinetics of a nucleotide can be estimated by calculating the $1/k_{pol}$ value. Stopped-flow techniques that analyze absorption and/or fluorescence spectroscopy properties of the nucleotide binding, incorporation, or dissociation rates to a polymerase are well known in the art (Kumar and Patel 1997 Biochemistry 36:13954-13962; Tsai and Johnson 2006 Biochemistry 45:9675-9687; Hanzel, U.S. published patent application No. 2007/0196846). Other methods include quench flow (Johnson 1986 Methods Enzymology 134:677-705), time-gated fluorescence decay time measurements (Korlach, U.S. Pat. No. 7,485,424), plate-based assays (Clark, U.S. published patent application No. 2009/0176233), and X-ray crystal structure analysis (Berman 2007 EMBO Journal 26:3494). Nucleotide incorporation by a mutant polymerase can also be analyzed by gel separation of the primer extension products. In one embodiment, stopped-flow techniques can be used to screen and select combinations of nucleotides (including labeled nucleotide analogs) with polymerases having a $t_{pol}$ value (e.g., $1/K_{pol}$) which is less than a $t_{-1}$ (e.g., $1/k_{-1}$) value. Stopped-flow techniques for measuring $t_{pol}$ (MP Roettger 2008 Biochemistry 47:9718-9727; M Bakhtina 2009 Biochemistry 48:3197-320) and $t_{-1}$ (M Bakhtina 2009 Biochemistry 48:3197-3208) are known in the art. An exemplary stopped-flow assay for characterizing the duration of nucleotide-binding to a polymerase is provided herein in Example 2; however, any other suitable assay can also be employed.

In some embodiments, the selection of the mutant polymerase may be determined by the level of processivity desired for conducting nucleotide incorporation or polymerization reactions. The mutant polymerase processivity can be gauged by the number of nucleotides incorporated for a single binding event between the mutant polymerase and the target molecule base-paired with the polymerization initiation site. For example, the processivity level of the mutant polymerase may be about 1, 5, 10, 20, 25, 50, 100, 250, 500, 750, 1000, 2000, 5000, or 10,000 or more nucleotides incorporated with a single binding event (i.e., binding a template molecule). Processivity levels typically correlate with read lengths of a polymerase.

In some embodiments, the selection of the mutant polymerase may be determined by the level of fidelity desired, such as the error rate per nucleotide incorporation. The fidelity of a mutant polymerase may be partly determined by the 3'→5' exonuclease activity associated with the mutant DNA polymerase. The fidelity of a mutant DNA polymerase may be measured using assays well known in the art (Lundburg et al., 1991 Gene, 108:1-6). The error rate of the mutant polymerase can be one error per about 100, or about 250, or about 500, or about 1000, or about 1500 incorporated nucleotides. High fidelity polymerases include those exhibiting error rates of about $5 \times 10^{-6}$ per base pair or lower rates.

In some embodiments, the selection of the mutant polymerase may be determined by the rate of nucleotide incorporation such as about one nucleotide per 2-5 seconds, or about one nucleotide per second, or about 5 nucleotides per second, or about 10 nucleotides per second, or about 20 nucleotides per second, or about 30 nucleotides per second, or more than 40 nucleotides per second, or more than 50-100 per second, or more than 100 per second. In one embodiment, polymerases exhibiting reduced nucleotide incorporation rates include mutant RB69 polymerases having lysine substituted with leucine, arginine, or other amino acids (Castro 2009 Nature Structural and Molecular Biology 16:212-218).

In some embodiments, the mutant polymerase can be a deletion mutant that retains nucleotide polymerization activity but lacks the 3'→5' or 5'→3' exonuclease activity.

Fusion Proteins

In some embodiments, the mutant polymerase can be a fusion protein comprising the amino acid sequence of the nucleic acid-dependent polymerizing enzyme (or a biologically active fragment thereof) operably linked to the amino acid sequence of a second biologically active enzyme (or a biologically active fragment thereof). The second enzyme sequence may be linked to the amino or carboxyl end of the mutant polymerase sequence, or may be inserted within the mutant polymerase sequence. The mutant polymerase sequence may be linked to the amino or carboxyl end of the second enzyme sequence, or may be inserted within the second enzyme sequence. The mutant polymerase and second enzyme sequences can be linked to each other in a manner that does not interfere with polymerase activity or with a nucleotide binding to the polymerase or with nucleotide polymerization, or does not interfere with the activity of the second enzyme sequence. The fusion protein can include the amino acid sequences of the mutant polymerase chemically linked to the amino acid sequence of the second enzyme.

Tagged Polymerases

In some embodiments, the mutant polymerase can be operably linked to a linker moiety includes: a covalent or non-covalent bond; amino acid tag (e.g., poly-amino acid tag, poly-His tag, 6His-tag); chemical compound (e.g., polyethylene glycol); protein-protein binding pair (e.g., biotin-avidin); affinity coupling; capture probes; or any combination of these. The linker moiety can be separate from or part of the mutant polymerase (e.g., recombinant His-tagged polymerase). Typically, the linker moiety does not interfere with the nucleotide binding activity, or catalytic activity of the mutant polymerase.

Mutant Polymerases Linked to Reporter Moieties

Provided herein are mutant DNA polymerases which are unlinked, or are operably linked to reporter moieties via a suitable linker. The reporter moiety can be an energy transfer donor which is capable of FRET with a proximal energy transfer acceptor. The energy transfer donor can be a fluorescent dye or nanoparticle. Typically, the reporter moiety and the suitable linker do not interfere with the function or activity of the mutant polymerases.

In some embodiments, the suitable linker can mediate covalent or non-covalent attachment. Examples of non-covalent attachment includes: ionic, hydrogen bonding, dipole-dipole interactions, van der Waals interactions, ionic interactions, and hydrophobic interactions. In particular, examples of non-covalent attachment includes: nucleic acid hybridization, protein aptamer-template binding, electrostatic interaction, hydrophobic interaction, non-specific adsorption, and solvent evaporation.

In some embodiments, the suitable linker can be rigid or flexible. The rigid linker can be used to improve a FRET signal by optimizing the orientation of the energy transfer dye. Examples of rigid linkers include benzyl linkers, proline or poly-proline linkers (S. Flemer, et al., 2008 Journal Org. Chem. 73:7593-7602), bis-azide linkers (M. P. L. Werts, et al., 2003 Macromolecules 36:7004-7013), and rigid linkers synthesized by modifying the so-called "click" chemistry scheme that is described by Megiatto and Schuster (2008 Journal of the Am. Chem. Soc. 130:12872-12873).

The suitable linker can optimize proximity, length, distance, orientation, or charge. For example, the linker can be a cationic poly-arginine spacer linker or an imidazolium spacer molecule.

In some embodiments, the suitable linker can be a cleavable, self-cleavable, or fragmentable linker. The self-cleaving linker can be a trimethyl lock or a quinone methide linker. The suitable linker can be cleaved or fragmented via light (e.g., photo-cleavable linkers), a chemical reaction, enzymatic activity, heat, acid, or base.

The suitable linker can be linear, non-linear, branched, bifunctional, trifunctional, homofunctional, or heterofunctional. Some linkers have pendant side chains or pendant functional groups, or both. The suitable linker comprises about 1-100 plural valent atoms. In some embodiments, the linker moiety comprises about 1-40 plural valent atoms, or more, selected from the group consisting of C, N, O, S and P.

Linking the Mutant Polymerases and Nanoparticles

The mutant polymerases can be operably linked to at least one nanoparticle using well known linking schemes. In general, these linking schemes include: (1) a condensation reaction between the amines on the proteins and the carboxy groups on the nanoparticle using, for example, 1-ethyl-3-(3-dimethylaminopropyl) carbodiimide (EDC); (2) directly binding thiolated proteins to the nanoparticles using dative thiol-bonding between the cysteine residues on the protein and the sulfur atoms on the nanoparticle surface; (3) metal-affinity coordination between the histidine residues in the proteins and the Zn atoms on the nanoparticle surface; or (4) adsorption or non-covalent self-assembly of protein (e.g., mutant polymerase) on to the nanoparticle surface.

In some embodiments, the nanoparticles can have ligand coatings, such as carboxyl groups (e.g., as carboxyl-derived amphiphilic compounds) which can be reacted with the amines, hydrazines, or hydroxylamines on the mutant polymerases in a condensation reaction (e.g., using EDC).

The nanoparticle ligands can be amino-derivatized ligands that permit crosslinking with amine reactive groups such as isothiocyanates, succinimidyl esters and other active esters.

The mutant polymerases can be attached directly to the nanoparticle. The mutant polymerases having a poly-His sequence (e.g., tag) can be attached directly to a nanoparticle via metal-affinity coordination between the nanoparticle Zn atoms (e.g., on the shell) and histidine residues. The histidine residues also have varying affinities for other metals including $Ni^{2+}$, $Co^{2+}$, $Cu^{2+}$, $Mn^{2+}$, $Fe^{2+}$ and $Fe^{3+}$. The mutant polymerases can be attached directly to the nanoparticle via dative thiol bonding between S atoms in the nanoparticle and cysteine residues on the surface or in the protein.

In some embodiments, the mutant polymerases can adsorb (e.g., non-covalently) on to the nanoparticle. For example, positively charged polymerases can adsorb on to the negatively charged a nanoparticle.

The nanoparticle ligand coating can be PEG or biotin, which can be linked to the mutant polymerase having an avidin-like molecule, via amine linking chemistry. For example, the PEG coating can be reacted with a cross-linker (e.g., bis(sulfosuccinimidyl) suberate; (BS3)) for amine linking with streptavidin.

In some embodiments, the nanoparticle can be reacted with a compound which can bind to some or all of the binding sites on the nanoparticle shell in order to mask the binding sites. The compounds include horseradish peroxidase (HRP), glutathione S-transferase (GST), uracil-DNA glycosylase (UDG), uracil glycosylase inhibitor (UGI), or bovine serum albumin (BSA). For example, a non-masked nanoparticle may be capable of binding many protein molecules. In another example a partially masked nanoparticle, which is coated with HRP, GST, UDG, UGI, and/or BSA, may be capable of binding fewer protein molecules. In one embodiment, one nanoparticle can bind about 1-5, or about 5-10, or about 10-20, or about 20-50, or more mutant polymerases. In one embodiment, one nanoparticle can bind one mutant polymerase.

In one embodiment, the nanoparticle can be reacted to carry an iodoacetal functional group which can bind to a mutant polymerase carrying a phosphorothioate functional group on a recombinantly introduced serine residue.

Dispersibility of Nanoparticles

The nanoparticles can be reacted with compounds that alter the dispersibility properties of the nanoparticles, or form reactive groups for covalent or non-covalent interactions with the mutant polymerases.

In one aspect, the nanoparticles can be modified to permit dispersibility in a solvent. For example, the nanoparticles can be dispersible in aqueous solvents, including: water, and aqueous solutions and buffers. Nanoparticles that are not dispersible in aqueous solvents typically have hydrophobic ligands which are intimately associated with the outer shell. The ligands, which are sometimes referred to as a cap, can be trioctylphosphine (TOP), trioctylphosphine oxide (TOPO), oleic acid, or tetradecylphosphonic acid (TDPA). The aqueous-dispersible nanoparticles can be modified to have hydrophilic ligands via a cap exchange procedure. The cap exchange procedure can involve substituting the exposed groups on the nanoparticle (e.g., hydrophobic caps) with heterofunctional ligands. The nanoparticle surface can be modified to have hydrophilic ligands by encapsulating the nanoparticle in a coating of heterofunctional ligands. The heterofunctional ligands can include a thiol anchor moiety and a hydrophilic moiety (e.g., hydroxyl or carboxyl). Examples of heterofunctional ligands include thiol and phosphine mono and multidentate ligands, such as: mercaptocarbonic acids; alkylhiol terminated molecules, thioalkylated molecules, and dihydrolipoic acid derivatives. Another example involves forming a polymerized silica shell on the nanoparticle surface. The silica shell can be functionalized with polar groups using, for example, mercaptopropyl silanols or amine box dendrimers. In yet another example, the native functional groups on the nanoparticle surface are preserved. The nanoparticles are reacted with amphiphilic diblock or triblock copolymers, or phospholipids, which have hydrophobic groups that interdigitate with the native functional groups on the nanoparticle shell. The amphiphilic copolymers and have hydrophilic groups that permit aqueous dispersal. The interdigitating compounds include: phosphatidylethanol amine, phosphatidycholine micelles, modified acrylic acid polymers, poly (maleic anhydride)-alt-1-tetradecene, amphiphilic triblock copolymer (Gao 2004 Nature Biotechnology 22:969-976), and amphiphilic saccharides. Another procedure for preserving the nanoparticle native functional groups involves reacting the nanoparticle with oligomeric phosphines that carry hydrophilic functional groups and/or carry a protein-protein binding partner (e.g., avidin or derivative thereof). Proteins can also be nonspecifically adsorbed on to the nanoparticle surface.

Mutant RB69 Polymerase Sequences

In some embodiments, the mutant RB69 polymerases of the present disclosure can exhibit reduced exonuclease activity. For example, the mutant polymerase can include mutations at (in single letter amino acid code): D222A, D327A, or D222A/D327A (numbering is based on the amino acid sequence shown in SEQ ID NOS:1 or 2).

In some embodiments, the mutant RB69 polymerases of the present disclosure can exhibit an enhanced ability to incorporate nucleotides (Gardner and Jack 1999 Nucleic Acids Research 27:2545-2555; Gardner and Jack 2002 Nucleic Acids Research 30:605-613), including dideoxynucleotides (N558L, Y416A, or N558L/Y416A), acyclonucleotides (N558L), 3' modified nucleotides including 3' azido-modified nucleotides (LYP amino acid motif at positions 415-417 mutated to SAV), and ribonucleotides (Y416A, N558L/Y416A), and other modifications (N558L, or LYP amino acid motif at positions 415-417 mutated to SAV) (numbering is based on the amino acid sequence shown in SEQ ID NO:1).

In some embodiments, the mutant RB69 polymerase can include any one or more mutations selected from the group consisting of: D222A; D327A; L415S; Y416A; P417V; N558L; D22A/D327A; D222A/D327A/N558L; D22A/D327A/Y416A; D222A/D327A/N558L/Y416A; D222A/D327A/L415S/Y416A/P417V; and D222A/D327A/N558L/L415S/Y416A/P417V, wherein the numbering is based on the amino acid sequence shown in SEQ ID NO:1).

For example, the mutant RB69 polymerases can include any one of the mutant polymerases listed in Table 1 below.

TABLE 1

| | | | | |
|---|---|---|---|---|
| WT | 6HIS-tag | | | |
| SX | 6HIS-tag | D327A | | |
| DX | | D222A, D327A | | |
| FDX | | D222A, D327A | N558L | |
| PDX | | D222A, D327A | | Y416A |
| FPDX | | D222A, D327A | N558L | Y416A |
| 3PDX | | D222A, D327A | | | 415LYP > SAV |
| F3PDX | | D222A, D327A | N558L | | 415LYP > SAV |

Also provided herein are any nucleotide sequences that encode the mutant RB69 polymerases of the present disclosure. It is well known in the art that the genetic code is degenerate. Accordingly, more than one triplet codon can encode the same amino acid. Table 2 below illustrates the degenerate genetic code.

TABLE 2

| Amino Acid | Symbol | Symbol | Codons |
|---|---|---|---|
| Alanine | Ala | A | GCU, GCC, GCA, GCG |
| Cysteine | Cys | C | UGU, UGC |
| Aspartic Acid | Asp | D | GAU, GAC |
| Glutamic Acid | Glu | E | GAA, GAG |
| Phenylalanine | Phe | F | UUU, UUC |
| Glycine | Gly | G | GGU, GGC, GGA, GGG |
| Histidine | His | H | CAU, CAC |
| Isoleucine | Ile | I | AUU, AUC, AUA |
| Lysine | Lys | K | AAA, AAG |
| Leucine | Leu | L | UUA, UUG, CUU, CUC, CUA, CUG |
| Methionine | Met | M | AUG |
| Asparagine | Asn | N | AAU, AAC |
| Proline | Pro | P | CCU, CCC, CCA, CCG |
| Glutamine | Gln | Q | CAA, CAG |
| Arginine | Arg | R | CGU, CGC, CGA, CGG, AGA, AGG |
| Serine | Ser | S | UCU, UCC, UCA, UCG, AGU, AGC |

TABLE 2-continued

| Amino Acid | Symbol | Symbol | Codons |
|---|---|---|---|
| Threonine | Thr | T | ACU, ACC, ACA, ACG |
| Valine | Val | V | GUU, GUC, GUA, GUG |
| Tryptophan | Trp | W | UGG |
| Tyrosine | Tyr | Y | UAU, UAC |

In one embodiment, the mutant DNA polymerases comprise amino acid sequences of about 80%, 85%, 90%, 95%, 97%, 98% or 99% identical to any one of the amino acid sequences of SEQ ID NOS:2-8. In some embodiments, these mutant DNA polymerases can exhibit altered, e.g., increased or decreased, ability to transiently-bind a labeled nucleotide relative to the binding capability of a wild type RB69 polymerase according to SEQ ID NO: 1. In some embodiments, these mutant DNA polymerases can exhibit altered, e.g., increased or decreased, ability to incorporate a nucleotide (e.g., a labeled nucleotide or terminator nucleotide) relative to a wild type RB69 polymerase having the amino acid sequencing of SEQ ID NO: 1.

In another embodiment, the mutant DNA polymerase can exhibit exonuclease activity. In some embodiments, the mutant DNA polymerase can exhibit reduced exonuclease activity relative to the RB69 polymerase having the amino acid sequence of SEQ ID NO: 1. For example, the mutant DNA polymerases can exhibit exonuclease activity, and comprise an aspartic acid (D) at position 222 and/or an aspartic acid (D) at position 327 as shown in any one of SEQ ID NO:1-8. In another example, the mutant DNA polymerase can exhibit reduced exonuclease activity relative to the wild type RB69 polymerase having the amino acid sequence of SEQ ID NO: 1, and can further comprise an alanine (A) at position 222 and/or an alanine (A) at position 327 as shown in any one of SEQ ID NO:1-8. Optionally, the mutant DNA polymerase can comprise further modifications (e.g., amino acid substitution(s)) at any other position of any one of SEQ ID NO:1-8.

In some embodiments, the mutant polymerase comprises the amino acid sequence that is at least 80%, 85%, 90%, 95%, 97% or 99% identical to any amino acid sequence selected from the group consisting of: SEQ ID NO: 1, SEQ ID NO: 2, SEQ ID NO:3, SEQ ID NO:4, SEQ ID NO:5, SEQ ID NO:6, SEQ ID NO:7, and SEQ ID NO:8. Optionally, the mutant polymerase can exhibit increased duration of binding to a labeled nucleotide relative to a wild type RB69 polymerase having the amino acid. In some embodiments, the duration of nucleotide binding can be estimated using a stopped-flow assay as described, for example, in Example 2; alternatively, any other suitable assay for measuring the duration of nucleotide binding can be used. Optionally, the mutant polymerase can exhibit increased nucleotide incorporation activity for a labeled nucleotide and/or for a terminator nucleotide. In some embodiments, the nucleotide incorporation activity can be measured using the assay procedure described in Example 3; alternatively, any other suitable assay for measuring nucleotide incorporation activity can be used.

Nucleotides

The mutant DNA polymerases can transiently-bind and/or incorporate a nucleotide. In one aspect, nucleotides are compounds that can bind selectively to, or can be incorporated by, the mutant polymerases provided herein. Such nucleotides include not only naturally-occurring nucleotides but also any analogs, regardless of their structure, that can bind selectively to, or can be polymerized by, the mutant polymerase. While naturally-occurring nucleotides typically comprise base, sugar and phosphate moieties, the nucleotides of the present disclosure can include compounds lacking any one, some or all of such moieties.

In some embodiments, the nucleotides can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In one embodiment, the phosphorus atoms in the chain can have side groups having O, $BH_3$, or S. In the phosphorus chain, a phosphorus atom with a side group other than 0 can be a substituted phosphate group. Some examples of nucleotides are described in Xu, U.S. Pat. No. 7,405,281. Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof.

In some embodiments, the nucleotides can be operably linked to a reporter moiety (e.g., labeled nucleotides) or can be un-labeled. The reporter moiety can be operably linked to any part of the nucleotide, including the base, sugar or to any phosphate group or substitute phosphate group (e.g., a terminal phosphate group, or any other phosphate group that is released from the nucleotide during incorporation by the polymerase).

Typically, the reporter moiety generates, or causes to be generated, a detectable signal. Any suitable reporter moiety may be used, including luminescent, photoluminescent, electroluminescent, bioluminescent, chemiluminescent, fluorescent, phosphorescent, chromophore, radioisotope, electrochemical, mass spectrometry, Raman, hapten, affinity tag, atom, or an enzyme. The reporter moiety generates a detectable signal resulting from a chemical or physical change (e.g., heat, light, electrical, pH, salt concentration, enzymatic activity, or proximity events). A proximity event includes two reporter moieties approaching each other, or associating with each other, or binding each other. For example, proximity of an energy transfer donor and acceptor moiety can occur when an acceptor-labeled nucleotide binds the active site of a donor-labeled mutant polymerase, resulting in energy transfer from the donor to the acceptor. In one embodiment, energy transfer distances (e.g., FRET distances) can be about 5-20 nm. The reporter moieties may be selected so that each absorbs excitation radiation and/or emits fluorescence at a wavelength distinguishable from the other reporter moieties to permit monitoring the presence of different reporter moieties in the same reaction. Two or more different reporter moieties can be selected having spectrally distinct emission profiles, or having minimal overlapping spectral emission profiles.

The fluorescent moiety includes: rhodols; resorufins; coumarins; xanthenes; acridines; fluoresceins; rhodamines; erythrins; cyanins; phthalaldehydes; naphthylamines; fluorescamines; benzoxadiazoles; stilbenes; pyrenes; indoles; borapolyazaindacenes; quinazolinones; eosin; erythrosin; and Malachite green.

Terminator Nucleotides

In some embodiments, the mutant DNA polymerases can transiently bind and/or incorporate a terminator nucleotide. Optionally, the terminator nucleotides can be incorporated in a template-dependent manner by the mutant polymerase. In some embodiments, the incorporated terminator nucleotide can inhibit the subsequent incorporation of another nucleotide by the polymerase.

In some embodiments, the terminator nucleotide comprises a nucleotide operably linked to an inhibitor moiety. Typically, the inhibitor moiety can comprise any chemical compound or chemical group which permits incorporation of the terminator nucleotide by the mutant polymerase but inhibits incorporation of the next nucleotide. Thus, the mutant polymerase can incorporate one and only one terminator nucleotide, thereby advancing nucleotide incorporation by only one base. The inhibitor moiety can be operably linked to any portion of the nucleoside or nucleotide (e.g., any phosphate group, or base or sugar moiety). The same type or different types of inhibitor moieties can be operably linked to different types of nucleotides. The terminator nucleotide can be resistant to degradation by 3'-5' exonuclease activity of the mutant polymerase.

On the terminator nucleotide, the inhibitor moiety can be modified following incorporation of the terminator nucleotide so that the next nucleotide can be incorporated (e.g., reversible terminator nucleotide). Alternatively, the inhibitor moiety can be cleaved off or otherwise removed following incorporation (de-blocking) to permit incorporation of the next nucleotide.

In one embodiment, the terminator nucleotides can be non-labeled, or can be operably linked to at least one reporter moiety at any position of the base or sugar, or any of the phosphate groups (alpha, beta, gamma, or terminal phosphate group).

Many suitable terminator nucleotides having inhibitor moieties attached to the sugar 3' position, base-linked dyes, where the linkers are cleavable under the same conditions are described by Tsien (WO/1991/006678). Additionally, suitable terminator nucleotides having photocleavable linkers are described by Stemple (U.S. Pat. No. 7,270,951; Turner, U.S. Pat. No. 7,476,504).

Inhibitor Moieties

The terminator nucleotides can optionally comprise a nucleotide operably linked to at least one suitable inhibitor moiety. In some embodiments, the inhibitor moiety comprises any chemical compound or chemical group which permits polymerization, in a template-dependent manner, by the mutant polymerase, but inhibits incorporation of the next nucleotide. The inhibitor moiety can modify, substitute, or protect, any portion of the nucleotide (e.g., base, sugar, or phosphate group). A suitable inhibitor moiety can be operably linked to any part of the nucleotide (or nucleoside) including the base or sugar moiety, or any phosphate group, or any analogous structure corresponding to any of these moieties.

In some embodiments, the suitable inhibitor moiety can permit incorporation of the terminator nucleotide, in a polymerase-driven, template-dependent manner, but inhibits, stalls, or slows down incorporation of the next nucleotide by the mutant polymerase. In some embodiments, the suitable inhibitor moiety inhibits incorporation of the next nucleotide by physical, chemical, or charge interaction with the mutant polymerase and/or incoming nucleotide.

The suitable inhibitor moiety can be operably linked to the 2' or 3' position of the sugar moiety. In one embodiment, the 2' or 3' —H or —OH group of the sugar moiety can be modified, substituted, or protected. For example, it is well known that DNA polymerases can require a polymerization initiation site having a terminal 3' —OH group. Thus, the inhibitor moiety can be any chemical group or compound, which is not an —OH group, operably linked to the 3' C of the sugar moiety or analogous structure within the nucleotide. In some embodiments, the suitable inhibitor moiety can be an —H group operably linked to the 3' C of the sugar moiety or analogous structure within the nucleotide. Such embodiments include dideoxynucleosides and dideoxynucleotides. Examples of inhibitor moieties attached to the sugar 3' position are described by Balasubramanian (U.S. Pat. No. 7,427,673) and Milton (U.S. Pat. No. 7,541,444).

The suitable inhibitor moiety can be operably linked to any position of the nitrogenous base, such as a purine group or analogous structure within the nucleotide, including the C2, C4, C5, N3, or C6, of cytosine, thymine, and uracil, or to any analogous structure in the nucleotide. The suitable inhibitor moiety can be operably linked to any position of the pyrimidine group or analogous structure within the nucleotide, including the C2, C6, C8, N3 and N7 of adenine and guanine.

The suitable inhibitor moiety can be operably linked to any phosphate group or analogous structure within the nucleotide, such as the alpha, beta or gamma phosphate group, the terminal phosphate group, or any other phosphate group that is released upon incorporation.

In some embodiments, the suitable inhibitor moiety can be linked to any portion of the nucleoside or nucleotide, and sterically hinder the incoming nucleotide. In some embodiments, the suitable inhibitor moiety can be a charged group (positive or negative) and linked to any portion of the nucleoside or nucleotide and can inhibit the polymerase from incorporating the next nucleotide. In some embodiments, the suitable inhibitor moiety can be linked to at least one of: a sterically-hindering group, fluorophore, and/or quencher, in any order and in any combination.

In some embodiments, the suitable inhibitor moiety comprises any group including: amine, alkyl, alkenyl, alkynyl, alkyl amide, aryl, ether, ester, benzyl, propargyl, propynyl, phosphate, or analog thereof. For example, the suitable inhibitor moiety can be a 3'-O-allyl moiety (Ruparel, et al., 2005 Proc. Natl. Acad. Sci. USA 102:5932-5937).

Suitable inhibitor moieties are well known in the art, and include: fluorenylmethyloxycarbonyl (FMOC), 4-(anisyl) diphenylmethyltrityl (MMTr), dimethoxytrityl (DMTr), monomethoxytrityl, trityl (Tr), benzoyl (Bz), isobutyryl (ib), pixyl (pi), ter-butyl-dimethylsilyl (TBMS), and 1-(2-fluorophenyl)-4-methoxypiperidin 4-yl (FPMP). See also T W Greene 1981, in "Protective Groups in Organic Synthesis", publishers Wiley-Interscience; Beaucage and Iyer 1992 Tetrahedron, 48:2223-2311; Beaucage and Iyer 1993 Tetrahedron 49:10441-10488; and Scaringe et al., 1998 J. Am. Chem. Soc. 120:11820-11821.

In some embodiments, the suitable inhibitor moiety can be a reporter moiety (e.g., fluorescent dye) operably linked to the base or sugar moiety. For example, a fluorescent dye operably linked to the base via a 2-nitrobenzyl group, where the 2-nitrobenzyl group has the alpha carbon substituted with one alkyl or aryl group (Wu, et al., U.S. published patent application No. 2008/0132692). The 2-nitrobenzyl group can be photocleavable.

In another example, the suitable inhibitor moiety can be a reporter moiety (e.g., fluorescent dye, e.g., ALEXA FLUOR 549) operably linked to the 5 position of pyrimidines or the 7 position of the purines, via a cleavable disulfide linker (Turcatti, et al., 2008 Nucleic Acids Research vol. 36, No. 4, doi:10.1093/nar/gkn021).

In yet another example, the suitable inhibitor moiety can be a rhodamine-type dyes, such as R6G, R110, ROX, or TAMRA, or dichloro-derivatives thereof, which are based-linked dyes, including the commercially-available rhodamine dye terminator nucleotides from Applied Biosystems.

In some embodiments, the suitable inhibitor moiety can be a charged group (positive or negative) or a group capable of becoming charged (Efcavitch, U.S. published patent application No. 2009/0061437), including a carboxylic acid, carboxylated, phosphate, di-phosphate, peptide, dipeptide, sulfate, disulfate, caproic acid, or amino acid (e.g., a negatively charged amino acid such as aspartic acid, glutamic acid, histidine, lysine, or arginine).

In some embodiments, the suitable inhibitor moiety can be a non-incorporatable nucleotide or nucleoside which is linked to the base by a tether. The tether can be linked to a fluorescent label. The tether can include a cleavable moiety, such as a disulfide group (Siddiqi, U.S. published patent application No. 2008/0103053 and 2008/0227970).

In some embodiments, the suitable inhibitor moiety can be a hydrocaryldithiomethyl-modified compound (Kwiatkowski, U.S. Pat. No. 7,279,563.

The suitable inhibitor moiety can include an ethyl dithio linker (Siddiqi, U.S. published patent application No. 2008/0269476).

In some embodiments, the suitable inhibitor moiety can be an alkyl chain homologue having any chain length, which can be produced by replacing 2-bromoethanol and ethylsulfide reagents with any alkyl chain homologue (Siddiqi, U.S. published patent application No. 2008/0269476).

In some embodiments, the suitable inhibitor moiety can be any phosphate, $SO_3$, or C(O)R group, or modified groups thereof (Lee, U.S. published patent application No. 2008/0050780). In the C(O)R group, R can be an H, alkyl, benzyl, aryl, alkenyl, alkynyl group, any combination thereof.

In one embodiment, removal or modification of the inhibitor moiety which is attached to the 3' C of the sugar moiety, and restoration of a 3' —OH group, can permit incorporation of a subsequent nucleotide (e.g., reversible terminator nucleotide). In another embodiment, removal or modification of the inhibitor moiety which is attached to the sugar, base, or phosphate group, can permit incorporation of a subsequent nucleotide (e.g., reversible terminator nucleotide).

Linkers for Terminator Nucleotides

In some embodiments, the terminator nucleotide is operably linked to the inhibitor moiety via a suitable linker. Typically, the suitable linker does not interfere with the function or activity of the nucleotide, nucleoside, or inhibitor moiety. The suitable linker can be cleavable or fragmentable to permit removal of the inhibitor moiety. The suitable linker can be the inhibitor moiety. In one embodiment, the nucleotide can be attached directly to the inhibitor moiety without an intervening linker. Various linkers and linker chemistries for generating the terminator nucleotides are disclosed infra.

Optionally, the terminator nucleotides can be linked to inhibitor moieties using any suitable linking scheme, including linking schemes using amine linkers (Hobbs, U.S. Pat. No. 5,151,507), or primary or secondary amines, or a rigid hydrocarbon arm (RF Service, 1998 Science 282:1020-21).

Optionally, the terminator nucleotide can include more than one linker, where the linkers are the same or different. The multiple linkers can be removed, cleaved or fragmented using different temperatures, enzymatic activities, chemical agents, and/or different wavelengths of electromagnetic radiation.

Cleavable Linkers

In some embodiments, the linker that links the inhibitor moiety to the terminator nucleotide can be cleavable by heat, enzymatic activity, chemical agent, or electromagnetic radiation. Cleavable groups include: disulfide, amide, thioamide, ester, thioester, vicinal diol, or hemiacetal. Other cleavable bonds include enzymatically-cleavable bonds, such as peptide bonds (cleaved by peptidases), phosphate bonds (cleaved by phosphatases), nucleic acid bonds (cleaved by endonucleases), and sugar bonds (cleaved by glycosidases).

In one embodiment, the cleavable linker can be a photocleavable linker, such as a 2-nitrobenzyl linker (Bai 2004 Nucl. Acid Res. 32:535-541; Seo, et al., 2005 Proc. Natl. Acad. Sci. USA 102:5926-5931; Wu, et al., 2007 Proc. Natl. Acad. Sci. USA 104:16462-16467), or others (Lyle, U.S. published patent application No. 2008/0009007). Analogs of the 2-nitrobenzyl linker, and other photocleavable linkers can be used as cleavable blocking groups, including: 2-nitrobenzyloxycarbonyl (NBOC); nitroveratryl; 1-pyrenylmethyl; 6-nitroveratryloxycarbonyl (NVOC); dimethyldimethoxybenzyloxycarbonyl (DDZ); 5-bromo-7-nitroindolinyl; O-hydroxy-alpha-methyl-cinnamoyl; methyl-6-nitroveratryloxycarbonyl; methyl-6-nitropiperonyloxycarbonyl; 2-oxymethylene anthraquinone; dimethoxybenzyloxy carbonyl; 5-bromo-7-nitroindolinyl; O-hydroxy-alpha-methyl cinnamoyl; t-butyl oxycarbonyl (TBOC), and 2-oxymethylene anthriquinone (see: McGall, U.S. Pat. No. 5,412,087; Pirrung, U.S. Pat. No. 5,143,854; and Conrad, U.S. Pat. No. 5,773,308). The photocleavable linkers can be illuminated with an electromagnetic source at about 320-800 nm, depending on the particular linker, to achieve cleavage. For example, 1-(2-nitrophenyl)ethyl can be cleaved with light at about 300-350 nm, and 5-bromo-7-nitroindolinyl can be cleaved with light at about 420 nm. In another embodiment, the photocleavable linker can serve as the inhibitor moiety.

In another embodiment, the terminator nucleotide can include two or more cleavable linkers, each attached to a different portion of the nucleotide. For example, the terminator nucleotide can include two different photo-cleavable linkers that are cleavable with the same or different wavelengths of light.

In another embodiment, the linker can be an ethyl dithio or an alkyl chain linker (Siddiqi, U.S. published patent application Nos. 2008/0269476 and 2008/0286837). In another embodiment, the cleavable linker can be a disulfide-linker which is a chemically-cleavable linker (Shimkus 1985 Proc. Natl. Acad. Sci. USA 82:2593-2597). In yet another embodiment, the cleavable linker can be an allyl moiety which is cleavable by palladium (Pd(0)) in a deallylation reaction (Ju, et al., 2006 Proc. Natl. Acad. Sci. USA 103:19635-19640; Wu, et al., 2007 Proc. Natl. Acad. Sci. USA 104:16462-16467), or an azidomethyl group which is cleavable with Tris(2-carboxyethyl)phosphine (TCEP) in aqueous solution (Guo, et al., 2008 Proc. Natl. Acad. Sci. USA 105:9145-9150; Bentley, et al., 2008 Nature 456:53-59, and Supplemental Materials and Methods). In still another embodiment, the linker can be cleavable with silver nitrate ($AgNO_3$). In another embodiment, an azidomethyl group can serve as an inhibitor moiety and a cleavable linker.

A procedure for synthesizing a terminator nucleotide having an unblocked 3'OH group and carrying a biotin molecule linked to the base moiety (N6-alkylated base) via a 2-nitrobenzyl linker may be adapted from the method described by Wu (Nucl. Acid. Res. 2007, 35:6339-6349).

Fragmentable Linkers

In some embodiments, the inhibitor moiety is linked to the terminator nucleotide via a suitable fragmentable linker. Optionally, the suitable fragmentable linker is capable of fragmenting in an electronic cascade self-elimination reaction (Graham, U.S. published patent application No. 2006/0003383; and Lee, U.S. published patent application No. 2008/0050780). In some embodiments, the fragmentable linker comprises a trigger moiety. The trigger moiety comprises a substrate that can be cleaved or "activated" by a specified trigger agent. Activation of the trigger moiety initiates a spontaneous rearrangement that results in the fragmentation of the linker and release of the enjoined compound. For example, the trigger moiety can initiate a ring closure mechanism or elimination reaction. Various elimination reactions, include 1,4-, 1,6- and 1,8-elimination reactions.

Any means of activating the trigger moiety may be used. Selection of a particular means of activation, and hence the trigger moiety, may depend, in part, on the particular fragmentation reaction desired. In some embodiments, activation is based upon cleavage of the trigger moiety. The trigger moiety can include a cleavage site that is cleavable by a chemical reagent or enzyme. For example, the trigger moiety can include a cleavage recognition site that is cleavable by a sulfatase (e.g., $SO_3$ and analogs thereof), esterase, phosphatase, nuclease, glycosidase, lipase, esterase, protease, or catalytic antibody.

Non-Incorporatable Nucleotides

In some embodiments, the mutant DNA polymerases can transiently-bind a non-incorporatable nucleotide. The non-incorporatable nucleotides may or may not have a structure similar to that of a native nucleotide which may include base, sugar, and phosphate moieties.

Optionally, the non-incorporatable nucleotides can bind the polymerase/template complex in a template-dependent manner, or can act as a universal mimetic and bind the polymerase/template complex in a non-template-dependent manner. The non-incorporatable nucleotides can be a nucleotide mimetic of incorporatable nucleotides, such as adenosine, guanosine, cytidine, thymidine or uridine nucleotides. The non-incorporatable nucleotide includes any compound having a nucleotide structure, or a portion thereof, which can bind a mutant polymerase.

For example, the non-incorporatable nucleotides can have the general structure:

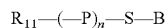

Where B can be a base moiety, such as a hetero cyclic base which includes substituted or unsubstituted nitrogen-containing heteroaromatic ring. Where S can be a sugar moiety, such as a ribosyl, riboxyl, or glucosyl group. Where n can be 1-10, or more. Where P can be one or more substituted or unsubstituted phosphate or phosphonate groups. Where $R_{11}$, if included, can be a reporter moiety (e.g., a fluorescent dye). In one embodiment, the non-incorporatable nucleotide having multiple phosphate or phosphonate groups, the linkage between the phosphate or phosphonate groups can be non-hydrolyzable by the mutant polymerase. The non-hydrolyzable linkages include, but are not limited to, amino, alkyl, methyl, and thio groups. Non-incorporatable nucleotide tetraphosphate analogs having alpha-thio or alpha boreno substitutions having been described (Rank, U.S. published patent application No. 2008/0108082; and Gelfand, U.S. published patent application No. 2008/0293071).

Optionally, the phosphate or phosphonate portion of the non-incorporatable nucleotide can have the general structure:

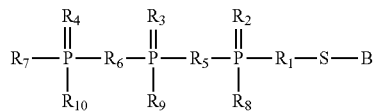

Where B can be a base moiety and S can be a sugar moiety. Where any one of the $R_1$-$R_7$ groups can render the nucleotide non-hydrolyzable by a polymerase (e.g., the mutant polymerase). Where the sugar C5 position can be $CH_2$, $CH_2O$, CH=, CHR, or $CH_2$. Where the $R_1$ group can be O, S, CH=, CH(CN), or NH. Where the $R_2$, $R_3$, and $R_4$, groups can independently be 0, $BH_3$, or SH. Where the $R_5$ and $R_6$ groups can independently be an amino, alkyl, methyl, thio group, or CHF, $CF_2$, CHBr, $CCl_2$, O—O, or —C≡C—. Where the $R_7$ group can be oxygen, or one or more additional phosphate or phosphonate groups, or can be a reporter moiety. Where $R_8$ can be SH, $BH_3$, $CH_3$, $NH_2$, or a phenyl group or phenyl ring. Where $R_9$ can be SH. Where $R_{10}$ can be $CH_3$, $N_3CH_2CH_2$, $NH_2$, ANS, $N_3$, MeO, SH, Ph, F, PhNH, PhO, or RS (where Ph can be a phenyl group or phenyl ring, and F can be a fluorine atom or group). The substituted groups can be in the S or R configuration.

The non-incorporatable nucleotides can be alpha-phosphate modified nucleotides, alpha-beta nucleotides, beta-phosphate modified nucleotides, beta-gamma nucleotides, gamma-phosphate modified nucleotides, caged nucleotides, or di-nucleotides.

Many examples of non-incorporatable nucleotides are known (Rienitz 1985 Nucleic Acids Research 13:5685-5695), including commercially-available ones from Jena Bioscience (Jena, Germany).

Nanoparticles

Provided herein are mutant polymerases operably linked to at least one suitable nanoparticle. The suitable nanoparticle can serve as a donor fluorophore in energy transfer reactions such as FRET. In one embodiment, a semiconductor nanoparticle can be linked to a site near the nucleotide binding site on the mutant polymerase, to facilitate energy transfer signals to/from the transiently-bound labeled nucleotides.

In one aspect, the nanoparticle can be a core/shell nanoparticle which typically comprises a core surrounded by at least one shell. For example, the core/shell nanoparticle can be surrounded by an inner and outer shell. In another aspect, the nanoparticle is a core nanoparticle which has a core but no surrounding shell. The outmost shell is typically coated with tightly associated ligands that are not removed by ordinary solvation.

The nanoparticle includes the core, shell(s), and ligand coatings. Methods for making core nanoparticles, core/shell nanoparticles, and ligand coated nanoparticles are well known in the art.

In one aspect, the nanoparticle core and shell can be made from any suitable metal and/or non-metal atoms for forming semiconductor nanoparticles. The core and shell can be composed of different semiconductor materials.

The core can be composed of a semiconductor material (including ternary and quaternary mixtures thereof), from: Groups II-VI of the periodic table, including ZnS, ZnSe, ZnTe, CdS, CdSe, CdTe, HgS, HgSe, HgTe, MgTe; Groups III-V, including GaN, GaP, GaAs, GaSb, InN, InP, InAs, InSb, AlAs, AlP, AlSb, AlS; and/or Group IV, including Ge, Si, Pb.

The shell can be composed of materials (including ternary and quaternary mixtures thereof) comprising: ZnO, ZnS, ZnSe, ZnTe, CdO, CdS, CdSe, CdTe, MgS, MgSe, GaAs, GaN, GaP, GaAs, GaSb, HgO, HgS, HgSe, HgTe, InAs, InN, InP, InSb, AlAs, AlN, AlP, or AlSb. The nanoparticle may be a doped metal oxide nanoparticle.

In one aspect, the dimensions of the nanoparticle can be, in their largest dimensions, about 50-100 nm, about 40-50 nm, about 30-40 nm, about 20-30 nm, about 15-20 nm, about 10-15 nm, about 5-10 nm, or about 1-5 nm.

In one aspect, the nanoparticles can have different shapes, each of which has distinctive properties including spatial distribution of the surface charge; orientation dependence of polarization of the incident light wave; and spatial extent of the electric field. The shapes include spheres, rods, discs, triangles, nanorings, nanoshells, tetrapods, nanowires and so on.

In one aspect, the nanoparticle can be a semiconductor nanoparticle having size-dependent optical and electronic properties. For example, the nanoparticle can emit a fluorescent signal in response to excitation energy. The spectral emission of the nanoparticle can be tunable to a desired energy by selecting the particle size, size distribution, and/or composition of the semiconductor nanoparticle. For example, depending on the dimensions, the semiconductor nanoparticle can be a fluorescent nanoparticle that emits light in the UV-visible-IR spectrum. The shell material can have a bandgap greater than the bandgap of the core material. Nanoparticles are available In another aspect, the nanoparticle can be a fluorescent nanoparticle. The nanoparticles can be excited by an electromagnetic source such as a laser beam, or multi-photon excitation, or electrical excitation. The excitation wavelength can range between 190-800 nm including all values and ranges there between. The signal emitted by the nanoparticle can be between about 400-800 nm. In certain aspects, the nanoparticle can be excited by an energy source having a wavelength of about 405 nm. In other aspects, in response to excitation, the nanoparticles can emit a fluorescent signal at about 605 nm.

As with common energy transfer donors, the efficiency of energy transfer (e.g., FRET) of a nanoparticle can depend sharply upon the donor-acceptor distance R as $1/R^6$. The distance where FRET efficiency is 50% is termed $R_0$, also known as the Förster distance. $R_0$ is unique for each donor-acceptor combination and may be 5 to 10 nm. For nanoparticles that are size-tuned to emit in the visible light spectrum, the radius from the nanoparticle's energy transferring core to its surface typically ranges from 2 to 5 nm. Given typical $R_0$ distances of 5-10 nm, this means that acceptor chromophores must be within a few nanometers of the nanoparticle surface for efficient FRET between donor-acceptor pairs.

Various types of core-shell nanoparticles are commercially-available. For example, InP/ZnS, CdS, CdSe, CdSe/ZnS, and D-dots™ are available from NN-Labs. CdSe/ZnS Lumidots™ are available from Aldrich Materials Science in collaboration with Nanoco Technologies. Aggregated nanoparticles, such as TriLite™ nanoclusters containing about 8-12 individual nanoparticles are available from Crystal Plex. These nanoclusters are 40-50 nm in size and are functionalized on the surface with carboxyl groups. Various QDOTS conjugated with streptavidin that emit light in the range of about 525-800 nm, as well as several biotin-labeled QDOTS are available from Invitrogen. Also, Qdot™ ITK™ nanoparticles that have an amphiphilic polymer coating and functionalized surface chemistry (carboxyl, amino-PEG, and organic soluble groups) for custom conjugation to any desired molecule, are available from Invitrogen.

Other types of nanoparticles can be used. One example includes nanoparticles comprising a multi-shell layered core which is achieved by a sequential shell material deposition process, where one shell material is added at a time, to provide a nanoparticle having a substantially uniform shell of desired thickness that is substantially free of defects. The nanoparticles can be prepared by sequential, controlled addition of materials to build and/or applying layers of shell material to the core. The methods can include at least one coordinating solvent. See e.g., U.S. provisional applications 61/108,425, Treadway, et al., filed Oct. 24, 2008, and 61/144,613, Treadway, et al., filed Jan. 14, 2009.

In one aspect, at least one coordinating solvent can be a trialkylphosphine, a trialkylphosphine oxide, phosphonic acid, or a mixture of these. In another aspect, at least one coordinating solvent comprises trioctylphosphine (TOP), trioctylphosphine oxide (TOPO), tetradecylphosphonic acid (TDPA), or a mixture of these. In yet another aspect, the coordinating solvent comprises a primary or secondary amine, for example, decylamine, hexadecylamine, or dioctylamine.

In one aspect, the first inner shell precursor is $Cd(OAc)_2$ and the second inner shell precursor is bis(trimethylsilyl) sulfide ($TMS_2S$). In other aspects, the first and second inner shell precursors are added as a solution in trioctylphosphine (TOP). In other aspects, the first outer shell precursor is diethylzinc ($Et_2Zn$) and the second inner shell precursor is dimethyl zinc ($TMS_2S$). Sometimes, the first and second outer shell precursors are added as a solution in trioctylphosphine (TOP).

In one aspect, the nanoparticles can have ligands that coat the surface. The ligand coating can comprise any suitable compound(s) that provide surface functionality, including facilitating aqueous-dispersibility of the nanoparticles, or permitting binding and/or other interaction with a biomolecule. For example, the surface ligands can be: lipids; phospholipids; fatty acids; polynucleic acids; polyethylene glycol; primary antibodies; secondary antibodies; antibody fragments; protein or nucleic acid based aptamers; biotin; streptavidin; proteins; peptide; small organic molecules; organic or inorganic dyes; or precious or noble metal clusters. Examples of ligands include: amphiphilic polymer (AMP); dihydrolipoic acid (DHLA); tetradecylphosphonic acid (TDPA); octylphosphonic acid (OPA); dipeptides (e.g., His-Leu and Gly-His); alkyl phosphonate; phosphine cross-linker (e.g., tris(hydroxymethyl-phosphine; THP); L-carnosine; imidazole; 4-aminobenzophenone; tris(hydroxymethyl)phosphine; and PEG (e.g., PEG-1000 or amino-dPEG24-acid). See, e.g., U.S. Provisional Applications 61/086,750; 61/102,709; 61/102,683; 61/102,666.

In one aspect, the nanoparticle comprises a core comprising CdSe. In another aspect, the nanoparticle shell can comprise YZ wherein Y is Cd or Zn, and Z is S, or Se. In one embodiment, at least one inner shell layer comprises CdS, and the at least one outer shell layer comprises ZnS.

In one aspect, the nanoparticles exhibit modulated blinking properties, such as limited or no detectable blinking. The nanoparticles can have a stochastic blinking profile in a timescale that is shifted to very rapid blinking or very slow or infrequent blinking relative to a nanoparticle previously described in the art. For example, the nanoparticles may blink on and off on a timescale that is too rapid to be detected under the methods employed to study this behavior.

In one aspect the nanoparticles are photostable. The nanoparticles can exhibit a reduced or no photobleaching with long exposure to moderate to high intensity excitation source while maintaining a consistent spectral emission pattern.

In one aspect, the nanoparticles have a consistently high quantum yield. For example, the nanoparticles can have a quantum yield greater than about 40%, or greater than about 50%, or greater than about 60%, or greater than about 70%, or greater than about 80%.

In one embodiment, the nanoparticles can include a CdSe core. In another aspect the nanoparticles can include a CdS inner shell. In yet another aspect, the nanoparticles can include a ZnS outer shell.

In one embodiment, the spherical nanoparticles can be about 10 nm or smaller. In another embodiment, the rod-shaped nanoparticles can be about 12 nm or smaller, in their largest dimension. In one embodiment, the nanoparticles can include a ligand coating comprising: L-carnosine; dipeptides (e.g., His-Leu and/or Gly-His); 4-aminobenzophenone; citric acid; glycine; tris(hydroxymethyl)phosphine; and amino-dPEG24-acid.

It has been previously shown by others that nanoparticles produce fluorescent signals in a variety of aqueous solutions, including pure water, various buffer solutions, and weakly acidic buffers. Using a single-particle counting procedure, Zhang showed that acidic buffers decrease the fluorescent intensity, but the burst count was not affected (Zhang 2008 Journal of the American Chemical Society 130:3750-3751).

The suitable nanoparticles include those described in U.S. Ser. Nos. 61/086,750, having a 371(c) filing date of Aug. 6, 2008; 61/108,425 having a 371(c) filing date of Oct. 24, 2008; 61/102,631, having a 371(c) filing date of Oct. 3, 2008; 61/102,642, having a 371(c) filing date of Oct. 3, 2008; 61/102,709, having a 371(c) filing date of Oct. 3, 2008; and 61/144,613, having a 371(c) filing date of Jan. 14, 2009.

Methods for Nucleotide Transient-Binding

Provided herein are methods for transiently binding a nucleotide to a mutant polymerase. These methods are conducted under any reaction condition which permits the mutant polymerase to selectively bind a complementary nucleotide, but where incorporation of the complementary nucleotide is perturbed, impeded, or inhibited. Such reaction conditions include utilizing: (1) any reaction conditions and reagents, such as temperature, pH, ionic strength, multivalent cations, and/or time; (2) non-incorporatable nucleotides; and/or (3) a non-extendible polymerization initiation site. Any combination of these reaction conditions can be practiced in any order in the transient-binding methods provided herein.

a) Temperature, pH, Ionic Strength

In one aspect, the methods include any reaction conditions and reagents, such as temperature, pH, and/or ionic strength. For example, the transient-binding reactions can be conducted at a pH range which inhibits polymerase-dependent nucleotide incorporation, such as a pH range of about 4-12, or about 4-10, or about 4-8, or about 4-7.5, or about 4-7, or about 4-6, or about 6-7.5. In another example, the reaction can be conducted at reduced temperatures (e.g., between about 4-25° C.), or elevated temperatures (e.g., between about 25-80° C.). In another example, the reaction can be conducted with increased ionic strength.

b) Time

Other reaction conditions include reducing the time that a nucleotide is contacted with the mutant polymerase to a time that is statistically insufficient to incorporate more than 1 or 2 successive nucleotides (Lapidus, U.S. Pat. No. 7,169,560).

The reduced contact time can be achieved by introducing the nucleotide to the incorporation reaction in rapid flow or wash steps.

c) Metal Cations—Reducing Concentrations of Catalytic Metal Ions

Without wishing to be bound to any theory, a two-metal ion mechanism has been postulated for the phosphoryl transfer reaction of DNA polymerases. The postulate suggests that the catalytic metal ion site (site A) coordinates with the alpha phosphate group of a nucleotide bound to the polymerase, and the B site metal group coordinates with the leaving phosphate groups (Beese and Steitz 1991 EMBO Journal 10:25-33; Steitz and Steitz 1993 Proc. Natl. Acad. Sci. USA 90:6498-6502; Steitz 1998 Nature 391:231-232). Catalytic metal ions can include magnesium, manganese, cobalt, strontium, or barium Accordingly, the reaction conditions can include a reduction, omission, or chelation of any metal ion which permits nucleotide incorporation. The reduction, omission, or chelation of divalent cations, such as magnesium, manganese, cobalt, strontium, or barium, may inhibit nucleotide incorporation. Chelation includes any procedure which renders the divalent cation unavailable for the nucleotide incorporation reaction, including using EDTA and/or EGTA.

The selection of the metal cation for which the concentration will be reduced, omitted or chelated in the reaction conditions, may depend upon the mutant polymerase and nucleotides to be used in the transient-binding reaction. It is known that certain polymerases use magnesium for catalyzing phosphoryl transfer of an incoming triphosphate nucleotide, such as rat polymerase-beta (H Pelletier 1994 Science 264:1981-1903), human polymerase-beta (MR Sawaya 1997 Biochemistry 36:11205-11212), RB69 polymerase (M Wang 2009 Biochemistry 48:2075-2086; HR Lee 2009 48:2087-2098), Klenow (CM Joyce 2008 Biochemistry 47:6103-6116), and HIV reverse transcriptase (N Kaushik 1996 Biochemistry 35:11536-11546; HP Patel 1995 Biochemistry 34:5351-5363). Additionally, it is known that certain polymerases exhibit a preference for unlabeled nucleotides in the presence of magnesium.

It has also been shown that certain DNA polymerases (e.g., phi29) use manganese for incorporating nucleotide polyphosphates having four or more phosphate groups (Kumar, U.S. Pat. No. 7,393,640). Other DNA polymerases, including FY7 polymerase, may use manganese for catalysis (Fuller, U.S. Pat. No. 7,264,934; and Fuller, WO/2007/048033). Still other polymerases may use magnesium or manganese (Fuller, U.S. published patent application No. 2008/0287305), or magnesium and manganese.

Thus, the use of certain combinations of the mutant polymerases and nucleotides may guide the selection of the metal cation(s) that permit/support nucleotide incorporation, and it's concentration to be reduced, omitted, or chelated, in order to inhibit nucleotide incorporation. For example, the transient-binding methods can be conducted using manganese, a mutant RB69 polymerase, and dye-labeled nucleotides (e.g., nucleotides having 3-7 phosphates linked at the terminal phosphate group to a fluorophore via an intervening linker moiety).

In one embodiment, the magnesium can be any magnesium compound including $MgCl_2$. In another embodiment, the manganese can be a manganese compound including $MnCl_2$. In one embodiment, the amount of manganese or magnesium compounds which permits nucleotide incorporation can be about 0.01-10 mM, or about 0.01-5 mM, or about 0.01-3 mM, or about 0.01-2 mM, or about 0.01-1 mM. In another embodiment, the amount of manganese or magnesium compounds which permits nucleotide incorporation can be about 0.01-5 mM, or about 0.05-5 mM, or about 0.1-5 mM, or about 0.2-5 mM, or about 0.3-5 mM, or about 0.4-5 mM, or about 0.5-5 mM, or about 1-5 mM, or about 2-5 mM, or about 3-5 mM, or about 4-5 mM, or about 2-10 mM.

d) Cations Which Inhibit Nucleotide Incorporation

In still another example, the reaction conditions can include at least one type of multivalent cation which permits transient-binding of the nucleotide to the mutant polymerase but inhibits incorporation of the bound nucleotide. The transiently-bound nucleotide can be a complementary or non-complementary nucleotide. The reaction conditions can include a period IV cation including: calcium, scandium, titanium, vanadium, chromium, iron, cobalt, nickel, copper, zinc, gallium, germanium, arsenic, and selenium. The reaction conditions can include other multivalent cations, including rhodium or strontium. The period IV cation compound can be $ZnCl_2$, $CuCl_2$, $CoCl_2$, $FeSO_4$, or $NiCl_2$. It has been previously shown that substituting calcium for magnesium and/or manganese permits nucleotide binding to wild-type or mutant polymerase (e.g., Klenow), but inhibits nucleotide incorporation (Gangurde 2002 Biochemistry 41:14552-14559). The transient-binding reaction conditions can include calcium at about 0.1-50 mM, or about 0.1-40 mM, or about 0.1-30 mM, or about 0.1-20 mM, or about 0.1-10 mM, or about 0.1-5 mM. The reaction condition can include calcium at about 1-20 mM, or about 2-20 mM, or about 3-20 mM, or about 4-20 mM, or about 5-20 mM, or about 6-20 mM, or about 7-20 mM, or about 8-20 mM, or about 9-20 mM, or about 10-20 mM. In another embodiment, the transient-binding reaction conditions can include any calcium compound, including $CaCl_2$ or a nucleotide which is complexed or bound with calcium.

e) Cations which Permit Incorporation

The transient-binding reaction can be followed by a separate reaction/step which permits nucleotide incorporation, which can include the presence of any cation which permits nucleotide incorporation (e.g., manganese and/or magnesium). Accordingly, the methods provided herein include a nucleotide transient-binding step, and a nucleotide incorporation step. The methods can include a nucleotide transient-binding step, a detection step, and a nucleotide incorporation step. The reaction conditions can include a nucleotide transient-binding step, a detection step, a washing step, and a nucleotide incorporation step.

For example, during the nucleotide transient-binding step, the reaction conditions can include a reduced concentration, omission, or chelation, of any metal cation which permit nucleotide incorporation (e.g., magnesium, manganese, cobalt, strontium, or barium), and includes at least one multivalent cation which permits transient-binding but inhibits nucleotide incorporation (e.g., any period IV cation, including calcium, scandium, titanium, vanadium, chromium, iron, cobalt, nickel, copper, zinc, gallium, germanium, arsenic, and selenium; and includes rhodium and strontium).

In another example, the nucleotide transient-binding step can include calcium to permit nucleotide binding but inhibit incorporation, followed by a nucleotide incorporation step which includes a manganese compound (Clark, U.S. published patent application No. 2009/0176233), a magnesium compound, and/or a combination of manganese and magnesium.

In another example, a chemical quench assay can be conducted with calcium during the pulse step and magnesium during the chase step (Lee 2009 Biochemistry 48:2087-2098). In a related example, a FRET/quench assay can be conducted in the presence of calcium or magnesium (Joyce 2008 Biochemistry 47:6103-6116) for testing Klenow fragment (cysteine 744 mutant) labeled with IAEDNAS donor dye bound to primer/template labeled with DABCYL acceptor/quench dye.

In another example, the transient-binding reaction includes a concentration of any metal cation which permits nucleotide incorporation, and a concentration of any multivalent cation which permits transient-binding but inhibits nucleotide incorporation. In one embodiment, the A and B metal binding sites on the mutant polymerase are both occupied by the multivalent cation, or one of the sites is occupied by the multivalent cation.

f) Cations which Promote Ternary Complex Formation and/or Stability

In yet another example, the reaction conditions can include at least one type of exchange-inert cation which is complexed with a nucleotide, to permit transient-binding of the nucleotide to the mutant polymerase and inducing ternary complex formation (or stabilizing the ternary complex), but inhibiting incorporation of the bound nucleotide. The transiently-bound nucleotide can be a complementary or non-complementary nucleotide.

During nucleotide polymerization events, the mutant polymerase can be in an open conformation prior to binding a nucleotide. Upon binding the complementary nucleotide, the mutant polymerase can change to a closed conformation (also known as the ternary complex). The ternary complex can include the mutant polymerase (in a closed conformation) which is bound to the template nucleic acid molecule which is base-paired with the polymerization initiation site, and the nucleotide. The mutant polymerase, in a closed conformation, can catalyze incorporation of the bound nucleotide. It is known that some cation-nucleotide complexes (e.g., chromium-nucleotides) promote the formation and/or stability of the ternary complex.

The transient binding reactions can include at least one type of cation which promotes the formation and/or the stability of the ternary complex. These reactions can be conducted in the presence or absence of cations that are required for catalysis (e.g., $Mg^{2+}$ and/or $Mn^{2+}$). For example, Cr(III)•nucleotide complexes have been previously used as Mn(II)•nucleotide analogs when conducting exchange-inert reactions with polymerases (Zhong, et al., 1998 Journal Am Chem Soc 120:235-236). Zhong complexed DNA polymerase β from rat brain with DNA template/primer duplexes containing the 2-aminopurine nucleotide analog opposite of the incoming nucleotide insertion site, and reacted the polymerase-DNA binary complex with a Cr(III)•nucleotide complex in the absence of a catalytic metal cation (e.g., $Mg^{2+}$). The Cr(III)•nucleotide complex induced the polymerase to form a ternary conformation without catalysis, as indicated by the change of the 2-aminopurine fluorescence.

In one embodiment, the transient binding reactions can be conducted with a mutant polymerase bound to a nucleic acid template molecule which is base-paired with a polymerization initiation site and a Cr(III)•nucleotide complex (e.g., a complementary nucleotide) without $Mg^{2+}$ or $Mn^{2+}$. The Cr(III)•nucleotide complex can induce the formation of a ternary complex. The presence of the bound Cr(III)•nucleotide complex, and/or the identity of the base in the Cr(III)•nucleotide complex, can be detected if the Cr(III)•nucleotide complex is labeled with a fluorescent reporter moiety. A catalytic cation can be added (e.g., $Mg^{2+}$ or $Mn^{2+}$) to induce cleavage and incorporation of the chromium-complexed nucleotide.

The Cr(III)•nucleotide complex can be a chromium monodentate, bidentate, or tridentate complex. The Cr(III)•nucleotide complex can be an α-monodentate, or β-γ-bidentate nucleotide. The Cr(III)•nucleotide complex can be prepared using any well known methods, including mixing together nucleotides (e.g., dATP, dGTP, dCTP, dTTP, or dUTP) with chromium (e.g., $CrCl_3$) at an elevated temperature (e.g., approximately 80° C. (see Dunaway-Mariano and Cleland 1980 Biochemistry 19:1496-1505; Dunaway-Mariano and Cleland 1980 Biochemistry 19:1506-1515). The various diastereomers of the β-γ-bidentate can be separated using reverse-phase HPLC techniques (Gruys and Schuster 1982 Analytical Biochemistry 125:66-73). Characterization of the various diastereomers can be done using phosphorus NMR or mass spectrometry.

Non-Extendible Polymerization Initiation Site

In some embodiments, the nucleotide transient-binding methods can be conducted using a non-extendible polymerization initiation site. The extendible polymerization initiation site can include a terminal 3'—OH group which serves as a substrate for the mutant polymerase to form a phosphodiester bond between the terminal 3'—OH group and an incoming nucleotide. The extendible polymerization initiation site can be the terminal 3'—OH group on a primer molecule, or an internal 3'—OH group in a nick or gap within a nucleic acid molecule. The non-extendible polymerization initiation site can be a terminal group which does not serve as a substrate for polymerase-dependent nucleotide incorporation. For example, the non-extendible polymerization initiation site can be a terminal nucleotide which lacks a terminal 3'—OH group, or includes a sugar-linked 2' or 3' blocking group, or can include a base-linked moiety which inhibits extension by a given polymerase (e.g., mutant polymerase), or can include a sugar- or base-linked moiety which is bulky or is negatively charged.

In one embodiment, the nucleotide transient-binding methods can be performed by binding the mutant polymerase to a template molecule which is base-paired with a polymerization initiation site having a non-extendible end. The mutant polymerase binds and interrogates a candidate nucleotide, but the candidate nucleotide is not incorporated. A signal from the transiently-bound candidate nucleotide is detected, and its identity is deduced. The non-extendible end can include a dideoxynucleotide or a terminator nucleotide.

Strand extension can be performed if the non-extendible end of the polymerization initiation site is modified or removed to provide an extendible end (e.g., de-blocking). When a terminator nucleotide is incorporated at the extendible end, it can provide a new non-extendible end. The mutant polymerase binds and interrogates another candidate labeled nucleotide, and a signal is detected from the transiently-bound nucleotide. And the steps can be repeated.

In some embodiments, the reaction conditions can include reducing the temperature and/or pH, omitting manganese and/or magnesium, and/or adding calcium, or any combination thereof.

Identifying a Nucleotide Bound to a Polymerase:

Optionally, the identity of a transiently-bound nucleotide can be determined according to the methods provided herein. In one aspect, methods for identifying a nucleotide bound to a mutant polymerase, comprises the steps of: (a) contacting at least one type of a labeled nucleotide to an immobilized complex having a first polymerase (e.g., mutant polymerase) bound to a template nucleic acid molecule which is bound to a polymerization initiation site, under suitable conditions to transiently-bind the at least one type of labeled nucleotide to the active site of the polymerase in a nucleic acid template-dependent manner and to inhibit nucleotide polymerization by the polymerase; (b) exciting the labeled nucleotide with an excitation source; (c) detecting a signal, or a change in a signal, from the transiently-bound labeled nucleotide; and (d) identifying the nucleotide transiently-bound to the polymerase.

In one embodiment, the methods for identifying a nucleotide bound to a mutant polymerase, further comprises the steps of: (e1) removing the transiently-bound nucleotide; and (f1) contacting the complex with at least one type of nucleotide under suitable conditions for the polymerase to polymerize the nucleotide. In this embodiment, the same polymerase in step (a1) is contacted in step (f1).

In another embodiment, the methods for identifying a nucleotide bound to a polymerase, further comprises the steps of: (e2) removing the first polymerase and the transiently-bound nucleotide so that the template nucleic acid molecule, nucleic acid primer molecule or self-priming template nucleic acid molecule remains immobilized to the surface; (f2) binding the remaining template nucleic acid molecule with a second polymerase; and (g2) contacting the second polymerase with at least one type of nucleotide under suitable conditions for the second polymerase to polymerize the nucleotide. In this embodiment, the polymerase in step (a2) is different from the polymerase in step (f2).

Nucleotide Transient-Binding Reactions I:

In one embodiment, a method for identifying a nucleotide bound to a polymerase, comprises the steps of: (a1) contacting at least one type of a labeled nucleotide to an immobilized complex having a polymerase (e.g., mutant polymerase) bound to a template nucleic acid molecule which is bound to a polymerization initiation site, under suitable conditions to transiently-bind the at least one type of labeled nucleotide to the polymerase in a nucleic acid template-dependent manner and to inhibit nucleotide polymerization by the polymerase; (b1) exciting the first labeled nucleotide with an excitation source; (c1) detecting a signal, or a change in a signal, from the transiently-bound labeled nucleotide; and (d1) identifying the nucleotide transiently-bound to the polymerase; (e1) removing the transiently-bound nucleotide; (f1) contacting the complex with at least one type of nucleotide under suitable conditions for the polymerase to polymerize the nucleotide; and (g1) repeating steps (a1)-(e1)

Nucleotide Transient-Binding Reactions II:

In one embodiment, a method for identifying a nucleotide bound to a polymerase, comprises the steps of: (a2) contacting at least one type of a labeled nucleotide to an immobilized complex having a polymerase (e.g., mutant polymerase) bound to a template nucleic acid molecule which is base-paired to a nucleic acid primer molecule or the immobilized complex having a polymerase bound to a self-priming template nucleic acid molecule, under suitable conditions to transiently-bind the at least one type of labeled nucleotide to the polymerase in a nucleic acid template-dependent manner and to inhibit nucleotide polymerization by the polymerase; (b2) exciting the first labeled nucleotide with an excitation source; (c2) detecting a signal, or a change in a signal, from the transiently-bound labeled nucleotide; and (d2) identifying the nucleotide transiently-bound to the polymerase; (e2) removing the polymerase and the transiently-bound nucleotide so that the template nucleic acid molecule, primer nucleic acid molecule or self-priming template nucleic acid molecule remains immobilized to the surface; (f2) binding the remaining template nucleic acid molecule with a second polymerase; (g2) contacting the second polymerase with at least one type of nucleotide under suitable conditions for the second polymerase to polymerize the nucleotide; and (h2) repeating steps (a2)-(f2).

a) Suitable Conditions for Nucleotide Transient Binding:

In one embodiment, the suitable conditions to transiently bind the nucleotide to the polymerase in step (a1) or (a2) comprise: (i) reducing the levels or omission of a metal cation that permits nucleotide incorporation and/or addition of a cation that inhibits nucleotide incorporation; (ii) using a polymerase (e.g., mutant polymerase) which selectively binds the nucleotide in a template-dependent manner and exhibits reduced nucleotide incorporation activity; (iii) using at least one type of labeled nucleotide which can be a labeled non-incorporatable nucleotide; and/or (iv) using a polymerization initiation site which can be a non-extendible polymerization initiation site. Any combination of these suitable conditions can be practiced to identify the nucleotide bound to the polymerase.

b) Suitable Conditions for Nucleotide Incorporation:

In another embodiment, the suitable conditions for polymerizing the nucleotide in step (f1) or (g2) comprise: (i) including a metal cation that permits nucleotide incorporation and/or reducing the levels or omission of a cation that inhibits nucleotide incorporation; (ii) using a polymerase (e.g., mutant polymerase) which selectively binds the nucleotide in a template-dependent manner and polymerizes the bound nucleotide; (iii) using at least one type of incorporatable nucleotide; and/or (iv) using a polymerization initiation site having an extendible polymerization initiation site.

c) Polymerization Initiation Site:

In one embodiment, the polymerization initiation site can be the 3' terminal end of a nucleic acid primer molecule or of self-priming template nucleic acid molecule. In another embodiment, the polymerization initiation site can be base-paired to the template nucleic acid molecule. In another embodiment, the polymerization initiation site can be an extendible terminal 3'OH group or a non-extendible terminal group. In another embodiment, the polymerization initiation site can be a terminal 3'OH group of the nucleic acid primer molecule or a terminal 3'OH group of a self-priming template nucleic acid molecule.

d) Template Molecules:

In one embodiment, the template nucleic acid molecule can be a DNA molecule, RNA molecule, or DNA/RNA hybrid molecule.

e) Immobilized Template Molecules:

In one embodiment, the template nucleic acid molecule, the nucleic acid primer molecule, or self-priming template nucleic acid molecule can be immobilized to a surface.

f) Cation:

In one embodiment, the cation that inhibits nucleotide incorporation can be calcium, scandium, titanium, vanadium, chromium, iron, cobalt, nickel, copper, zinc, gallium, germanium, arsenic, selenium, rhodium, or strontium.

g) Polymerases:

In one embodiment, the first polymerase binds the labeled nucleotide in a nucleic acid template-dependent manner and exhibits reduced nucleotide incorporation activity. In another embodiment, the first polymerase can be a DNA-dependent, mutant RB69 polymerase. In one embodiment, the mutant polymerase, under certain reaction conditions, can bind nucleotides but exhibits reduced nucleotide incorporation activity. In another embodiment, a suitable mutant polymerase can be selected that can bind the labeled nucleotide. In another embodiment, a suitable mutant polymerase can be selected that can bind the template nucleic acid molecule which can be base-paired to the polymerization initiation site. In another embodiment, the polymerization initiation site can include a terminal 3'OH extendible end or a terminal 3' non-extendible end. In another embodiment, a suitable mutant polymerase can be selected that can bind an incorporatable or a non-incorporatable nucleotide. In still another embodiment, the mutant polymerase can be operably linked to a reporter moiety (e.g., energy transfer donor moiety). In another embodiment, the mutant polymerase in step (a) can be an RB69 (exo-) (FIGS. 2-8; SEQ ID NO:2-8, respectively).

In another embodiment, the second polymerase can be the same type or a different type as the first polymerase.

h) Labeled Nucleotides:

In some embodiments, the labeled nucleotide can include 3-10 or more phosphate groups. In another embodiment, the labeled nucleotide can be adenosine, guanosine, cytidine, thymidine or uridine, or any other type of labeled nucleotide. In another embodiment, the mutant polymerase can be contacted with more than one type of labeled nucleotide (e.g., A, G, C, and/or T/U, or others). In another embodiment, each type of labeled nucleotide can be operably linked to a different reporter moiety to permit nucleotide identity. In another embodiment, each type of labeled nucleotide can be operably linked to one type of reporter moiety. In another embodiment, the labeled nucleotides are operably linked at the terminal phosphate group with a reporter moiety. In another embodiment, the labeled nucleotides are operably linked at the base moiety with a reporter moiety. In another embodiment, the labeled nucleotide can be a non-incorporatable nucleotide.

In some embodiments, the non-incorporatable nucleotide can bind to the mutant polymerase and template nucleic acid molecule which can be base-paired to a polymerization initiation site, in a template-dependent manner, but does not incorporate. In one embodiment, different types of labeled nucleotides can be employed in the method for detecting the presence of a transiently-bound nucleotide in order to determine the frequency, duration, or intensity, of a transiently-bound nucleotide. For example, a comparison can be made between the frequency/duration/intensity of transiently-bound complementary and non-complementary nucleotides. Typically, for direct excitation of the reporter moiety, the length of the transient binding time of a complementary nucleotide can be longer and/or more frequent compared to that of a non-complementary nucleotide. Typically, for FRET-based excitation and detection of the reporter moieties, the transient binding time of a complementary nucleotide can be of longer duration compared to that of a non-complementary nucleotide.

i) Non-Incorporatable Nucleotides:

In one embodiment, the labeled nucleotide in step (a) can be a labeled non-incorporatable nucleotide. In another embodiment, the labeled non-incorporatable nucleotide can be an adenosine, guanosine, cytidine, thymidine, or uridine nucleotide.

j) The Labels:

In one embodiment, the label (on the incorporatable or non-incorporatable nucleotides) can be an energy transfer acceptor reporter moiety. In another embodiment, the label can be a fluorescent dye. In another embodiment, the adenosine, guanosine, cytidine, thymidine, or uridine nucleotides can be operably linked to different types of labels. In another embodiment, the complex can be contacted with at least two types of labeled nucleotides in step (a). In another embodiment, the at least two types of nucleotides can have different types of labels.

k) Energy Transfer Moieties:

In one embodiment, the mutant polymerase can be operably linked to an energy transfer donor reporter moiety. In another embodiment, the energy transfer donor reporter moiety can be an inorganic nanoparticle or a fluorophore. In another embodiment, the mutant polymerase can be operably linked to an energy transfer donor reporter moiety and the transiently-bound nucleotide can be operably linked to an energy transfer acceptor reporter moiety. In another embodiment, the transiently-bound labeled nucleotide can emit a FRET signal. In another embodiment, the signal from the transiently-bound labeled nucleotide can be optically detectable.

l) FRET Signals

In one embodiment, the mutant polymerase can be operably linked to an energy transfer donor (e.g., fluorescent dye or nanoparticle). In another embodiment, the labeled nucleotide can have an energy transfer acceptor moiety (e.g., fluorescent dye). In yet another embodiment, the energy transfer donor and acceptor can be a FRET pair. In another embodiment, the signal (or change in the signal) from the energy transfer donor or acceptor can be used to detect the presence of the transiently-bound nucleotide. In still another embodiment, the signal emitted by the transiently-bound nucleotide can be a FRET signal.

m) Chain Terminating Nucleotides:

In one embodiment, the non-extendible terminal group can be an inhibitor moiety which inhibits incorporation of a subsequent in-coming nucleotide. In another embodiment, the inhibitor moiety can be removable via an enzymatic, heat, chemical, or light cleavage reaction.

n) Excitation Source and Signals:

In one embodiment, the excitation source can be electromagnetic radiation. The excitation source can be a laser. The signal, or the change in the signal, can be optically detectable. In one embodiment, the mutant polymerase has an active site. The active site can be enzymatically-active. The labeled nucleotide can bind the active site, thereby bringing the mutant polymerase and labeled nucleotide in close proximity with each other. The mutant polymerase may be labeled or unlabeled. In one embodiment, the signal or change in the signal can be a fluorescent signal resulting from direct excitation of the label which can be operably linked to the transiently-bound labeled nucleotide or to the labeled mutant polymerase. In one embodiment, the energy transfer donor and/or acceptor moieties can fluoresce in response to direct excitation. These fluorescence responses can be a signal or change in a signal. In another embodiment, the energy transfer acceptor moiety can fluoresce in response to energy transferred from a proximal excited energy transfer donor moiety. These fluorescence responses can be a signal or change in a signal.

The proximal distance between the donor and acceptor moieties that accommodates energy transfer can be dependent upon the particular donor/acceptor pair. The proximal distance between the donor and acceptor moieties can be about 1-20 nm, or about 1-10 nm, or about 1-5 nm, or about 5-10 nm. In another embodiment, the energy transfer signal generated by proximity of the donor moiety to the acceptor moiety can remain unchanged. In another embodiment, the energy transfer signal generated by proximity of the donor moiety to the acceptor moiety results in changes in the energy transfer signal. In another embodiment, the changes in the signal or the energy transfer signal from the donor or acceptor moiety can include changes in the: intensity of the signal; duration of the signal; wavelength of the signal; amplitude of the signal; polarization state of the signal; duration between the signals; and/or rate of the change in intensity, duration, wavelength or amplitude. In another embodiment, the change in the signal or the energy transfer signal can include a change in the ratio of the change of the energy transfer donor signal relative to change of the energy transfer acceptor signals. In another embodiment, the signal or the energy transfer signal from the donor can increase or decrease. In another embodiment, the signal or the energy transfer signal from the acceptor can increase or decrease. In another embodiment, the signal or the energy transfer signal associated with nucleotide transient-binding includes: a decrease in the donor signal when the donor is proximal to the acceptor; an increase in the acceptor signal when the acceptor is proximal to the donor; an increase in the donor signal when the distance between the donor and acceptor increases; and/or a decrease in the acceptor signal when the distance between the donor and acceptor increases.

o) Detection:

In one embodiment, the detecting the signal or change in the signal can be performed using confocal laser scanning microscopy, Total Internal Reflection (TIR), Total Internal Reflection Fluorescence (TIRF), near-field scanning microscopy, far-field confocal microscopy, wide-field epi-illumination, light scattering, dark field microscopy, photoconversion, wide field fluorescence, single and/or multi-photon excitation, spectral wavelength discrimination, evanescent wave illumination, scanning two-photon, scanning wide field two-photon, Nipkow spinning disc, and/or multi-foci multi-photon.

p) Identifying the Transiently-Bound Nucleotide:

In practicing the nucleotide transient-binding methods, non-desirable fluorescent signals can come from sources including background and/or noise. In one embodiment, the desirable signals can be distinguished from the non-desirable fluorescent signals by measuring, analyzing and characterizing attributes of all fluorescent signals generated by the nucleotide transient-binding reaction. In one embodiment, attributes of the signal that can permit distinction from the non-desirable fluorescent signals can include: duration; wavelength; amplitude; photon count; and/or the rate of change of the duration, wavelength, amplitude; and/or photon count. In one embodiment, the identifying the signal, includes measuring, analyzing and characterizing attributes of: duration; wavelength; amplitude; photon count and/or the rate of change of the duration, wavelength, amplitude; and/or photon count. In one embodiment, identifying the signal can be used to identify the transiently-bound nucleotide.

q) Washing Steps

In yet another embodiment, washing steps can be included after any of the steps, for example, to remove the non-incorporated nucleotides and/or the labeled nucleotides. In the wash step, magnesium, manganese, or calcium can be omitted or included.

EXAMPLES

All of the compositions and methods disclosed and claimed herein can be made and executed without undue experimentation in light of the present disclosure. In some cases, the compositions and methods of this invention have been described in terms of embodiments, however these embodiments are in no way intended to limit the scope of the claims, and it will be apparent to those of skill in the art that variations may be applied to the compositions and/or methods and in the steps or in the sequence of steps of the methods described herein without departing from the concept, spirit and scope of the invention. More specifically, it will be apparent that certain components which are both chemically and physiologically related may be substituted for the components described herein while the same or similar results would be achieved. All such similar substitutes and modifications apparent to those skilled in the art are deemed to be within the spirit, scope and concept of the invention as defined by the appended claims.

Example 1

Preparing Mutant RB69 Polymerase (3PDX)

The nucleotide sequence encoding the 3PDX DNA polymerase (FIG. 2, SEQ ID NO:2) was cloned into pTTQ expression vector (Invitrogen, Carlsbad, Calif.). The vector was transformed into T7 express B1-21 cell line (New England Biolabs). The expressing cell line was grown in 2YT media at 37° C. (Invitrogen #22712-020). When the optical density of the growing culture reached 0.6 OD, the cells were induce with 0.5M IPTG, then shifted to 15° C. and allowed to continue to grow overnight. Cells were concentrated by differential centrifugation, stored at −80° C.

Cells were resuspended in 50 mM TRIS pH 7.5, 50 mM Glucose, 0.1 mM EDTA (pH 8.0), 0.05% Tween-20 and 1 mM DTT, and ruptured by high pressure using a Microfluidizer, ML-110PS, (Microfluidics). While stirring on ice, the salt concentration of the lysate was increased to a final concentration of 1M NaCl. Streptomycin sulfate was added to the lysate to a final concentration of 0.2% and the lysate was stirred for 20 minutes. Cell debris was removed by differential centrifugation. PEI (polyethylenime) was added to the lysate to a final concentration of 2%, while stirring on ice. The precipitated DNA was removed by differential centrifugation. The lysate was precipitated with ammonium sulfate at a final concentration of 65%. The resulting pellets were stored at −20° C. until further processing.

The expressed protein was purified using four columns. The components of the column buffers included: Buffer A: 25 mM HEPES (pH 7.5), 0.1 mM EDTA, 0.05% Tween-20 and 1 mM DTT. Buffer B: 25 mM HEPES (pH 7.5), 0.1 mM EDTA, 0.05% Tween-20, 1 mM DTT and 1M NaCl. The pellets from the ammonium sulfate precipitation were resuspended in Buffer A until the conductivity reached ~11 mS/cm. The sample was filtered with a 1 µm filter (Acrodisc 1 µM Glass fiber membrane, 37 mm; PALL) and the collected protein was purified by the following four columns: (1) EMD sulfite cation exchange column, (Merck chemicals); (2) Poros HQ20, 10×100 mm column (Life Technologies); (3) Poros PI20 (10×100 mm) column (Life Technologies); and (4) PorosHE50 (10×100 mm) column (Life Technologies). The sample was loaded on the first column, the proteins were eluted with a 20 column volume gradient from 0 to 100% Buffer B, (0 to 1 M NaCl). The fractions containing the expressed protein were identified by SDS PAGE gel (NuPAGE, 10% denaturing gel, using MES Buffer). These fractions were pooled and applied to the next column. This method was repeated for the next three columns. After the final column, the fractions containing the purified protein were identified and pooled for dialysis in 10 mM Tris pH 7.5, 0.1 mM EDTA, 100 mM NaCl and 50% glycerol. The protein was dialyzed overnight (10 MWCO).

The purified protein was concentrated four fold. The protein concentration was determined by UV280. The enzyme was assayed for exogenous DNAse contamination and polymerase activity. Protein Purity was determined by SDS PAGE gel electrophoresis.

Example 2

Analyzing Polymerase Kinetics Using Stopped-Flow Spectrometer

The kinetics of nucleotide incorporation by Phi29 and RB69 polymerases were compared using stopped-flow spectrometry.

1) Phi29 Polymerase: Stopped Flow Measurements of $t_{pol}$

Template A1 sequence:
(SEQ ID NO: 12)
AF546-5'-CGTTCCACGCCCGCTCCTTTGCAAC-3'

Template T1 sequence:
(SEQ ID NO: 13)
AF546-5'-CGAACCTCGCCCGCTCCTTTGCAAC-3'

Template C1 sequence:
(SEQ ID NO: 14)
AF546-5'-CGTTAACCGCCCGCTCCTTTGCAAC-3'

Template G1 sequence:
(SEQ ID NO: 15)
AF546-5'-CGTTAAGCGCCCGCTCCTTTGCAAC 3'

Primer sequence:
(SEQ ID NO: 16)
5'-GTTGCAAAGGAGCGGGCG-3'

The kinetics of nucleotide incorporation by recombinant phi 29 (exo-) (HP-1) and RB69 (exo-) (SEQ ID NO:4) (see section 4 below) DNA polymerases were measured in an Applied Photophysics SX20 stopped-flow spectrometer by monitoring changes in fluorescence from ALEXA FLUOR 546-labeled primer/template duplex following the mixing of the enzyme-DNA complex with dye-labeled nucleotides in the reaction buffer containing 50 mM Tris-HCl, pH 7.5, 50 mM NaCl, 4 mM DTT, 0.2% BSA, and 2 mM MnCl$_2$ or 5 mM CaCl$_2$. The reactions included 330 nM recombinant DNA polymerase, 100 nM template/primer duplex, and 7 µM labeled nucleotides.

Figure 9B:
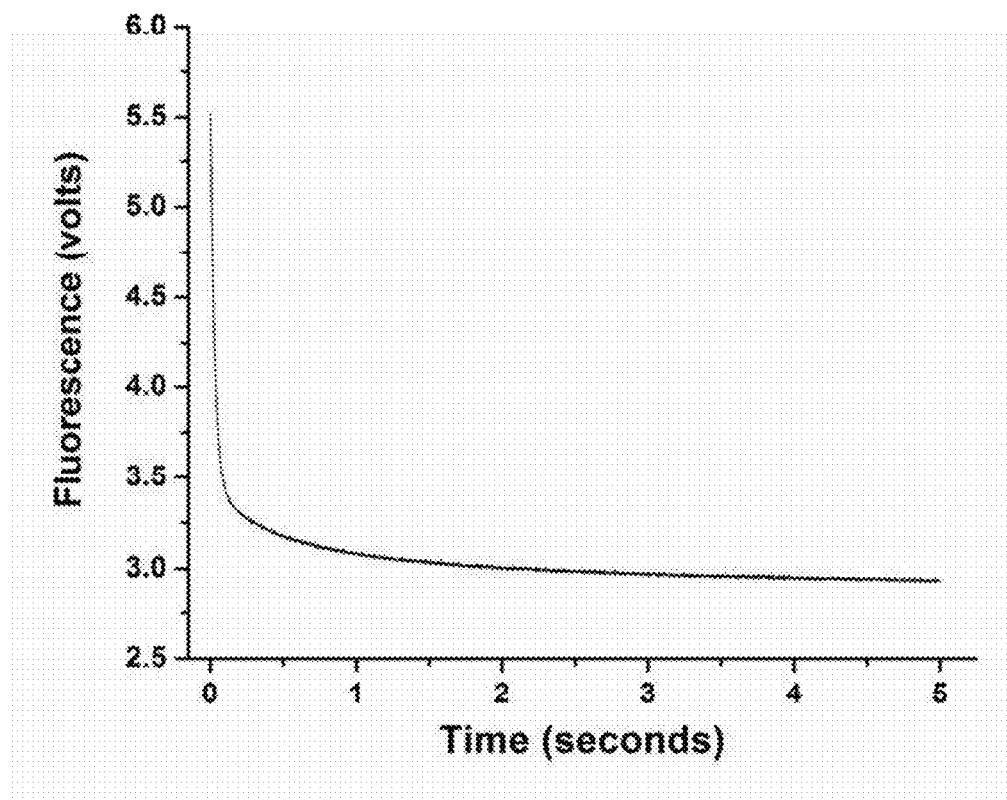
FIG. 9B shows a stopped-flow fluorescence trace ($t_{pol}$) for Phi29 (exo-) polymerase and terminal phosphate labeled dN4P nucleotides in the presence of calcium (Example 2).

The averaged (5 traces) stopped-flow fluorescence traces (>1.5 ms) were fitted with a double exponential equation (1) to extrapolate the rates of the nucleotide binding and product release, $$\text{Fluorescence} = A_1 * e^{-k1*t} + A_2 * e^{-kpol*t} + C \qquad \text{(equation 1)}$$

where $A_1$ and $A_2$ represent corresponding fluorescence amplitudes, C is an offset constant, and k1 and kpol are the observed rate constants for the fast and slow phases of the fluorescence transition, respectively. The dye-labeled nucleotides comprise terminal-phosphate-labeled nucleotides having an alkyl linker with a functional amine group attached to the dye. The stopped-flow techniques for measuring $t_{pol}$ ($1/k_{pol}$) followed the techniques described by MP Roettger (2008 Biochemistry 47:9718-9727; M. Bakhtina 2009 Biochemistry 48:3197-320). Representative stopped-flow fluorescence traces for Phi29 (exo-) polymerase and terminal phosphate labeled dN4P nucleotides in the presence of manganese are shown in FIG. 9A, or in the presence of calcium (FIG. 9B).

2) Phi 29 Polymerase: Stopped Flow Measurements of $t_{-1}$

Template A2 sequence:
(SEQ ID NO: 17)
AF546-5'-CAGTCCAGGA GTT GGT TGG ACG GCT GCG AGG C-3'

Template T2 sequence:
(SEQ ID NO: 18)
AF546-5'-CAGTAATGGA GTT GGT TGG ACG GCT GCG AGG C-3'

Template C2 sequence:
(SEQ ID NO: 19)
AF546-5'-CAGTAACGG AGT TGG TTG GAC GGC TGC GAG GC-3'

Template G2 sequence:
(SEQ ID NO: 20)
AF546-5'-CAGTAAGGGA GTT GGT TGG ACG GCT GCG AGG C-3'

Dideoxy-primer sequence:
(SEQ ID NO: 21)
5'-GCC TCG CAG CCG TCC AAC CAA CTC ddC-3'

Primer sequence:
(SEQ ID NO: 22)
5'-GCC TCG CAG CCG TCC AAC CAA CTC C-3'

The rate of the nucleotide dissociation ($k_{-1}$) from the ternary complex of [enzyme•DNA•nucleotide] was measured in an Applied Photophysics SX20 stopped-flow spectrometer by monitoring changes in fluorescence from ALEX-AFLUOR546-labeled primer/template duplex following the mixing of the [enzyme•DNA•labeled nucleotide] ternary complex with: (A) 50 µM cognate non-labeled deoxynucleoside triphosphate in a buffer containing 50 mM Tris-HCl (pH 7.5), 50 mM NaCl, 4 mM DTT, 0.2% BSA, and 2 mM MnCl$_2$, or (B) 50 µM cognate non-labeled deoxynucleoside triphosphate in a buffer containing 50 mM Tris-HCl (pH 7.5), 50 mM NaCl, 4 mM DTT, 0.2% BSA, and 5 mM CaCl$_2$ (for Phi29 (exo-) (HP-1) polymerase) or 10 mM CaCl$_2$ (for RB69 (exo-) polymerase).

The ternary complexes were prepared using: 330 nM polymerase (Phi29(exo-) or RB69), 100 nM template/primer duplex, and 7 µM terminal phosphate-labeled nucleotides.

Figure 9C:
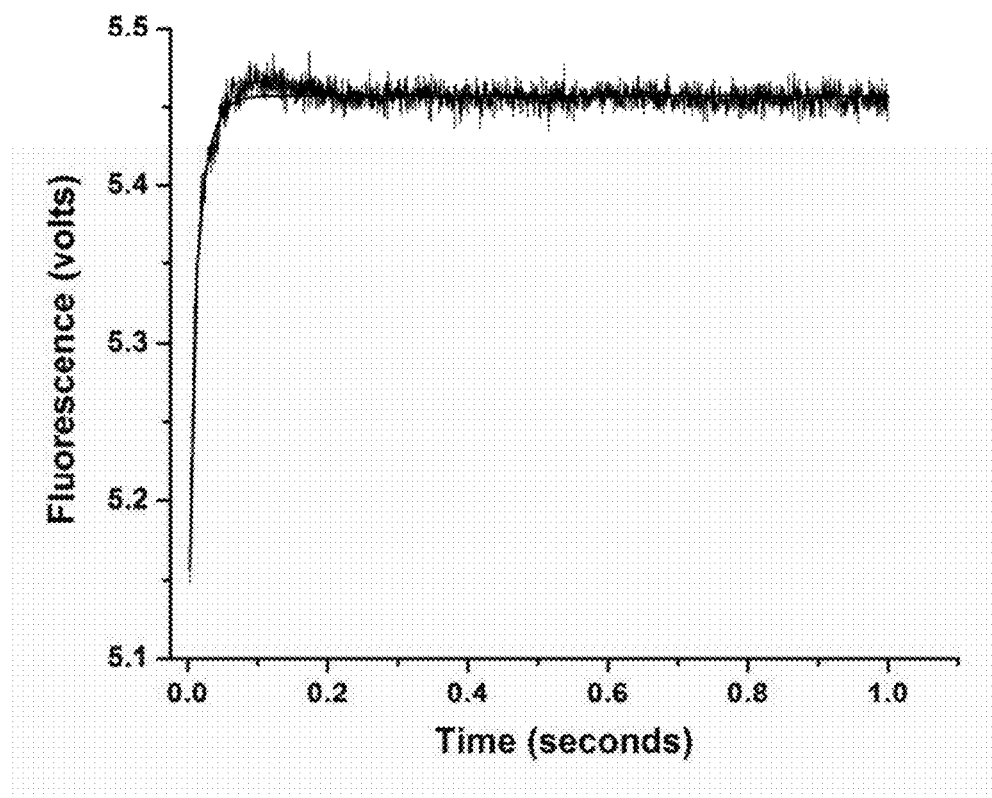
FIG. 9C shows a stopped-flow fluorescence trace ($t_{-1}$) for Phi29 (exo-) polymerase and terminal phosphate labeled dN4P nucleotides in the presence of manganese (Example 2).
Figure 9D:
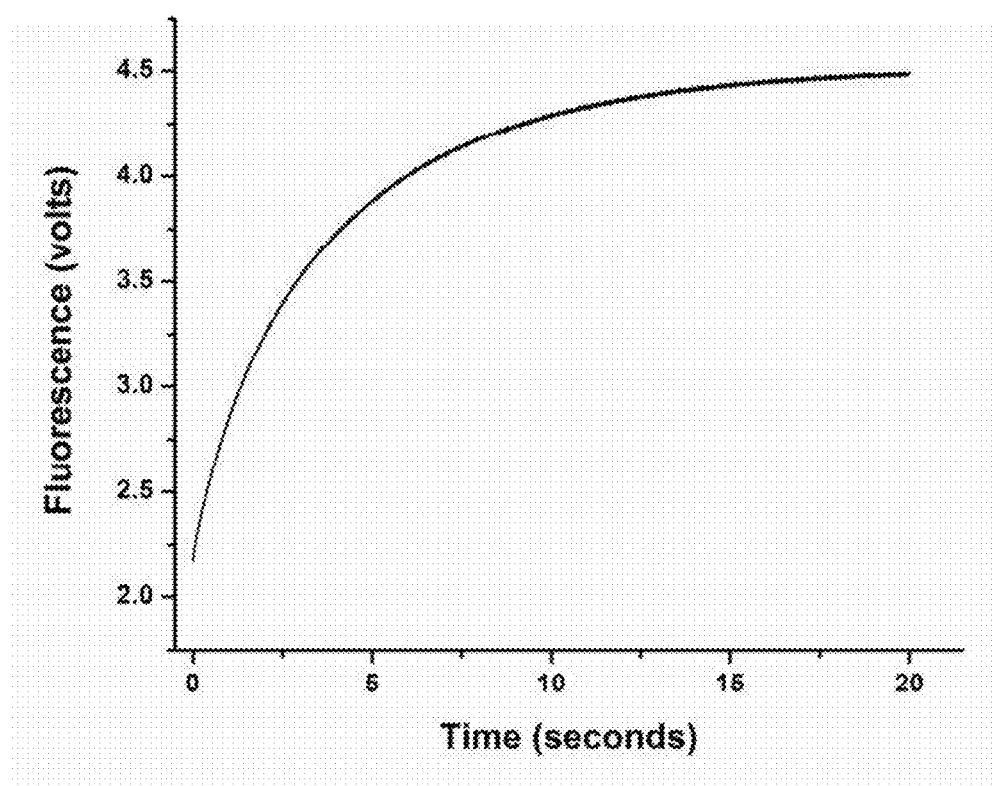
FIG. 9D shows a stopped-flow fluorescence trace ($t_{-1}$) for Phi29 (exo-) polymerase and terminal phosphate labeled dN4P nucleotides in the presence of calcium (Example 2).

The averaged stopped-flow fluorescence traces (>1.5 msec) were fitted with a single exponential equation (2) to extrapolate the rate of the nucleotide dissociation ($k_{-1}$) from the [enzyme•DNA•nucleotide] ternary complex.

$$\text{Fluorescence} = A_1 * e^{-k-1*t} + C \qquad \text{(equation 2)}$$

where $A_1$ represents the corresponding fluorescence amplitude, C is an offset constant, and $k_{-1}$ and the observed rate constants for the fluorescence transition. The stopped-flow techniques for measuring $t_{-1}$ ($1/k_{-1}$) followed the techniques described by M. Bakhtina (2009 Biochemistry 48:3197-3208). Representative stopped-flow fluorescence traces for Phi29 polymerase and terminal phosphate labeled dN4P nucleotides in the presence of manganese are shown in FIG. 9C or in the presence of calcium (FIG. 9D).

Figure 9E:
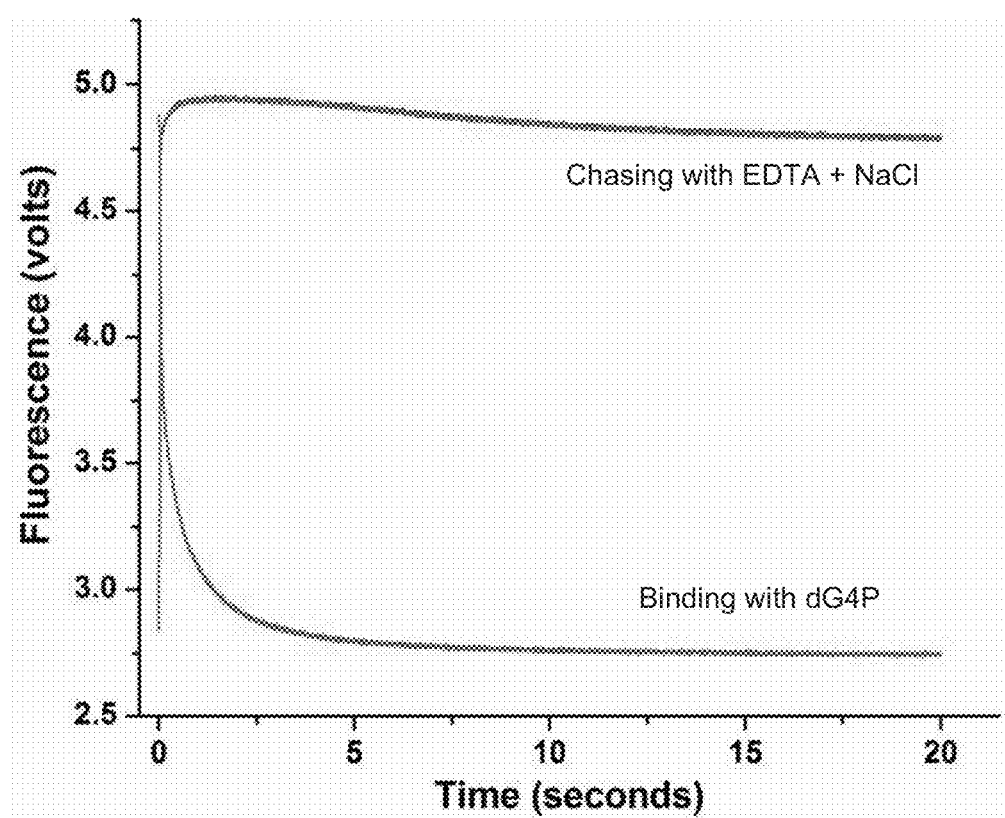
FIG. 9E shows stopped-flow fluorescence traces for Phi29 (exo-) polymerase and terminal phosphate labeled dN4P nucleotides in the presence of calcium (binding with dG4P) or manganese (chasing with EDTA+NaCl) (Example 2).

3) Phi29 Polymerase: Stopped-Flow Measurements for Characterizing Nucleotide Transient-Binding:

Stopped-flow procedures were conducted to characterize the $t_{pol}$ (using 7 µM terminal phosphate labeled dG4P-AF647 and calcium) and $t_{-1}$ rates (chased with 0.1 mM EDTA and 150 mM NaCl) of various polymerases. Representative stopped-flow fluorescence traces for Phi29 are shown in FIG. 9E. The results show that transient-binding of the nucleotide by Phi29 polymerase, in the presence of calcium, is reversible by chelating the calcium with the addition of EDTA.

Figure 9F:
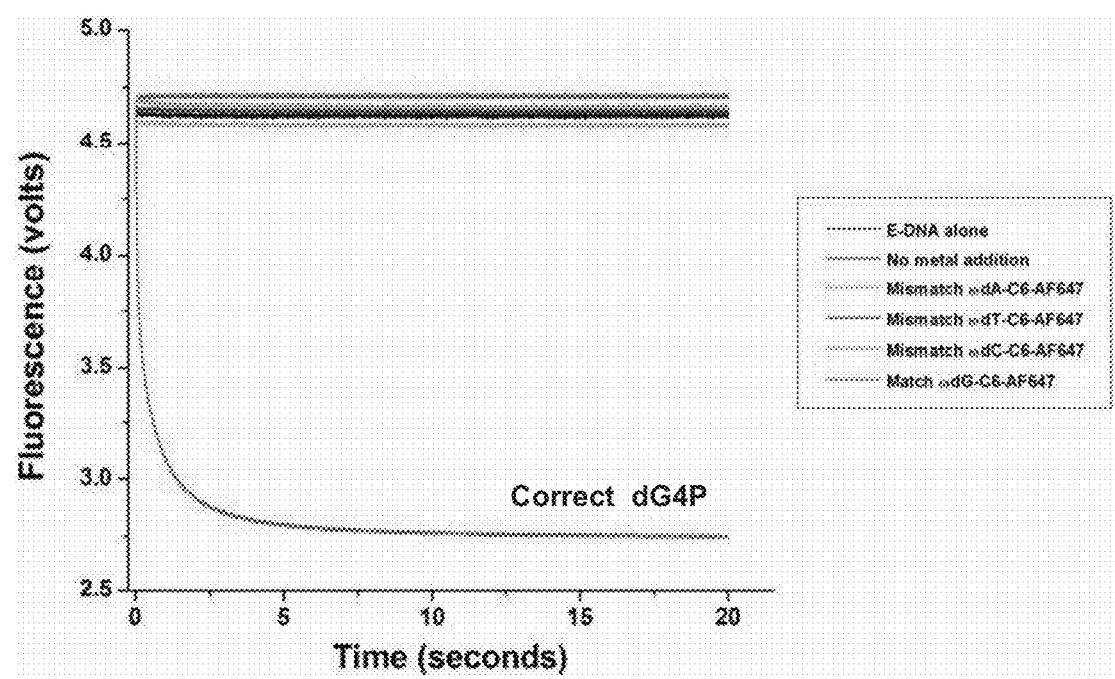
FIG. 9F shows stopped-flow fluorescence traces ($t_{pol}$) for Phi29 (exo-) polymerase, and correct and incorrect terminal phosphate labeled dN4P nucleotides, in the presence of calcium (Example 2).

Stopped flow procedures were conducted to characterize the selective binding of the correct nucleotides by various polymerases for transiently-binding in the presence of calcium. The primer/template duplexes were ALEXA FLUOR 546-labeled at the 5' end. A representative stopped-flow fluorescent trace for Phi29 (5 mM CaCl$_2$, FIG. 9F), reacted with one of four terminal phosphate labeled nucleotides (at 7 µM, labeled with AF647) is shown. The correct nucleotide is dG4P. The results show that Phi29 polymerase is selective in transient-binding the correct nucleotide, in the presence of calcium.

The apparent nucleotide dissociation constant ($K_d^{app}$) for the Phi29 DNA polymerase in the presence of 2 mM calcium was measured in the stopped-flow procedure. A representative stopped-flow fluorescent trace for Phi29 reacted with zero to 20 µM of the correct terminal phosphate labeled nucleotide (dG4P-AF647) is shown in FIG. 9G.

Figure 9G:
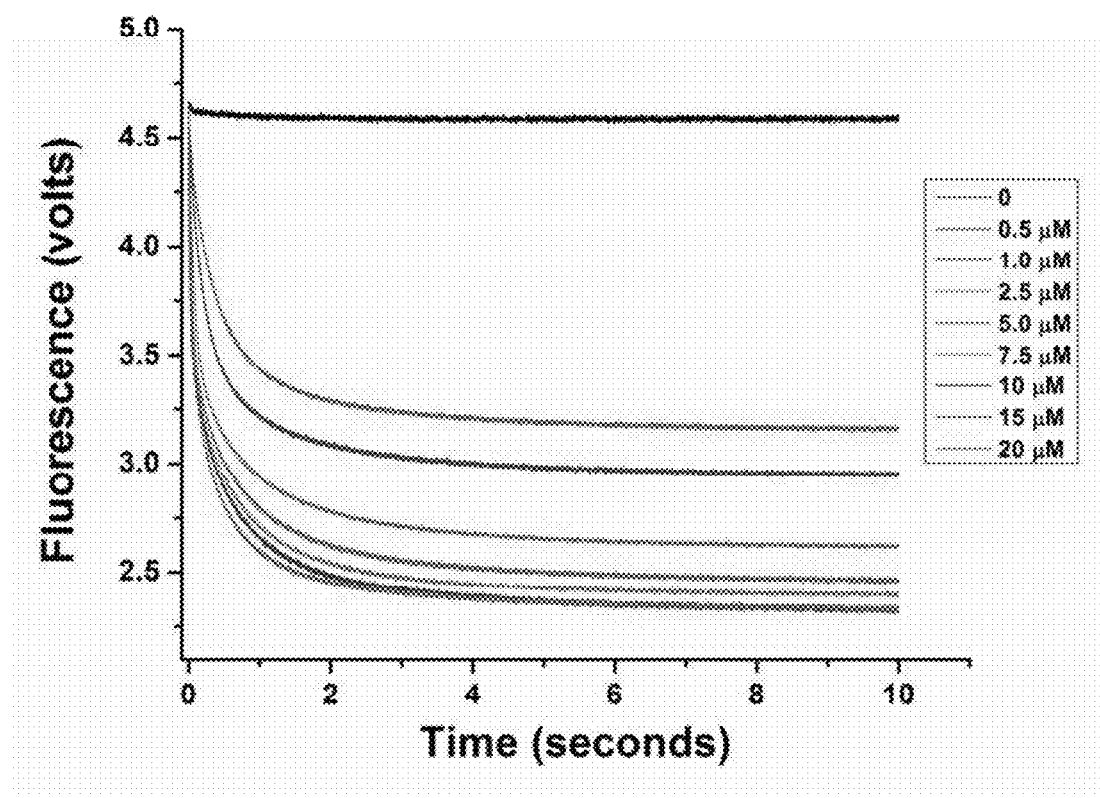
FIG. 9G shows stopped-flow fluorescence titration traces ($t_{pol}$) for Phi29 (exo-) polymerase and increasing amounts of the correct terminal phosphate labeled dN4P nucleotide in the presence of calcium (Example 2).

The averaged individual stopped-flow fluorescent trace (>1.5 msec) shown in FIG. 9G were fitted to a hyperbola equation 3 (H Zhang 2007 Nucleic Acids Research, pp. 1-11, doi:10.1093/nar/gkm587) to extrapolate the apparent nucleotide dissociation constant ($K_d^{app}$) for the Phi29 DNA polymerase.

$$\text{Fluorescence} = \frac{F_{max} \cdot [\text{nucleotide}]}{K_d^{app} + [\text{nucleotide}]} \quad \text{(equation 3)}$$

where $F_{max}$ represents the maximum fluorescence change, [nucleotide] is the concentration of nucleotide in the reaction, and $K_d^{app}$ is the apparent nucleotide dissociation constant.

Figure 9H:
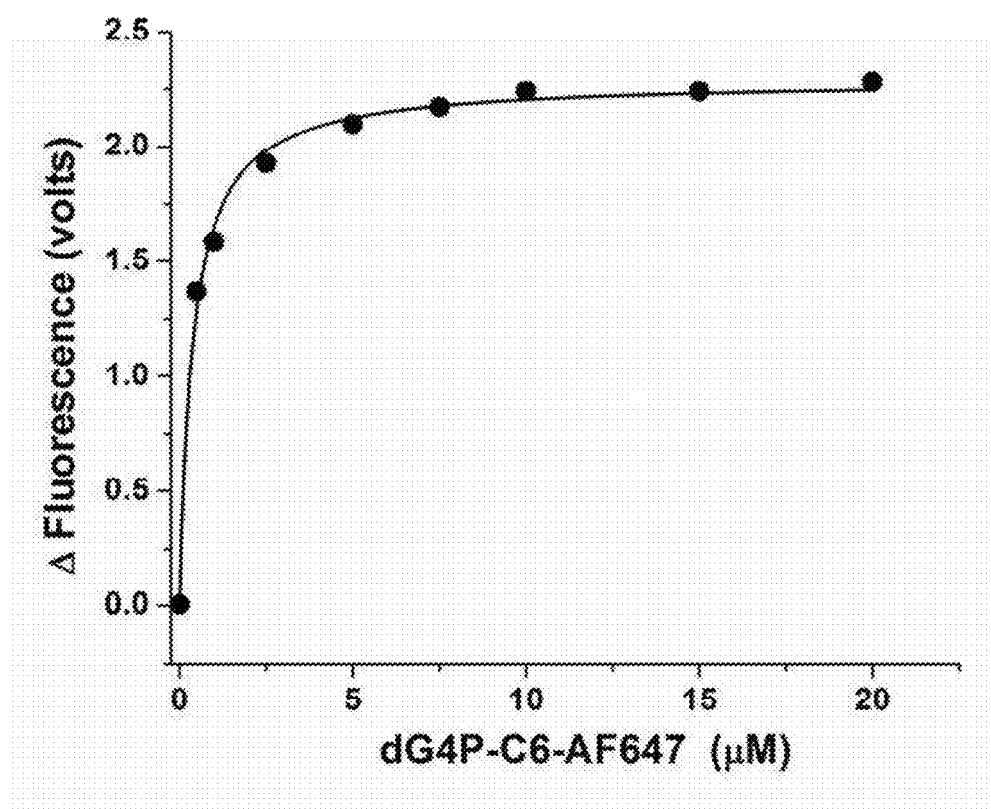
FIG. 9H shows data from FIG. 7E which is fitted to a hyperbola equation to extrapolate the apparent nucleotide dissociation constant ($k_d^{app}$) for Phi29 DNA polymerase (see Example 2).

The fitted data is shown in FIG. 9H. For Phi29 (exo-) polymerase, in the presence of 2 mM $CaCl_2$, the $K_d^{app}$ is about 0.38±0.03 µM.

4) RB69 Polymerase: Stopped Flow Measurements of $t_{pol}$

Figure 10A:
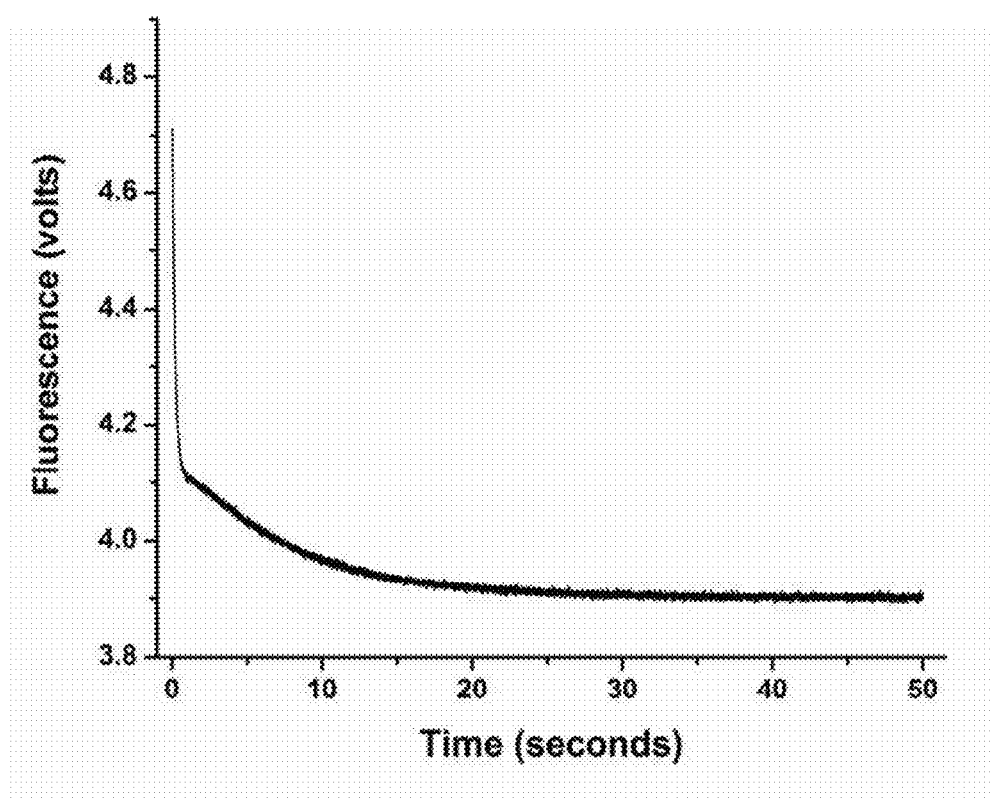
FIG. 10A shows a stopped-flow fluorescence trace ($t_{pol}$) for RB69 (exo-) polymerase and terminal phosphate labeled dN4P nucleotides in the presence of manganese (Example 2).
Figure 10B:
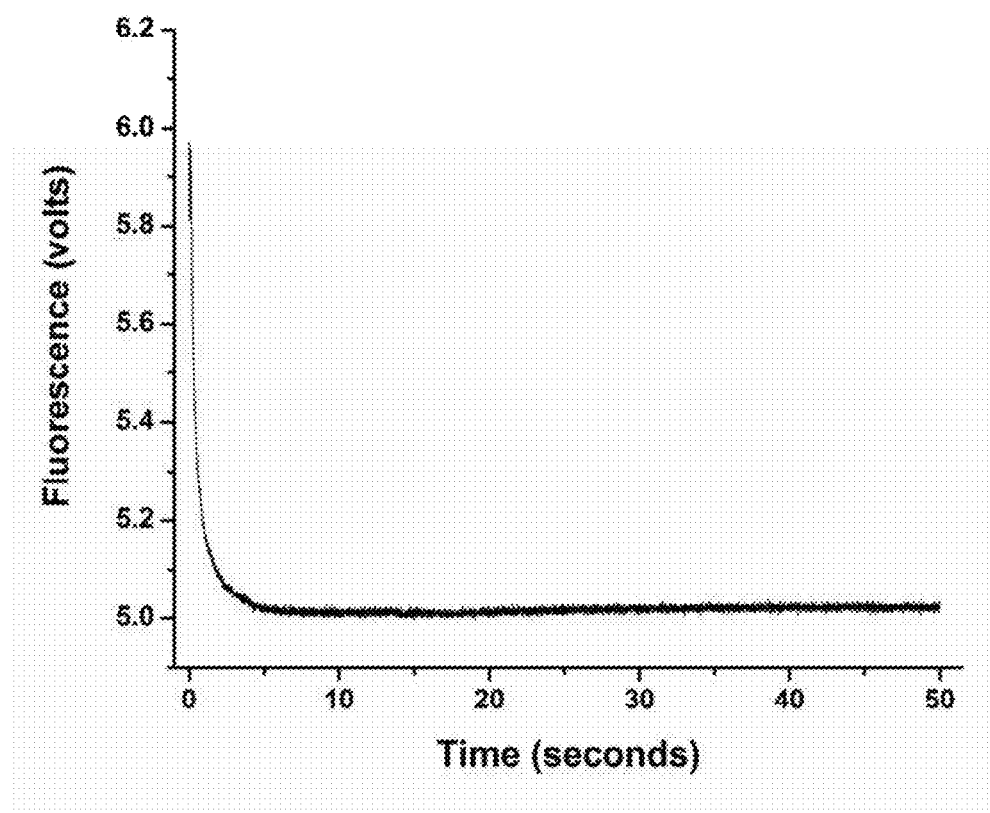
FIG. 10B shows a stopped-flow fluorescence trace ($t_{pol}$) for RB69 (exo-) polymerase and terminal phosphate labeled dN4P nucleotides in the presence of calcium (Example 2).

Stopped-flow measurements of $t_{pol}$ were conducted as described in the section above, using the A1, C1, T1 or G1 oligo-template sequences, and the same reaction conditions (see Example 3, section 1 above). Representative $t_{pol}$ stopped-flow fluorescence traces for RB69 polymerase in the presence of 2 mM manganese (FIG. 10A) or 10 mM calcium (FIG. 10B) are shown. The results show that RB69 polymerase binds the correct nucleotide but does not catalyze nucleotide incorporation in the presence of manganese (FIG. 10A).

5) RB69 Polymerase: Stopped Flow Measurements of $t_{-1}$

Figure 10C:
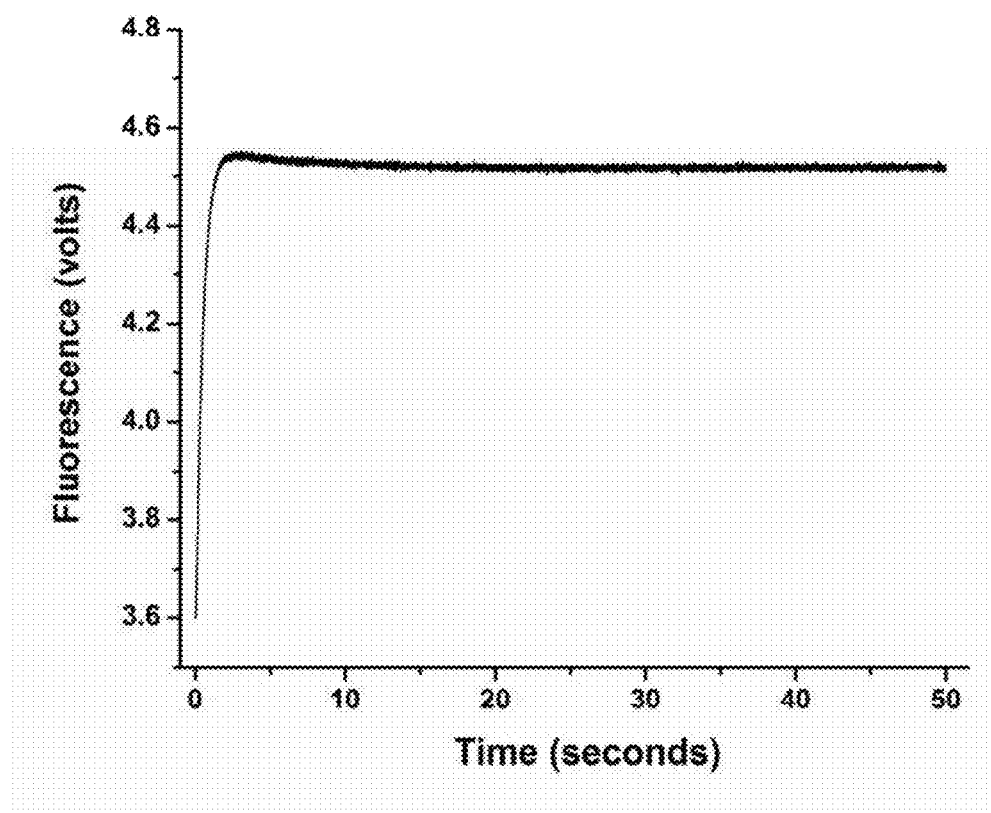
FIG. 10C shows a stopped-flow fluorescence trace ($t_{-1}$) for RB69 (exo-) polymerase and terminal phosphate labeled dN4P nucleotides in the presence of manganese (Example 2).
Figure 10D:
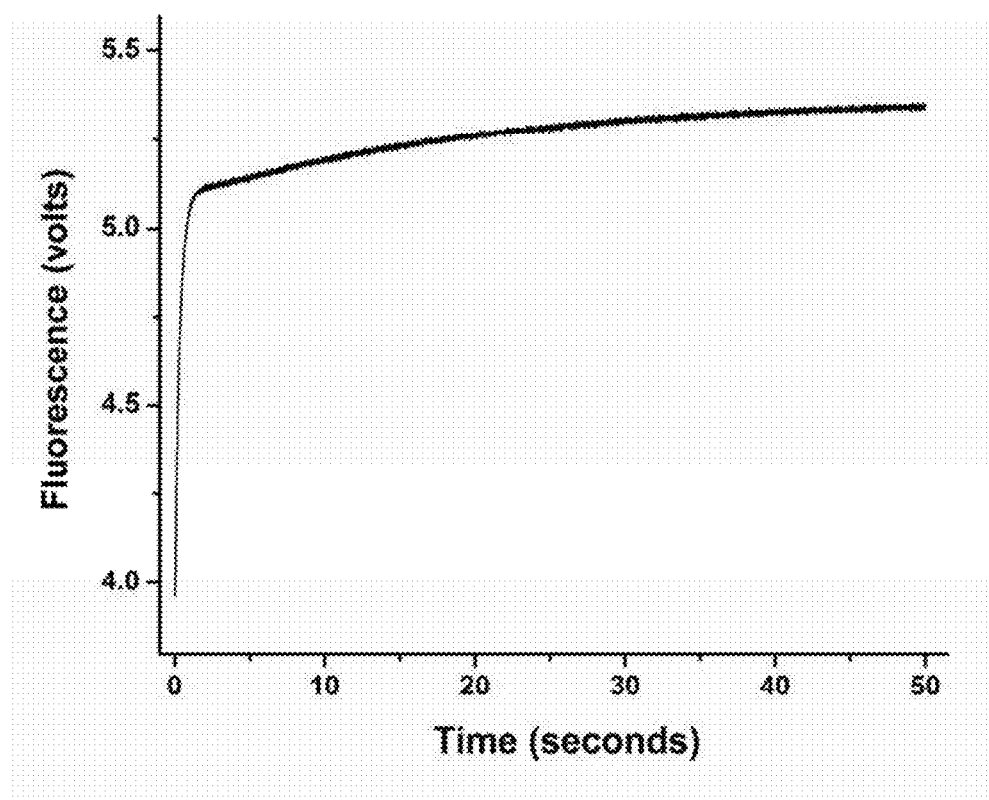
FIG. 10D shows a stopped-flow fluorescence trace ($t_{-1}$) for RB69 (exo-) polymerase and terminal phosphate labeled dN4P nucleotides in the presence of calcium (Example 2).

Stopped-flow measurements of $t_{-1}$ were conducted as described in the section above, using the A2, C2, T2, or G2 oligo-template sequences, and the same reaction conditions (see Example 3, section 2 above). Representative $t_{-1}$ stopped-flow fluorescence traces for RB69 polymerase in the presence of manganese (2 mM, FIG. 10C) or calcium (10 mM, FIG. 10D) are shown.

Figure 10E:
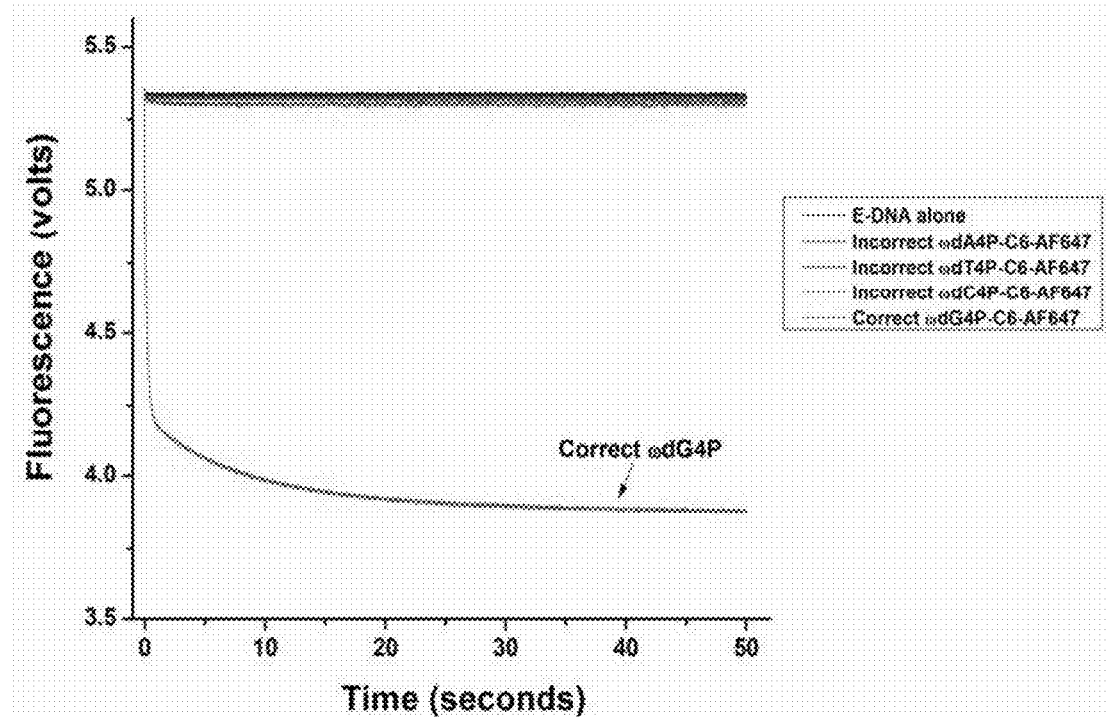
FIG. 10E shows stopped-flow fluorescence traces ($t_{pol}$) for RB69 (exo-) polymerase, and correct and incorrect terminal phosphate labeled dN4P nucleotides, in the presence of calcium (Example 2).

6) RB69 Polymerase: Stopped-Flow Measurements for Characterizing Nucleotide Transient-Binding:

Stopped flow procedures were conducted to characterize the selective binding of the correct nucleotides by RB69 polymerase for transiently-binding in the presence of calcium, as described above using the primer/template duplexes which were ALEXA FLUOR 546-labeled at the 5' end (see Example 3, section 3 above). A representative stopped-flow fluorescent trace for RB69 polymerase (10 mM $CaCl_2$, FIG. 10E), reacted with one of four terminal phosphate labeled nucleotides (at 7 µM, labeled with AF647) is shown. The correct nucleotide is dG4P. The results show that RB69 polymerase is selective in transient-binding the correct nucleotide, in the presence of calcium.

Example 3

Transient Binding Methods Using a Mutant RB69 Polymerase

In this example, the nucleotide transient-binding reaction and nucleotide incorporation reactions were conducted with a mutant RB69 polymerase (3PDX), using a donor-labeled hairpin template, and acceptor-labeled nucleotides. The nucleotide incorporation reactions were conducted with unlabeled 3'-azidomethyl terminator nucleotides.

```
Hairpin template sequence:
                                      (SEQ ID NO: 11)
5'-Cy3-CAGTCTCGGGATCTTGTGCCATT(biotin-dT)TTTGGCACA
AGATCCC-3'.
```

Wash Buffer: 50 mM Tris pH 7.5 (Invitrogen PN 15567-027), 50 mM NaCl, 0.2% Bovine Serum Albumin (Sigma PN A8577).

Reset Buffer: 50 mM Tris pH 7.5, 50 mM EDTA, 1 M NaCl, 0.2% BSA.

Imaging Solution: 50 mM Tris pH 7.5, 50 mM NaCl, 0.2% BSA, 1 uM 3PDX polymerase, 200 nM base-labeled nucleotides (AF647-aha-dUTP (Invitrogen, A32763), Cy5-propargylamine-dGTP (Jena Biosciences, NU-1615-CY5), AF5-propargylamine-dATP, or AF647-aha-dCTP (Invitrogen, A32771)), 0.4% glucose, 2 mM Trolox (Fluka PN 56510), 2-5 mM $CaCl_2$, 0.2 mg/mL glucose oxidase (Sigma PN G7141), 4 unit/µL Katalase (Fluka PN 02071).

1) Template Immobilization:

Flow chambers were assembled using PEG-biotin coated glass coverslips (Microsurfaces Inc., BIO 01). The flow chambers were washed with 1 mL of Wash Buffer. The flow chambers were injected with 5 nM streptavidin (in Wash Buffer) and incubated for 20 minutes. The flow chambers were rinsed with 1 mL Wash Buffer. The flow chambers were injected with 50 µM biotin-tagged DNA-Cy3 into the flow and incubated for 10 minutes. The flow chambers were washed with 1 mL Wash Buffer.

2) Nucleotide Transient-Binding Reaction:

The flow chambers were washed with 1 mL Wash Buffer. The flow chambers were injected with Imaging Solution containing one of the four dye-labeled nucleotides (e.g., dUTP), incubated for 3 minutes at room temperature, and imaged. Imaging was conducted by exciting at 532 nm at 50 W/cm². The acceptor signals were detected at 670 nm with a bandwidth of 30 nm. The 3 minute incubating step, and the imaging step, was repeated twice for a total of three incubation and three imaging steps for each type of labeled nucleotide. The flow chambers were not washed prior to injecting and imaging the other types labeled nucleotides. For the other three types of nucleotides (e.g., dATP, dGTP, dCTP), the flow chambers were injected with Imaging Solution containing dye-labeled nucleotides, and the incubating and imaging steps were repeated.

3) Nucleotide Incorporation:

The flow chambers were washed with 1 mL Reset Buffer. The flow chambers were washed with 1 mL Wash Buffer. The flow chambers were injected with 100 ul THERMINATOR Buffer (NEB, PN B9004S). The flow chambers were injected with 60 ul reversible terminator reaction mix containing four types of nucleotides having the 3' position of the sugar moiety blocked with an azidomethyl group; the reversible terminator reaction mix contained: 5 uM 3'-AM-dATP, 5 uM 3'-AM-dGTP, 2.5 uM 3'-AM-dCTP, 2.5 uM 3'-AM-dTTP, 1× THERMINATOR Buffer (NEB, PN B9004S), and 3 uM 3PDX polymerase. The flow chambers were incubated at room temperature for 45 minutes. The flow chambers were washed with 1 mL Reset Buffer. The flow chambers were washed with 1 mL Wash Buffer. The flow chambers were injected with 85 ul of 100 mM TCEP (Tris(2-carboxyethyl)phosphine) in 0.1 M Tris-HCL at pH 7.5, and allowed to incubate at room temperature for 20 minutes. The flow chambers were washed with 1 mL Reset Buffer. The nucleotide transient-binding and nucleotide incorporation reactions were repeated four times.

Mutant polymerases having the amino acid sequence of SEQ ID NO: 2, SEQ ID NO: 3, SEQ ID NO:4, SEQ ID NO:5, SEQ ID NO:6, SEQ ID NO:7 and SEQ ID NO:8 were separately tested for nucleotide binding and nucleotide incorporation activity in assays conducted according to the above-described procedures. The results indicated that some of these mutant polymerases (e.g., 3PDX) exhibited increased duration of nucleotide binding and increased nucleotide incorporation activity relative to wild type RB69 polymerase (data not shown).

---

What is claimed:

1. A system comprising a mutant DNA polymerase bound to a DNA template and a primer, and a nucleotide transiently-bound to the mutant DNA polymerase, wherein the mutant DNA polymerase comprises the amino acid of SEQ ID NO:2.

2. The system of claim 1, further comprising a metal cation that inhibits incorporation of the transiently-bound nucleotide.

3. The system of claim 2, wherein the metal cation is selected from a group consisting of calcium, scandium, titanium, vanadium, chromium, iron, cobalt, nickel, copper, zinc, gallium, germanium, arsenic, and selenium.

4. The system of claim 1, wherein the transiently-bound nucleotide is linked to a report moiet.

5. The system of claim 1, wherein the mutant DNA polymerase further comprises a reporter moiety.

6. The system of claim 5, wherein the reporter moiety comprises an energy transfer donor moiety.

7. The system of claim 5, wherein the reporter moiety comprises a fluorescent dye or a nanoparticle.

8. The system of claim 1, wherein the transiently-bound nucleotide comprises a reversible terminator nucleotide.

9. The system of claim 8, wherein the reversible terminator nucleotide comprises an azidomethyl blocking group on the 3' sugar position.

* * * * *

SEQUENCE LISTING

```
<160> NUMBER OF SEQ ID NOS: 23

<210> SEQ ID NO 1
<211> LENGTH: 903
<212> TYPE: PRT
<213> ORGANISM: Unknown
<220> FEATURE:
<223> OTHER INFORMATION: Description of Unknown: Enterobacteria phage
      RB69 polypeptide

<400> SEQUENCE: 1

Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Arg Thr Arg Glu Val Glu
            20                  25                  30

Tyr Lys Pro Ser Leu Phe Ala His Cys Pro Glu Ser Gln Ala Thr Lys
        35                  40                  45

Tyr Phe Asp Ile Tyr Gly Lys Pro Cys Thr Arg Lys Leu Phe Ala Asn
    50                  55                  60

Met Arg Asp Ala Ser Gln Trp Ile Lys Arg Met Glu Asp Ile Gly Leu
65                  70                  75                  80

Glu Ala Leu Gly Met Asp Asp Phe Lys Leu Ala Tyr Leu Ser Asp Thr
                85                  90                  95

Tyr Asn Tyr Glu Ile Lys Tyr Asp His Thr Lys Ile Arg Val Ala Asn
            100                 105                 110

Phe Asp Ile Glu Val Thr Ser Pro Asp Gly Phe Pro Glu Pro Ser Gln
        115                 120                 125

Ala Lys His Pro Ile Asp Ala Ile Thr His Tyr Asp Ser Ile Asp Asp
    130                 135                 140

Arg Phe Tyr Val Phe Asp Leu Leu Asn Ser Pro Tyr Gly Asn Val Glu
145                 150                 155                 160

Glu Trp Ser Ile Glu Ile Ala Ala Lys Leu Gln Glu Gln Gly Gly Asp
                165                 170                 175

Glu Val Pro Ser Glu Ile Ile Asp Lys Ile Ile Tyr Met Pro Phe Asp
            180                 185                 190

Asn Glu Lys Glu Leu Leu Met Glu Tyr Leu Asn Phe Trp Gln Gln Lys
        195                 200                 205

Thr Pro Val Ile Leu Thr Gly Trp Asn Val Glu Ser Phe Asp Ile Pro
    210                 215                 220

Tyr Val Tyr Asn Arg Ile Lys Asn Ile Phe Gly Glu Ser Thr Ala Lys
225                 230                 235                 240

Arg Leu Ser Pro His Arg Lys Thr Arg Val Lys Val Ile Glu Asn Met
                245                 250                 255

Tyr Gly Ser Arg Glu Ile Ile Thr Leu Phe Gly Ile Ser Val Leu Asp
            260                 265                 270

Tyr Ile Asp Leu Tyr Lys Lys Phe Ser Phe Thr Asn Gln Pro Ser Tyr
        275                 280                 285

Ser Leu Asp Tyr Ile Ser Glu Phe Glu Leu Asn Val Gly Lys Leu Lys
    290                 295                 300
```

```
Tyr Asp Gly Pro Ile Ser Lys Leu Arg Glu Ser Asn His Gln Arg Tyr
305                 310                 315                 320

Ile Ser Tyr Asn Ile Ile Asp Val Tyr Arg Val Leu Gln Ile Asp Ala
            325                 330                 335

Lys Arg Gln Phe Ile Asn Leu Ser Leu Asp Met Gly Tyr Tyr Ala Lys
                340                 345                 350

Ile Gln Ile Gln Ser Val Phe Ser Pro Ile Lys Thr Trp Asp Ala Ile
        355                 360                 365

Ile Phe Asn Ser Leu Lys Glu Gln Asn Lys Val Ile Pro Gln Gly Arg
    370                 375                 380

Ser His Pro Val Gln Pro Tyr Pro Gly Ala Phe Val Lys Glu Pro Ile
385                 390                 395                 400

Pro Asn Arg Tyr Lys Tyr Val Met Ser Phe Asp Leu Thr Ser Leu Tyr
                405                 410                 415

Pro Ser Ile Ile Arg Gln Val Asn Ile Ser Pro Glu Thr Ile Ala Gly
                420                 425                 430

Thr Phe Lys Val Ala Pro Leu His Asp Tyr Ile Asn Ala Val Ala Glu
        435                 440                 445

Arg Pro Ser Asp Val Tyr Ser Cys Ser Pro Asn Gly Met Met Tyr Tyr
450                 455                 460

Lys Asp Arg Asp Gly Val Val Pro Thr Glu Ile Thr Lys Val Phe Asn
465                 470                 475                 480

Gln Arg Lys Glu His Lys Gly Tyr Met Leu Ala Ala Gln Arg Asn Gly
                485                 490                 495

Glu Ile Ile Lys Glu Ala Leu His Asn Pro Asn Leu Ser Val Asp Glu
                500                 505                 510

Pro Leu Asp Val Asp Tyr Arg Phe Asp Phe Ser Asp Glu Ile Lys Glu
                515                 520                 525

Lys Ile Lys Lys Leu Ser Ala Lys Ser Leu Asn Glu Met Leu Phe Arg
530                 535                 540

Ala Gln Arg Thr Glu Val Ala Gly Met Thr Ala Gln Ile Asn Arg Lys
545                 550                 555                 560

Leu Leu Ile Asn Ser Leu Tyr Gly Ala Leu Gly Asn Val Trp Phe Arg
                565                 570                 575

Tyr Tyr Asp Leu Arg Asn Ala Thr Ala Ile Thr Thr Phe Gly Gln Met
            580                 585                 590

Ala Leu Gln Trp Ile Glu Arg Lys Val Asn Glu Tyr Leu Asn Glu Val
        595                 600                 605

Cys Gly Thr Glu Gly Glu Ala Phe Val Leu Tyr Gly Asp Thr Asp Ser
610                 615                 620

Ile Tyr Val Ser Ala Asp Lys Ile Ile Asp Lys Val Gly Glu Ser Lys
625                 630                 635                 640

Phe Arg Asp Thr Asn His Trp Val Asp Phe Leu Asp Lys Phe Ala Arg
            645                 650                 655

Glu Arg Met Glu Pro Ala Ile Asp Arg Gly Phe Arg Glu Met Cys Glu
                660                 665                 670

Tyr Met Asn Asn Lys Gln His Leu Met Phe Met Asp Arg Glu Ala Ile
            675                 680                 685

Ala Gly Pro Pro Leu Gly Ser Lys Gly Ile Gly Gly Phe Trp Thr Gly
        690                 695                 700

Lys Lys Arg Tyr Ala Leu Asn Val Trp Asp Met Glu Gly Thr Arg Tyr
705                 710                 715                 720

Ala Glu Pro Lys Leu Lys Ile Met Gly Leu Glu Thr Gln Lys Ser Ser
```

```
                725                 730                 735

Thr Pro Lys Ala Val Gln Lys Ala Leu Lys Glu Cys Ile Arg Arg Met
        740                 745                 750

Leu Gln Glu Gly Glu Glu Ser Leu Gln Glu Tyr Phe Lys Glu Phe Glu
            755                 760                 765

Lys Glu Phe Arg Gln Leu Asn Tyr Ile Ser Ile Ala Ser Val Ser Ser
    770                 775                 780

Ala Asn Asn Ile Ala Lys Tyr Asp Val Gly Phe Pro Gly Pro Lys
785                 790                 795                 800

Cys Pro Phe His Ile Arg Gly Ile Leu Thr Tyr Asn Arg Ala Ile Lys
                805                 810                 815

Gly Asn Ile Asp Ala Pro Gln Val Val Glu Gly Lys Val Tyr Val
            820                 825                 830

Leu Pro Leu Arg Glu Gly Asn Pro Phe Gly Asp Lys Cys Ile Ala Trp
        835                 840                 845

Pro Ser Gly Thr Glu Ile Thr Asp Leu Ile Lys Asp Val Leu His
    850                 855                 860

Trp Met Asp Tyr Thr Val Leu Leu Glu Lys Thr Phe Ile Lys Pro Leu
865                 870                 875                 880

Glu Gly Phe Thr Ser Ala Ala Lys Leu Asp Tyr Glu Lys Lys Ala Ser
                885                 890                 895

Leu Phe Asp Met Phe Asp Phe
            900

<210> SEQ ID NO 2
<211> LENGTH: 903
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Arg Thr Arg Glu Val Glu
            20                  25                  30

Tyr Lys Pro Ser Leu Phe Ala His Cys Pro Glu Ser Gln Ala Thr Lys
        35                  40                  45

Tyr Phe Asp Ile Tyr Gly Lys Pro Cys Thr Arg Lys Leu Phe Ala Asn
    50                  55                  60

Met Arg Asp Ala Ser Gln Trp Ile Lys Arg Met Glu Asp Ile Gly Leu
65                  70                  75                  80

Glu Ala Leu Gly Met Asp Asp Phe Lys Leu Ala Tyr Leu Ser Asp Thr
                85                  90                  95

Tyr Asn Tyr Glu Ile Lys Tyr Asp His Thr Lys Ile Arg Val Ala Asn
            100                 105                 110

Phe Asp Ile Glu Val Thr Ser Pro Asp Gly Phe Pro Glu Pro Ser Gln
        115                 120                 125

Ala Lys His Pro Ile Asp Ala Ile Thr His Tyr Asp Ser Ile Asp Asp
    130                 135                 140

Arg Phe Tyr Val Phe Asp Leu Leu Asn Ser Pro Tyr Gly Asn Val Glu
145                 150                 155                 160

Glu Trp Ser Ile Glu Ile Ala Ala Lys Leu Gln Glu Gln Gly Gly Asp
                165                 170                 175
```

-continued

Glu Val Pro Ser Glu Ile Ile Asp Lys Ile Ile Tyr Met Pro Phe Asp
            180                 185                 190

Asn Glu Lys Glu Leu Leu Met Glu Tyr Leu Asn Phe Trp Gln Gln Lys
        195                 200                 205

Thr Pro Val Ile Leu Thr Gly Trp Asn Val Glu Ser Phe Ala Ile Pro
    210                 215                 220

Tyr Val Tyr Asn Arg Ile Lys Asn Ile Phe Gly Glu Ser Thr Ala Lys
225                 230                 235                 240

Arg Leu Ser Pro His Arg Lys Thr Arg Val Lys Val Ile Glu Asn Met
                245                 250                 255

Tyr Gly Ser Arg Glu Ile Ile Thr Leu Phe Gly Ile Ser Val Leu Asp
            260                 265                 270

Tyr Ile Asp Leu Tyr Lys Lys Phe Ser Phe Thr Asn Gln Pro Ser Tyr
        275                 280                 285

Ser Leu Asp Tyr Ile Ser Glu Phe Glu Leu Asn Val Gly Lys Leu Lys
    290                 295                 300

Tyr Asp Gly Pro Ile Ser Lys Leu Arg Glu Ser Asn His Gln Arg Tyr
305                 310                 315                 320

Ile Ser Tyr Asn Ile Ile Ala Val Tyr Arg Val Leu Gln Ile Asp Ala
                325                 330                 335

Lys Arg Gln Phe Ile Asn Leu Ser Leu Asp Met Gly Tyr Tyr Ala Lys
            340                 345                 350

Ile Gln Ile Gln Ser Val Phe Ser Pro Ile Lys Thr Trp Asp Ala Ile
        355                 360                 365

Ile Phe Asn Ser Leu Lys Glu Gln Asn Lys Val Ile Pro Gln Gly Arg
    370                 375                 380

Ser His Pro Val Gln Pro Tyr Pro Gly Ala Phe Val Lys Glu Pro Ile
385                 390                 395                 400

Pro Asn Arg Tyr Lys Tyr Val Met Ser Phe Asp Leu Thr Ser Ser Ala
                405                 410                 415

Val Ser Ile Ile Arg Gln Val Asn Ile Ser Pro Glu Thr Ile Ala Gly
            420                 425                 430

Thr Phe Lys Val Ala Pro Leu His Asp Tyr Ile Asn Ala Val Ala Glu
        435                 440                 445

Arg Pro Ser Asp Val Tyr Ser Cys Ser Pro Asn Gly Met Met Tyr Tyr
    450                 455                 460

Lys Asp Arg Asp Gly Val Pro Thr Glu Ile Thr Lys Val Phe Asn
465                 470                 475                 480

Gln Arg Lys Glu His Lys Gly Tyr Met Leu Ala Ala Gln Arg Asn Gly
                485                 490                 495

Glu Ile Ile Lys Glu Ala Leu His Asn Pro Asn Leu Ser Val Asp Glu
            500                 505                 510

Pro Leu Asp Val Asp Tyr Arg Phe Asp Phe Ser Asp Glu Ile Lys Glu
        515                 520                 525

Lys Ile Lys Lys Leu Ser Ala Lys Ser Leu Asn Glu Met Leu Phe Arg
    530                 535                 540

Ala Gln Arg Thr Glu Val Ala Gly Met Thr Ala Gln Ile Asn Arg Lys
545                 550                 555                 560

Leu Leu Ile Asn Ser Leu Tyr Gly Ala Leu Gly Asn Val Trp Phe Arg
                565                 570                 575

Tyr Tyr Asp Leu Arg Asn Ala Thr Ala Ile Thr Thr Phe Gly Gln Met
            580                 585                 590

Ala Leu Gln Trp Ile Glu Arg Lys Val Asn Glu Tyr Leu Asn Glu Val

```
                595                 600                 605
Cys Gly Thr Glu Gly Glu Ala Phe Val Leu Tyr Gly Asp Thr Asp Ser
610                 615                 620

Ile Tyr Val Ser Ala Asp Lys Ile Ile Asp Lys Val Gly Glu Ser Lys
625                 630                 635                 640

Phe Arg Asp Thr Asn His Trp Val Asp Phe Leu Asp Lys Phe Ala Arg
                645                 650                 655

Glu Arg Met Glu Pro Ala Ile Asp Arg Gly Phe Arg Glu Met Cys Glu
            660                 665                 670

Tyr Met Asn Asn Lys Gln His Leu Met Phe Met Asp Arg Glu Ala Ile
        675                 680                 685

Ala Gly Pro Pro Leu Gly Ser Lys Gly Ile Gly Gly Phe Trp Thr Gly
690                 695                 700

Lys Lys Arg Tyr Ala Leu Asn Val Trp Asp Met Glu Gly Thr Arg Tyr
705                 710                 715                 720

Ala Glu Pro Lys Leu Lys Ile Met Gly Leu Glu Thr Gln Lys Ser Ser
                725                 730                 735

Thr Pro Lys Ala Val Gln Lys Ala Leu Lys Glu Cys Ile Arg Arg Met
            740                 745                 750

Leu Gln Glu Gly Glu Glu Ser Leu Gln Glu Tyr Phe Lys Glu Phe Glu
        755                 760                 765

Lys Glu Phe Arg Gln Leu Asn Tyr Ile Ser Ile Ala Ser Val Ser Ser
770                 775                 780

Ala Asn Asn Ile Ala Lys Tyr Asp Val Gly Gly Phe Pro Gly Pro Lys
785                 790                 795                 800

Cys Pro Phe His Ile Arg Gly Ile Leu Thr Tyr Asn Arg Ala Ile Lys
                805                 810                 815

Gly Asn Ile Asp Ala Pro Gln Val Val Glu Gly Glu Lys Val Tyr Val
            820                 825                 830

Leu Pro Leu Arg Glu Gly Asn Pro Phe Gly Asp Lys Cys Ile Ala Trp
        835                 840                 845

Pro Ser Gly Thr Glu Ile Thr Asp Leu Ile Lys Asp Asp Val Leu His
850                 855                 860

Trp Met Asp Tyr Thr Val Leu Leu Glu Lys Thr Phe Ile Lys Pro Leu
865                 870                 875                 880

Glu Gly Phe Thr Ser Ala Ala Lys Leu Asp Tyr Glu Lys Lys Ala Ser
                885                 890                 895

Leu Phe Asp Met Phe Asp Phe
            900

<210> SEQ ID NO 3
<211> LENGTH: 903
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Arg Thr Arg Glu Val Glu
            20                  25                  30

Tyr Lys Pro Ser Leu Phe Ala His Cys Pro Glu Ser Gln Ala Thr Lys
        35                  40                  45
```

```
Tyr Phe Asp Ile Tyr Gly Lys Pro Cys Thr Arg Lys Leu Phe Ala Asn
     50                  55                  60

Met Arg Asp Ala Ser Gln Trp Ile Lys Arg Met Glu Asp Ile Gly Leu
 65                  70                  75                  80

Glu Ala Leu Gly Met Asp Asp Phe Lys Leu Ala Tyr Leu Ser Asp Thr
                 85                  90                  95

Tyr Asn Tyr Glu Ile Lys Tyr Asp His Thr Lys Ile Arg Val Ala Asn
                100                 105                 110

Phe Asp Ile Glu Val Thr Ser Pro Asp Gly Phe Pro Glu Pro Ser Gln
            115                 120                 125

Ala Lys His Pro Ile Asp Ala Ile Thr His Tyr Asp Ser Ile Asp Asp
130                 135                 140

Arg Phe Tyr Val Phe Asp Leu Leu Asn Ser Pro Tyr Gly Asn Val Glu
145                 150                 155                 160

Glu Trp Ser Ile Glu Ile Ala Ala Lys Leu Gln Glu Gln Gly Gly Asp
                165                 170                 175

Glu Val Pro Ser Glu Ile Ile Asp Lys Ile Ile Tyr Met Pro Phe Asp
                180                 185                 190

Asn Glu Lys Glu Leu Leu Met Glu Tyr Leu Asn Phe Trp Gln Gln Lys
                195                 200                 205

Thr Pro Val Ile Leu Thr Gly Trp Asn Val Glu Ser Phe Asp Ile Pro
210                 215                 220

Tyr Val Tyr Asn Arg Ile Lys Asn Ile Phe Gly Glu Ser Thr Ala Lys
225                 230                 235                 240

Arg Leu Ser Pro His Arg Lys Thr Arg Val Lys Val Ile Glu Asn Met
                245                 250                 255

Tyr Gly Ser Arg Glu Ile Ile Thr Leu Phe Gly Ile Ser Val Leu Asp
                260                 265                 270

Tyr Ile Asp Leu Tyr Lys Lys Phe Ser Phe Thr Asn Gln Pro Ser Tyr
            275                 280                 285

Ser Leu Asp Tyr Ile Ser Glu Phe Glu Leu Asn Val Gly Lys Leu Lys
            290                 295                 300

Tyr Asp Gly Pro Ile Ser Lys Leu Arg Glu Ser Asn His Gln Arg Tyr
305                 310                 315                 320

Ile Ser Tyr Asn Ile Ile Ala Val Tyr Arg Val Leu Gln Ile Asp Ala
                325                 330                 335

Lys Arg Gln Phe Ile Asn Leu Ser Leu Asp Met Gly Tyr Tyr Ala Lys
            340                 345                 350

Ile Gln Ile Gln Ser Val Phe Ser Pro Ile Lys Thr Trp Asp Ala Ile
            355                 360                 365

Ile Phe Asn Ser Leu Lys Glu Gln Asn Lys Val Ile Pro Gln Gly Arg
    370                 375                 380

Ser His Pro Val Gln Pro Tyr Pro Gly Ala Phe Val Lys Glu Pro Ile
385                 390                 395                 400

Pro Asn Arg Tyr Lys Tyr Val Met Ser Phe Asp Leu Thr Ser Leu Tyr
                405                 410                 415

Pro Ser Ile Ile Arg Gln Val Asn Ile Ser Pro Glu Thr Ile Ala Gly
            420                 425                 430

Thr Phe Lys Val Ala Pro Leu His Asp Tyr Ile Asn Ala Val Ala Glu
            435                 440                 445

Arg Pro Ser Asp Val Tyr Ser Cys Ser Pro Asn Gly Met Met Tyr Tyr
450                 455                 460

Lys Asp Arg Asp Gly Val Val Pro Thr Glu Ile Thr Lys Val Phe Asn
```

```
            465                 470                 475                 480
        Gln Arg Lys Glu His Lys Gly Tyr Met Leu Ala Ala Gln Arg Asn Gly
                        485                 490                 495

Glu Ile Ile Lys Glu Ala Leu His Asn Pro Asn Leu Ser Val Asp Glu
                    500                 505                 510

Pro Leu Asp Val Asp Tyr Arg Phe Asp Phe Ser Asp Glu Ile Lys Glu
                    515                 520                 525

Lys Ile Lys Lys Leu Ser Ala Lys Ser Leu Asn Glu Met Leu Phe Arg
                    530                 535                 540

Ala Gln Arg Thr Glu Val Ala Gly Met Thr Ala Gln Ile Asn Arg Lys
        545                 550                 555                 560

Leu Leu Ile Asn Ser Leu Tyr Gly Ala Leu Gly Asn Val Trp Phe Arg
                        565                 570                 575

Tyr Tyr Asp Leu Arg Asn Ala Thr Ala Ile Thr Thr Phe Gly Gln Met
                        580                 585                 590

Ala Leu Gln Trp Ile Glu Arg Lys Val Asn Glu Tyr Leu Asn Glu Val
                    595                 600                 605

Cys Gly Thr Glu Gly Glu Ala Phe Val Leu Tyr Gly Asp Thr Asp Ser
                    610                 615                 620

Ile Tyr Val Ser Ala Asp Lys Ile Ile Asp Lys Val Gly Glu Ser Lys
        625                 630                 635                 640

Phe Arg Asp Thr Asn His Trp Val Asp Phe Leu Asp Lys Phe Ala Arg
                        645                 650                 655

Glu Arg Met Glu Pro Ala Ile Asp Arg Gly Phe Arg Glu Met Cys Glu
                    660                 665                 670

Tyr Met Asn Asn Lys Gln His Leu Met Phe Met Asp Arg Glu Ala Ile
                    675                 680                 685

Ala Gly Pro Pro Leu Gly Ser Lys Gly Ile Gly Gly Phe Trp Thr Gly
                    690                 695                 700

Lys Lys Arg Tyr Ala Leu Asn Val Trp Asp Met Glu Gly Thr Arg Tyr
        705                 710                 715                 720

Ala Glu Pro Lys Leu Lys Ile Met Gly Leu Glu Thr Gln Lys Ser Ser
                        725                 730                 735

Thr Pro Lys Ala Val Gln Lys Ala Leu Lys Glu Cys Ile Arg Arg Met
                        740                 745                 750

Leu Gln Glu Gly Glu Glu Ser Leu Gln Glu Tyr Phe Lys Glu Phe Glu
                    755                 760                 765

Lys Glu Phe Arg Gln Leu Asn Tyr Ile Ser Ile Ala Ser Val Ser Ser
                    770                 775                 780

Ala Asn Asn Ile Ala Lys Tyr Asp Val Gly Gly Phe Pro Gly Pro Lys
        785                 790                 795                 800

Cys Pro Phe His Ile Arg Gly Ile Leu Thr Tyr Asn Arg Ala Ile Lys
                        805                 810                 815

Gly Asn Ile Asp Ala Pro Gln Val Val Glu Gly Glu Lys Val Tyr Val
                        820                 825                 830

Leu Pro Leu Arg Glu Gly Asn Pro Phe Gly Asp Lys Cys Ile Ala Trp
                    835                 840                 845

Pro Ser Gly Thr Glu Ile Thr Asp Leu Ile Lys Asp Asp Val Leu His
                    850                 855                 860

Trp Met Asp Tyr Thr Val Leu Leu Glu Lys Thr Phe Ile Lys Pro Leu
        865                 870                 875                 880

Glu Gly Phe Thr Ser Ala Ala Lys Leu Asp Tyr Glu Lys Lys Ala Ser
                        885                 890                 895
```

```
Leu Phe Asp Met Phe Asp Phe
            900

<210> SEQ ID NO 4
<211> LENGTH: 903
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Lys Glu Phe Tyr Leu Thr Val Gln Ile Gly Asp Ser Ile Phe
1               5                   10                  15

Glu Arg Tyr Ile Asp Ser Asn Gly Arg Glu Arg Thr Arg Glu Val Glu
                20                  25                  30

Tyr Lys Pro Ser Leu Phe Ala His Cys Pro Glu Ser Gln Ala Thr Lys
            35                  40                  45

Tyr Phe Asp Ile Tyr Gly Lys Pro Cys Thr Arg Lys Leu Phe Ala Asn
    50                  55                  60

Met Arg Asp Ala Ser Gln Trp Ile Lys Arg Met Glu Asp Ile Gly Leu
65                  70                  75                  80

Glu Ala Leu Gly Met Asp Asp Phe Lys Leu Ala Tyr Leu Ser Asp Thr
                85                  90                  95

Tyr Asn Tyr Glu Ile Lys Tyr Asp His Thr Lys Ile Arg Val Ala Asn
            100                 105                 110

Phe Asp Ile Glu Val Thr Ser Pro Asp Gly Phe Pro Glu Pro Ser Gln
        115                 120                 125

Ala Lys His Pro Ile Asp Ala Ile Thr His Tyr Asp Ser Ile Asp Asp
    130                 135                 140

Arg Phe Tyr Val Phe Asp Leu Leu Asn Ser Pro Tyr Gly Asn Val Glu
145                 150                 155                 160

Glu Trp Ser Ile Glu Ile Ala Ala Lys Leu Gln Glu Gln Gly Gly Asp
                165                 170                 175

Glu Val Pro Ser Glu Ile Ile Asp Lys Ile Ile Tyr Met Pro Phe Asp
            180                 185                 190

Asn Glu Lys Glu Leu Leu Met Glu Tyr Leu Asn Phe Trp Gln Gln Lys
        195                 200                 205

Thr Pro Val Ile Leu Thr Gly Trp Asn Val Glu Ser Phe Ala Ile Pro
    210                 215                 220

Tyr Val Tyr Asn Arg Ile Lys Asn Ile Phe Gly Glu Ser Thr Ala Lys
225                 230                 235                 240

Arg Leu Ser Pro His Arg Lys Thr Arg Val Lys Val Ile Glu Asn Met
                245                 250                 255

Tyr Gly Ser Arg Glu Ile Ile Thr Leu Phe Gly Ile Ser Val Leu Asp
            260                 265                 270

Tyr Ile Asp Leu Tyr Lys Lys Phe Ser Phe Thr Asn Gln Pro Ser Tyr
        275                 280                 285

Ser Leu Asp Tyr Ile Ser Glu Phe Glu Leu Asn Val Gly Lys Leu Lys
    290                 295                 300

Tyr Asp Gly Pro Ile Ser Lys Leu Arg Glu Ser Asn His Gln Arg Tyr
305                 310                 315                 320

Ile Ser Tyr Asn Ile Ile Ala Val Tyr Arg Val Leu Gln Ile Asp Ala
                325                 330                 335

Lys Arg Gln Phe Ile Asn Leu Ser Leu Asp Met Gly Tyr Tyr Ala Lys
```

```
                340                 345                 350
Ile Gln Ile Gln Ser Val Phe Ser Pro Ile Lys Thr Trp Asp Ala Ile
            355                 360                 365
Ile Phe Asn Ser Leu Lys Glu Gln Asn Lys Val Ile Pro Gln Gly Arg
        370                 375                 380
Ser His Pro Val Gln Pro Tyr Pro Gly Ala Phe Val Lys Glu Pro Ile
385                 390                 395                 400
Pro Asn Arg Tyr Lys Tyr Val Met Ser Phe Asp Leu Thr Ser Leu Tyr
                405                 410                 415
Pro Ser Ile Ile Arg Gln Val Asn Ile Ser Pro Glu Thr Ile Ala Gly
            420                 425                 430
Thr Phe Lys Val Ala Pro Leu His Asp Tyr Ile Asn Ala Val Ala Glu
        435                 440                 445
Arg Pro Ser Asp Val Tyr Ser Cys Ser Pro Asn Gly Met Met Tyr Tyr
    450                 455                 460
Lys Asp Arg Asp Gly Val Val Pro Thr Glu Ile Thr Lys Val Phe Asn
465                 470                 475                 480
Gln Arg Lys Glu His Lys Gly Tyr Met Leu Ala Ala Gln Arg Asn Gly
                485                 490                 495
Glu Ile Ile Lys Glu Ala Leu His Asn Pro Asn Leu Ser Val Asp Glu
            500                 505                 510
Pro Leu Asp Val Asp Tyr Arg Phe Asp Phe Ser Asp Glu Ile Lys Glu
        515                 520                 525
Lys Ile Lys Lys Leu Ser Ala Lys Ser Leu Asn Glu Met Leu Phe Arg
    530                 535                 540
Ala Gln Arg Thr Glu Val Ala Gly Met Thr Ala Gln Ile Asn Arg Lys
545                 550                 555                 560
Leu Leu Ile Asn Ser Leu Tyr Gly Ala Leu Gly Asn Val Trp Phe Arg
                565                 570                 575
Tyr Tyr Asp Leu Arg Asn Ala Thr Ala Ile Thr Thr Phe Gly Gln Met
            580                 585                 590
Ala Leu Gln Trp Ile Glu Arg Lys Val Asn Glu Tyr Leu Asn Glu Val
        595                 600                 605
Cys Gly Thr Glu Gly Glu Ala Phe Val Leu Tyr Gly Asp Thr Asp Ser
    610                 615                 620
Ile Tyr Val Ser Ala Asp Lys Ile Ile Asp Lys Val Gly Glu Ser Lys
625                 630                 635                 640
Phe Arg Asp Thr Asn His Trp Val Asp Phe Leu Asp Lys Phe Ala Arg
                645                 650                 655
Glu Arg Met Glu Pro Ala Ile Asp Arg Gly Phe Arg Glu Met Cys Glu
            660                 665                 670
Tyr Met Asn Asn Lys Gln His Leu Met Phe Met Asp Arg Glu Ala Ile
        675                 680                 685
Ala Gly Pro Pro Leu Gly Ser Lys Gly Ile Gly Gly Phe Trp Thr Gly
    690                 695                 700
Lys Lys Arg Tyr Ala Leu Asn Val Trp Asp Met Glu Gly Thr Arg Tyr
705                 710                 715                 720
Ala Glu Pro Lys Leu Lys Ile Met Gly Leu Glu Thr Gln Lys Ser Ser
                725                 730                 735
Thr Pro Lys Ala Val Gln Lys Ala Leu Lys Glu Cys Ile Arg Arg Met
            740                 745                 750
Leu Gln Glu Gly Glu Glu Ser Leu Gln Glu Tyr Phe Lys Glu Phe Glu
        755                 760                 765
```

```
Lys Glu Phe Arg Gln Leu Asn Tyr Ile Ser Ile Ala Ser Val Ser Ser
    770                 775                 780

Ala Asn Asn Ile Ala Lys Tyr Asp Val Gly Gly Phe Pro Gly Pro Lys
785                 790                 795                 800

Cys Pro Phe His Ile Arg Gly Ile Leu Thr Tyr Asn Arg Ala Ile Lys
                805                 810                 815

Gly Asn Ile Asp Ala Pro Gln Val Val Glu Gly Glu Lys Val Tyr Val
                820                 825                 830

Leu Pro Leu Arg Glu Gly Asn Pro Phe Gly Asp Lys Cys Ile Ala Trp
            835                 840                 845

Pro Ser Gly Thr Glu Ile Thr Asp Leu Ile Lys Asp Asp Val Leu His
            850                 855                 860

Trp Met Asp Tyr Thr Val Leu Leu Glu Lys Thr Phe Ile Lys Pro Leu
865                 870                 875                 880

Glu Gly Phe Thr Ser Ala Ala Lys Leu Asp Tyr Glu Lys Lys Ala Ser
                885                 890                 895

Leu Phe Asp Met Phe Asp Phe
            900

<210> SEQ ID NO 5
<211> LENGTH: 903
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Thr Arg Glu Val Glu
            20                  25                  30

Tyr Lys Pro Ser Leu Phe Ala His Cys Pro Glu Ser Gln Ala Thr Lys
            35                  40                  45

Tyr Phe Asp Ile Tyr Gly Lys Pro Cys Thr Arg Lys Leu Phe Ala Asn
    50                  55                  60

Met Arg Asp Ala Ser Gln Trp Ile Lys Arg Met Glu Asp Ile Gly Leu
65                  70                  75                  80

Glu Ala Leu Gly Met Asp Asp Phe Lys Leu Ala Tyr Leu Ser Asp Thr
                85                  90                  95

Tyr Asn Tyr Glu Ile Lys Tyr Asp His Thr Lys Ile Arg Val Ala Asn
                100                 105                 110

Phe Asp Ile Glu Val Thr Ser Pro Asp Gly Phe Pro Glu Pro Ser Gln
            115                 120                 125

Ala Lys His Pro Ile Asp Ala Ile Thr His Tyr Asp Ser Ile Asp Asp
            130                 135                 140

Arg Phe Tyr Val Phe Asp Leu Leu Asn Ser Pro Tyr Gly Asn Val Glu
145                 150                 155                 160

Glu Trp Ser Ile Glu Ile Ala Ala Lys Leu Gln Glu Gln Gly Gly Asp
                165                 170                 175

Glu Val Pro Ser Glu Ile Ile Asp Lys Ile Ile Tyr Met Pro Phe Asp
            180                 185                 190

Asn Glu Lys Glu Leu Leu Met Glu Tyr Leu Asn Phe Trp Gln Gln Lys
            195                 200                 205

Thr Pro Val Ile Leu Thr Gly Trp Asn Val Glu Ser Phe Ala Ile Pro
```

```
            210                 215                 220
Tyr Val Tyr Asn Arg Ile Lys Asn Ile Phe Gly Glu Ser Thr Ala Lys
225                 230                 235                 240

Arg Leu Ser Pro His Arg Lys Thr Arg Val Lys Val Ile Glu Asn Met
                245                 250                 255

Tyr Gly Ser Arg Glu Ile Ile Thr Leu Phe Gly Ile Ser Val Leu Asp
            260                 265                 270

Tyr Ile Asp Leu Tyr Lys Lys Phe Ser Phe Thr Asn Gln Pro Ser Tyr
        275                 280                 285

Ser Leu Asp Tyr Ile Ser Glu Phe Glu Leu Asn Val Gly Lys Leu Lys
        290                 295                 300

Tyr Asp Gly Pro Ile Ser Lys Leu Arg Glu Ser Asn His Gln Arg Tyr
305                 310                 315                 320

Ile Ser Tyr Asn Ile Ile Ala Val Tyr Arg Val Leu Gln Ile Asp Ala
                325                 330                 335

Lys Arg Gln Phe Ile Asn Leu Ser Leu Asp Met Gly Tyr Tyr Ala Lys
                340                 345                 350

Ile Gln Ile Gln Ser Val Phe Ser Pro Ile Lys Thr Trp Asp Ala Ile
                355                 360                 365

Ile Phe Asn Ser Leu Lys Glu Gln Asn Lys Val Ile Pro Gln Gly Arg
370                 375                 380

Ser His Pro Val Gln Pro Tyr Pro Gly Ala Phe Val Lys Glu Pro Ile
385                 390                 395                 400

Pro Asn Arg Tyr Lys Tyr Val Met Ser Phe Asp Leu Thr Ser Leu Tyr
                405                 410                 415

Pro Ser Ile Ile Arg Gln Val Asn Ile Ser Pro Glu Thr Ile Ala Gly
                420                 425                 430

Thr Phe Lys Val Ala Pro Leu His Asp Tyr Ile Asn Ala Val Ala Glu
                435                 440                 445

Arg Pro Ser Asp Val Tyr Ser Cys Ser Pro Asn Gly Met Met Tyr Tyr
450                 455                 460

Lys Asp Arg Asp Gly Val Val Pro Thr Glu Ile Thr Lys Val Phe Asn
465                 470                 475                 480

Gln Arg Lys Glu His Lys Gly Tyr Met Leu Ala Ala Gln Arg Asn Gly
                485                 490                 495

Glu Ile Ile Lys Glu Ala Leu His Asn Pro Asn Leu Ser Val Asp Glu
                500                 505                 510

Pro Leu Asp Val Asp Tyr Arg Phe Asp Phe Ser Asp Glu Ile Lys Glu
                515                 520                 525

Lys Ile Lys Lys Leu Ser Ala Lys Ser Leu Asn Glu Met Leu Phe Arg
530                 535                 540

Ala Gln Arg Thr Glu Val Ala Gly Met Thr Ala Gln Ile Leu Arg Lys
545                 550                 555                 560

Leu Leu Ile Asn Ser Leu Tyr Gly Ala Leu Gly Asn Val Trp Phe Arg
                565                 570                 575

Tyr Tyr Asp Leu Arg Asn Ala Thr Ala Ile Thr Thr Phe Gly Gln Met
                580                 585                 590

Ala Leu Gln Trp Ile Glu Arg Lys Val Asn Glu Tyr Leu Asn Glu Val
            595                 600                 605

Cys Gly Thr Glu Gly Glu Ala Phe Val Leu Tyr Gly Asp Thr Asp Ser
610                 615                 620

Ile Tyr Val Ser Ala Asp Lys Ile Ile Asp Lys Val Gly Glu Ser Lys
625                 630                 635                 640
```

-continued

```
Phe Arg Asp Thr Asn His Trp Val Asp Phe Leu Asp Lys Phe Ala Arg
                645                 650                 655

Glu Arg Met Glu Pro Ala Ile Asp Arg Gly Phe Arg Glu Met Cys Glu
            660                 665                 670

Tyr Met Asn Asn Lys Gln His Leu Met Phe Met Asp Arg Glu Ala Ile
        675                 680                 685

Ala Gly Pro Pro Leu Gly Ser Lys Gly Ile Gly Phe Trp Thr Gly
    690                 695                 700

Lys Lys Arg Tyr Ala Leu Asn Val Trp Asp Met Gly Thr Arg Tyr
705                 710                 715                 720

Ala Glu Pro Lys Leu Lys Ile Met Gly Leu Thr Gln Lys Ser Ser
                725                 730                 735

Thr Pro Lys Ala Val Gln Lys Ala Leu Lys Glu Cys Ile Arg Arg Met
            740                 745                 750

Leu Gln Glu Gly Glu Glu Ser Leu Gln Glu Tyr Phe Lys Glu Phe Glu
        755                 760                 765

Lys Glu Phe Arg Gln Leu Asn Tyr Ile Ser Ile Ala Ser Val Ser Ser
    770                 775                 780

Ala Asn Asn Ile Ala Lys Tyr Asp Val Gly Gly Phe Pro Gly Pro Lys
785                 790                 795                 800

Cys Pro Phe His Ile Arg Gly Ile Leu Thr Tyr Asn Arg Ala Ile Lys
                805                 810                 815

Gly Asn Ile Asp Ala Pro Gln Val Val Glu Gly Glu Lys Val Tyr Val
            820                 825                 830

Leu Pro Leu Arg Glu Gly Asn Pro Phe Gly Asp Lys Cys Ile Ala Trp
        835                 840                 845

Pro Ser Gly Thr Glu Ile Thr Asp Leu Ile Lys Asp Val Leu His
    850                 855                 860

Trp Met Asp Tyr Thr Val Leu Leu Glu Lys Thr Phe Ile Lys Pro Leu
865                 870                 875                 880

Glu Gly Phe Thr Ser Ala Ala Lys Leu Asp Tyr Glu Lys Lys Ala Ser
                885                 890                 895

Leu Phe Asp Met Phe Asp Phe
            900

<210> SEQ ID NO 6
<211> LENGTH: 903
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Arg Thr Arg Glu Val Glu
            20                  25                  30

Tyr Lys Pro Ser Leu Phe Ala His Cys Pro Glu Ser Gln Ala Thr Lys
        35                  40                  45

Tyr Phe Asp Ile Tyr Gly Lys Pro Cys Thr Arg Lys Leu Phe Ala Asn
    50                  55                  60

Met Arg Asp Ala Ser Gln Trp Ile Lys Arg Met Glu Asp Ile Gly Leu
65                  70                  75                  80

Glu Ala Leu Gly Met Asp Asp Phe Lys Leu Ala Tyr Leu Ser Asp Thr
```

-continued

```
                85                  90                  95
Tyr Asn Tyr Glu Ile Lys Tyr Asp His Thr Lys Ile Arg Val Ala Asn
            100                 105                 110

Phe Asp Ile Glu Val Thr Ser Pro Asp Gly Phe Pro Glu Pro Ser Gln
            115                 120                 125

Ala Lys His Pro Ile Asp Ala Ile Thr His Tyr Asp Ser Ile Asp Asp
            130                 135                 140

Arg Phe Tyr Val Phe Asp Leu Leu Asn Ser Pro Tyr Gly Asn Val Glu
145                 150                 155                 160

Glu Trp Ser Ile Glu Ile Ala Ala Lys Leu Gln Glu Gln Gly Gly Asp
                165                 170                 175

Glu Val Pro Ser Glu Ile Ile Asp Lys Ile Ile Tyr Met Pro Phe Asp
            180                 185                 190

Asn Glu Lys Glu Leu Leu Met Glu Tyr Leu Asn Phe Trp Gln Gln Lys
            195                 200                 205

Thr Pro Val Ile Leu Thr Gly Trp Asn Val Glu Ser Phe Ala Ile Pro
            210                 215                 220

Tyr Val Tyr Asn Arg Ile Lys Asn Ile Phe Gly Glu Ser Thr Ala Lys
225                 230                 235                 240

Arg Leu Ser Pro His Arg Lys Thr Arg Val Lys Val Ile Glu Asn Met
                245                 250                 255

Tyr Gly Ser Arg Glu Ile Ile Thr Leu Phe Gly Ile Ser Val Leu Asp
            260                 265                 270

Tyr Ile Asp Leu Tyr Lys Lys Phe Ser Phe Thr Asn Gln Pro Ser Tyr
            275                 280                 285

Ser Leu Asp Tyr Ile Ser Glu Phe Glu Leu Asn Val Gly Lys Leu Lys
            290                 295                 300

Tyr Asp Gly Pro Ile Ser Lys Leu Arg Glu Ser Asn His Gln Arg Tyr
305                 310                 315                 320

Ile Ser Tyr Asn Ile Ile Ala Val Tyr Arg Val Leu Gln Ile Asp Ala
                325                 330                 335

Lys Arg Gln Phe Ile Asn Leu Ser Leu Asp Met Gly Tyr Tyr Ala Lys
            340                 345                 350

Ile Gln Ile Gln Ser Val Phe Ser Pro Ile Lys Thr Trp Asp Ala Ile
            355                 360                 365

Ile Phe Asn Ser Leu Lys Glu Gln Asn Lys Val Ile Pro Gln Gly Arg
            370                 375                 380

Ser His Pro Val Gln Pro Tyr Pro Gly Ala Phe Val Lys Glu Pro Ile
385                 390                 395                 400

Pro Asn Arg Tyr Lys Tyr Val Met Ser Phe Asp Leu Thr Ser Leu Ala
                405                 410                 415

Pro Ser Ile Ile Arg Gln Val Asn Ile Ser Pro Glu Thr Ile Ala Gly
            420                 425                 430

Thr Phe Lys Val Ala Pro Leu His Asp Tyr Ile Asn Ala Val Ala Glu
            435                 440                 445

Arg Pro Ser Asp Val Tyr Ser Cys Ser Pro Asn Gly Met Met Tyr Tyr
            450                 455                 460

Lys Asp Arg Asp Gly Val Val Pro Thr Glu Ile Thr Lys Val Phe Asn
465                 470                 475                 480

Gln Arg Lys Glu His Lys Gly Tyr Met Leu Ala Ala Gln Arg Asn Gly
                485                 490                 495

Glu Ile Ile Lys Glu Ala Leu His Asn Pro Asn Leu Ser Val Asp Glu
            500                 505                 510
```

```
Pro Leu Asp Val Asp Tyr Arg Phe Asp Phe Ser Asp Glu Ile Lys Glu
            515                 520                 525

Lys Ile Lys Lys Leu Ser Ala Lys Ser Leu Asn Glu Met Leu Phe Arg
530                 535                 540

Ala Gln Arg Thr Glu Val Ala Gly Met Thr Ala Gln Ile Asn Arg Lys
545                 550                 555                 560

Leu Leu Ile Asn Ser Leu Tyr Gly Ala Leu Gly Asn Val Trp Phe Arg
            565                 570                 575

Tyr Tyr Asp Leu Arg Asn Ala Thr Ala Ile Thr Thr Phe Gly Gln Met
            580                 585                 590

Ala Leu Gln Trp Ile Glu Arg Lys Val Asn Glu Tyr Leu Asn Glu Val
            595                 600                 605

Cys Gly Thr Glu Gly Glu Ala Phe Val Leu Tyr Gly Asp Thr Asp Ser
            610                 615                 620

Ile Tyr Val Ser Ala Asp Lys Ile Ile Asp Lys Val Gly Glu Ser Lys
625                 630                 635                 640

Phe Arg Asp Thr Asn His Trp Val Asp Phe Leu Asp Lys Phe Ala Arg
            645                 650                 655

Glu Arg Met Glu Pro Ala Ile Asp Arg Gly Phe Arg Glu Met Cys Glu
            660                 665                 670

Tyr Met Asn Asn Lys Gln His Leu Met Phe Met Asp Arg Glu Ala Ile
            675                 680                 685

Ala Gly Pro Pro Leu Gly Ser Lys Gly Ile Gly Gly Phe Trp Thr Gly
            690                 695                 700

Lys Lys Arg Tyr Ala Leu Asn Val Trp Asp Met Glu Gly Thr Arg Tyr
705                 710                 715                 720

Ala Glu Pro Lys Leu Lys Ile Met Gly Leu Glu Thr Gln Lys Ser Ser
            725                 730                 735

Thr Pro Lys Ala Val Gln Lys Ala Leu Lys Glu Cys Ile Arg Arg Met
            740                 745                 750

Leu Gln Glu Gly Glu Glu Ser Leu Gln Glu Tyr Phe Lys Glu Phe Glu
            755                 760                 765

Lys Glu Phe Arg Gln Leu Asn Tyr Ile Ser Ile Ala Ser Val Ser Ser
            770                 775                 780

Ala Asn Asn Ile Ala Lys Tyr Asp Val Gly Gly Phe Pro Gly Pro Lys
785                 790                 795                 800

Cys Pro Phe His Ile Arg Gly Ile Leu Thr Tyr Asn Arg Ala Ile Lys
            805                 810                 815

Gly Asn Ile Asp Ala Pro Gln Val Val Glu Gly Glu Lys Val Tyr Val
            820                 825                 830

Leu Pro Leu Arg Glu Gly Asn Pro Phe Gly Asp Lys Cys Ile Ala Trp
            835                 840                 845

Pro Ser Gly Thr Glu Ile Thr Asp Leu Ile Lys Asp Asp Val Leu His
850                 855                 860

Trp Met Asp Tyr Thr Val Leu Leu Glu Lys Thr Phe Ile Lys Pro Leu
865                 870                 875                 880

Glu Gly Phe Thr Ser Ala Ala Lys Leu Asp Tyr Glu Lys Lys Ala Ser
            885                 890                 895

Leu Phe Asp Met Phe Asp Phe
            900

<210> SEQ ID NO 7
<211> LENGTH: 903
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Arg Thr Arg Glu Val Glu
            20                  25                  30

Tyr Lys Pro Ser Leu Phe Ala His Cys Pro Glu Ser Gln Ala Thr Lys
        35                  40                  45

Tyr Phe Asp Ile Tyr Gly Lys Pro Cys Thr Arg Lys Leu Phe Ala Asn
50                  55                  60

Met Arg Asp Ala Ser Gln Trp Ile Lys Arg Met Glu Asp Ile Gly Leu
65                  70                  75                  80

Glu Ala Leu Gly Met Asp Asp Phe Lys Leu Ala Tyr Leu Ser Asp Thr
                85                  90                  95

Tyr Asn Tyr Glu Ile Lys Tyr Asp His Thr Lys Ile Arg Val Ala Asn
            100                 105                 110

Phe Asp Ile Glu Val Thr Ser Pro Asp Gly Phe Pro Glu Pro Ser Gln
        115                 120                 125

Ala Lys His Pro Ile Asp Ala Ile Thr His Tyr Asp Ser Ile Asp Asp
130                 135                 140

Arg Phe Tyr Val Phe Asp Leu Leu Asn Ser Pro Tyr Gly Asn Val Glu
145                 150                 155                 160

Glu Trp Ser Ile Glu Ile Ala Ala Lys Leu Gln Glu Gln Gly Gly Asp
                165                 170                 175

Glu Val Pro Ser Glu Ile Ile Asp Lys Ile Ile Tyr Met Pro Phe Asp
            180                 185                 190

Asn Glu Lys Glu Leu Leu Met Glu Tyr Leu Asn Phe Trp Gln Gln Lys
        195                 200                 205

Thr Pro Val Ile Leu Thr Gly Trp Asn Val Glu Ser Phe Ala Ile Pro
210                 215                 220

Tyr Val Tyr Asn Arg Ile Lys Asn Ile Phe Gly Glu Ser Thr Ala Lys
225                 230                 235                 240

Arg Leu Ser Pro His Arg Lys Thr Arg Val Lys Val Ile Glu Asn Met
                245                 250                 255

Tyr Gly Ser Arg Glu Ile Ile Thr Leu Phe Gly Ile Ser Val Leu Asp
            260                 265                 270

Tyr Ile Asp Leu Tyr Lys Lys Phe Ser Phe Thr Asn Gln Pro Ser Tyr
        275                 280                 285

Ser Leu Asp Tyr Ile Ser Glu Phe Glu Leu Asn Val Gly Lys Leu Lys
290                 295                 300

Tyr Asp Gly Pro Ile Ser Lys Leu Arg Glu Ser Asn His Gln Arg Tyr
305                 310                 315                 320

Ile Ser Tyr Asn Ile Ile Ala Val Tyr Arg Val Leu Gln Ile Asp Ala
                325                 330                 335

Lys Arg Gln Phe Ile Asn Leu Ser Leu Asp Met Gly Tyr Tyr Ala Lys
            340                 345                 350

Ile Gln Ile Gln Ser Val Phe Ser Pro Ile Lys Thr Trp Asp Ala Ile
        355                 360                 365

Ile Phe Asn Ser Leu Lys Glu Gln Asn Lys Val Ile Pro Gln Gly Arg
370                 375                 380

```
Ser His Pro Val Gln Pro Tyr Pro Gly Ala Phe Val Lys Glu Pro Ile
385                 390                 395                 400

Pro Asn Arg Tyr Lys Tyr Val Met Ser Phe Asp Leu Thr Ser Leu Ala
            405                 410                 415

Pro Ser Ile Ile Arg Gln Val Asn Ile Ser Pro Glu Thr Ile Ala Gly
            420                 425                 430

Thr Phe Lys Val Ala Pro Leu His Asp Tyr Ile Asn Ala Val Ala Glu
        435                 440                 445

Arg Pro Ser Asp Val Tyr Ser Cys Ser Pro Asn Gly Met Met Tyr Tyr
    450                 455                 460

Lys Asp Arg Asp Gly Val Val Pro Thr Glu Ile Thr Lys Val Phe Asn
465                 470                 475                 480

Gln Arg Lys Glu His Lys Gly Tyr Met Leu Ala Ala Gln Arg Asn Gly
                485                 490                 495

Glu Ile Ile Lys Glu Ala Leu His Asn Pro Asn Leu Ser Val Asp Glu
            500                 505                 510

Pro Leu Asp Val Asp Tyr Arg Phe Asp Phe Ser Asp Glu Ile Lys Glu
        515                 520                 525

Lys Ile Lys Lys Leu Ser Ala Lys Ser Leu Asn Glu Met Leu Phe Arg
530                 535                 540

Ala Gln Arg Thr Glu Val Ala Gly Met Thr Ala Gln Ile Leu Arg Lys
545                 550                 555                 560

Leu Leu Ile Asn Ser Leu Tyr Gly Ala Leu Gly Asn Val Trp Phe Arg
                565                 570                 575

Tyr Tyr Asp Leu Arg Asn Ala Thr Ala Ile Thr Thr Phe Gly Gln Met
            580                 585                 590

Ala Leu Gln Trp Ile Glu Arg Lys Val Asn Glu Tyr Leu Asn Glu Val
        595                 600                 605

Cys Gly Thr Glu Gly Glu Ala Phe Val Leu Tyr Gly Asp Thr Asp Ser
    610                 615                 620

Ile Tyr Val Ser Ala Asp Lys Ile Ile Asp Lys Val Gly Glu Ser Lys
625                 630                 635                 640

Phe Arg Asp Thr Asn His Trp Val Asp Phe Leu Asp Lys Phe Ala Arg
                645                 650                 655

Glu Arg Met Glu Pro Ala Ile Asp Arg Gly Phe Arg Glu Met Cys Glu
            660                 665                 670

Tyr Met Asn Asn Lys Gln His Leu Met Phe Met Asp Arg Glu Ala Ile
        675                 680                 685

Ala Gly Pro Pro Leu Gly Ser Lys Gly Ile Gly Gly Phe Trp Thr Gly
    690                 695                 700

Lys Lys Arg Tyr Ala Leu Asn Val Trp Asp Met Glu Gly Thr Arg Tyr
705                 710                 715                 720

Ala Glu Pro Lys Leu Lys Ile Met Gly Leu Glu Thr Gln Lys Ser Ser
                725                 730                 735

Thr Pro Lys Ala Val Gln Lys Ala Leu Lys Glu Cys Ile Arg Arg Met
            740                 745                 750

Leu Gln Glu Gly Glu Glu Ser Leu Gln Glu Tyr Phe Lys Glu Phe Glu
        755                 760                 765

Lys Glu Phe Arg Gln Leu Asn Tyr Ile Ser Ile Ala Ser Val Ser Ser
    770                 775                 780

Ala Asn Asn Ile Ala Lys Tyr Asp Val Gly Gly Phe Pro Gly Pro Lys
785                 790                 795                 800
```

-continued

```
Cys Pro Phe His Ile Arg Gly Ile Leu Thr Tyr Asn Arg Ala Ile Lys
                805                 810                 815

Gly Asn Ile Asp Ala Pro Gln Val Val Glu Gly Glu Lys Val Tyr Val
            820                 825                 830

Leu Pro Leu Arg Glu Gly Asn Pro Phe Gly Asp Lys Cys Ile Ala Trp
            835                 840                 845

Pro Ser Gly Thr Glu Ile Thr Asp Leu Ile Lys Asp Val Leu His
850                 855                 860

Trp Met Asp Tyr Thr Val Leu Leu Glu Lys Thr Phe Ile Lys Pro Leu
865                 870                 875                 880

Glu Gly Phe Thr Ser Ala Ala Lys Leu Asp Tyr Glu Lys Lys Ala Ser
            885                 890                 895

Leu Phe Asp Met Phe Asp Phe
            900
```

<210> SEQ ID NO 8
<211> LENGTH: 903
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Arg Thr Arg Glu Val Glu
            20                  25                  30

Tyr Lys Pro Ser Leu Phe Ala His Cys Pro Glu Ser Gln Ala Thr Lys
        35                  40                  45

Tyr Phe Asp Ile Tyr Gly Lys Pro Cys Thr Arg Lys Leu Phe Ala Asn
    50                  55                  60

Met Arg Asp Ala Ser Gln Trp Ile Lys Arg Met Glu Asp Ile Gly Leu
65                  70                  75                  80

Glu Ala Leu Gly Met Asp Asp Phe Lys Leu Ala Tyr Leu Ser Asp Thr
                85                  90                  95

Tyr Asn Tyr Glu Ile Lys Tyr Asp His Thr Lys Ile Arg Val Ala Asn
            100                 105                 110

Phe Asp Ile Glu Val Thr Ser Pro Asp Gly Phe Pro Glu Pro Ser Gln
        115                 120                 125

Ala Lys His Pro Ile Asp Ala Ile Thr His Tyr Asp Ser Ile Asp Asp
    130                 135                 140

Arg Phe Tyr Val Phe Asp Leu Leu Asn Ser Pro Tyr Gly Asn Val Glu
145                 150                 155                 160

Glu Trp Ser Ile Glu Ile Ala Ala Lys Leu Gln Glu Gln Gly Gly Asp
                165                 170                 175

Glu Val Pro Ser Glu Ile Ile Asp Lys Ile Ile Tyr Met Pro Phe Asp
            180                 185                 190

Asn Glu Lys Glu Leu Leu Met Glu Tyr Leu Asn Phe Trp Gln Gln Lys
        195                 200                 205

Thr Pro Val Ile Leu Thr Gly Trp Asn Val Glu Ser Phe Ala Ile Pro
    210                 215                 220

Tyr Val Tyr Asn Arg Ile Lys Asn Ile Phe Gly Glu Ser Thr Ala Lys
225                 230                 235                 240

Arg Leu Ser Pro His Arg Lys Thr Arg Val Lys Val Ile Glu Asn Met
                245                 250                 255
```

-continued

```
Tyr Gly Ser Arg Glu Ile Ile Thr Leu Phe Gly Ile Ser Val Leu Asp
            260                 265                 270

Tyr Ile Asp Leu Tyr Lys Lys Phe Ser Phe Thr Asn Gln Pro Ser Tyr
        275                 280                 285

Ser Leu Asp Tyr Ile Ser Glu Phe Glu Leu Asn Val Gly Lys Leu Lys
290                 295                 300

Tyr Asp Gly Pro Ile Ser Lys Leu Arg Glu Ser Asn His Gln Arg Tyr
305                 310                 315                 320

Ile Ser Tyr Asn Ile Ile Ala Val Tyr Arg Val Leu Gln Ile Asp Ala
                325                 330                 335

Lys Arg Gln Phe Ile Asn Leu Ser Leu Asp Met Gly Tyr Tyr Ala Lys
                340                 345                 350

Ile Gln Ile Gln Ser Val Phe Ser Pro Ile Lys Thr Trp Asp Ala Ile
                355                 360                 365

Ile Phe Asn Ser Leu Lys Glu Gln Asn Lys Val Ile Pro Gln Gly Arg
            370                 375                 380

Ser His Pro Val Gln Pro Tyr Pro Gly Ala Phe Val Lys Glu Pro Ile
385                 390                 395                 400

Pro Asn Arg Tyr Lys Tyr Val Met Ser Phe Asp Leu Thr Ser Ser Ala
                405                 410                 415

Val Ser Ile Ile Arg Gln Val Asn Ile Ser Pro Glu Thr Ile Ala Gly
                420                 425                 430

Thr Phe Lys Val Ala Pro Leu His Asp Tyr Ile Asn Ala Val Ala Glu
            435                 440                 445

Arg Pro Ser Asp Val Tyr Ser Cys Ser Pro Asn Gly Met Met Tyr Tyr
            450                 455                 460

Lys Asp Arg Asp Gly Val Val Pro Thr Glu Ile Thr Lys Val Phe Asn
465                 470                 475                 480

Gln Arg Lys Glu His Lys Gly Tyr Met Leu Ala Ala Gln Arg Asn Gly
                485                 490                 495

Glu Ile Ile Lys Glu Ala Leu His Asn Pro Asn Leu Ser Val Asp Glu
            500                 505                 510

Pro Leu Asp Val Asp Tyr Arg Phe Asp Phe Ser Asp Glu Ile Lys Glu
            515                 520                 525

Lys Ile Lys Lys Leu Ser Ala Lys Ser Leu Asn Glu Met Leu Phe Arg
            530                 535                 540

Ala Gln Arg Thr Glu Val Ala Gly Met Thr Ala Gln Ile Leu Arg Lys
545                 550                 555                 560

Leu Leu Ile Asn Ser Leu Tyr Gly Ala Leu Gly Asn Val Trp Phe Arg
                565                 570                 575

Tyr Tyr Asp Leu Arg Asn Ala Thr Ala Ile Thr Thr Phe Gly Gln Met
            580                 585                 590

Ala Leu Gln Trp Ile Glu Arg Lys Val Asn Glu Tyr Leu Asn Glu Val
            595                 600                 605

Cys Gly Thr Glu Gly Glu Ala Phe Val Leu Tyr Gly Asp Thr Asp Ser
            610                 615                 620

Ile Tyr Val Ser Ala Asp Lys Ile Ile Asp Lys Val Gly Glu Ser Lys
625                 630                 635                 640

Phe Arg Asp Thr Asn His Trp Val Asp Phe Leu Asp Lys Phe Ala Arg
                645                 650                 655

Glu Arg Met Glu Pro Ala Ile Asp Arg Gly Phe Arg Glu Met Cys Glu
            660                 665                 670
```

```
Tyr Met Asn Asn Lys Gln His Leu Met Phe Met Asp Arg Glu Ala Ile
            675                 680                 685
Ala Gly Pro Pro Leu Gly Ser Lys Gly Ile Gly Gly Phe Trp Thr Gly
        690                 695                 700
Lys Lys Arg Tyr Ala Leu Asn Val Trp Asp Met Glu Gly Thr Arg Tyr
705                 710                 715                 720
Ala Glu Pro Lys Leu Lys Ile Met Gly Leu Glu Thr Gln Lys Ser Ser
                725                 730                 735
Thr Pro Lys Ala Val Gln Lys Ala Leu Lys Glu Cys Ile Arg Arg Met
            740                 745                 750
Leu Gln Glu Gly Glu Glu Ser Leu Gln Glu Tyr Phe Lys Glu Phe Glu
        755                 760                 765
Lys Glu Phe Arg Gln Leu Asn Tyr Ile Ser Ile Ala Ser Val Ser Ser
            770                 775                 780
Ala Asn Asn Ile Ala Lys Tyr Asp Val Gly Gly Phe Pro Gly Pro Lys
785                 790                 795                 800
Cys Pro Phe His Ile Arg Gly Ile Leu Thr Tyr Asn Arg Ala Ile Lys
                805                 810                 815
Gly Asn Ile Asp Ala Pro Gln Val Val Glu Gly Glu Lys Val Tyr Val
            820                 825                 830
Leu Pro Leu Arg Glu Gly Asn Pro Phe Gly Asp Lys Cys Ile Ala Trp
        835                 840                 845
Pro Ser Gly Thr Glu Ile Thr Asp Leu Ile Lys Asp Asp Val Leu His
    850                 855                 860
Trp Met Asp Tyr Thr Val Leu Leu Glu Lys Thr Phe Ile Lys Pro Leu
865                 870                 875                 880
Glu Gly Phe Thr Ser Ala Ala Lys Leu Asp Tyr Glu Lys Lys Ala Ser
                885                 890                 895
Leu Phe Asp Met Phe Asp Phe
            900

<210> SEQ ID NO 9
<211> LENGTH: 2709
<212> TYPE: DNA
<213> ORGANISM: Unknown
<220> FEATURE:
<223> OTHER INFORMATION: Description of Unknown: Enterobacteria phage
      RB69 polypeptide
<220> FEATURE:
<221> NAME/KEY: CDS
<222> LOCATION: (1)..(2709)

<400> SEQUENCE: 9 atg aaa gaa ttt tac tta acg gtt gaa cag att ggt gat tca att ttt    48
Met Lys Glu Phe Tyr Leu Thr Val Glu Gln Ile Gly Asp Ser Ile Phe
1               5                   10                  15 gaa cgt tac atc gat tct aat ggc cgt gaa cgt act cgt gaa gta gaa    96
Glu Arg Tyr Ile Asp Ser Asn Gly Arg Glu Arg Thr Arg Glu Val Glu
                20                  25                  30 tat aaa cca tca ctg ttt gct cat tgt cca gaa agt cag gct acg aaa   144
Tyr Lys Pro Ser Leu Phe Ala His Cys Pro Glu Ser Gln Ala Thr Lys
            35                  40                  45 tat ttc gat atc tac ggt aaa ccg tgt act cgt aag ttg ttc gct aat   192
Tyr Phe Asp Ile Tyr Gly Lys Pro Cys Thr Arg Lys Leu Phe Ala Asn
        50                  55                  60 atg cgt gat gcc tcc caa tgg att aaa cgc atg gaa gat atc gga ctt   240
Met Arg Asp Ala Ser Gln Trp Ile Lys Arg Met Glu Asp Ile Gly Leu
65                  70                  75                  80
```

```
gaa gca ctt ggc atg gac gat ttc aaa ttg gcg tat ttg tct gac act    288
Glu Ala Leu Gly Met Asp Asp Phe Lys Leu Ala Tyr Leu Ser Asp Thr
             85                  90                  95 tat aac tat gaa atc aaa tac gac cat aca aaa att cgt gtg gct aac    336
Tyr Asn Tyr Glu Ile Lys Tyr Asp His Thr Lys Ile Arg Val Ala Asn
            100                 105                 110 ttc gac atc gaa gta aca tct ccg gat ggg ttc cct gag ccg tca caa    384
Phe Asp Ile Glu Val Thr Ser Pro Asp Gly Phe Pro Glu Pro Ser Gln
        115                 120                 125 gca aaa cat ccg att gat gct atc acc cat tat gac tca att gac gac    432
Ala Lys His Pro Ile Asp Ala Ile Thr His Tyr Asp Ser Ile Asp Asp
    130                 135                 140 agg ttc tac gta ttt gat cta ttg aat tct cca tat ggt aat gta gaa    480
Arg Phe Tyr Val Phe Asp Leu Leu Asn Ser Pro Tyr Gly Asn Val Glu
145                 150                 155                 160 gaa tgg tct att gaa atc gct gct aag ctt caa gaa caa ggt ggt gat    528
Glu Trp Ser Ile Glu Ile Ala Ala Lys Leu Gln Glu Gln Gly Gly Asp
                165                 170                 175 gaa gtt cca tct gaa att att gat aaa atc att tat atg ccg ttc gat    576
Glu Val Pro Ser Glu Ile Ile Asp Lys Ile Ile Tyr Met Pro Phe Asp
            180                 185                 190 aac gaa aaa gaa ttg ttg atg gaa tat ctc aac ttc tgg caa cag aaa    624
Asn Glu Lys Glu Leu Leu Met Glu Tyr Leu Asn Phe Trp Gln Gln Lys
        195                 200                 205 act cct gtc att ttg act gga tgg aac gtt gag tca ttt gat att ccg    672
Thr Pro Val Ile Leu Thr Gly Trp Asn Val Glu Ser Phe Asp Ile Pro
    210                 215                 220 tac gtg tat aac cga atc aag aat att ttt ggc gaa tca act gcg aaa    720
Tyr Val Tyr Asn Arg Ile Lys Asn Ile Phe Gly Glu Ser Thr Ala Lys
225                 230                 235                 240 cgt tta tca cca cat cgt aaa act cgt gtt aaa gtt atc gaa aac atg    768
Arg Leu Ser Pro His Arg Lys Thr Arg Val Lys Val Ile Glu Asn Met
                245                 250                 255 tat ggt tct cgt gaa atc att aca ttg ttc ggt atc tct gtt ctt gat    816
Tyr Gly Ser Arg Glu Ile Ile Thr Leu Phe Gly Ile Ser Val Leu Asp
            260                 265                 270 tac att gac ctt tac aaa aaa ttc tct ttt acc aat caa ccg tcg tat    864
Tyr Ile Asp Leu Tyr Lys Lys Phe Ser Phe Thr Asn Gln Pro Ser Tyr
        275                 280                 285 tct ctg gat tac att tca gaa ttt gaa ttg aac gtt ggt aaa ctg aaa    912
Ser Leu Asp Tyr Ile Ser Glu Phe Glu Leu Asn Val Gly Lys Leu Lys
    290                 295                 300 tat gac ggc cct att tct aag ctt cgt gaa agc aat cac caa cga tat    960
Tyr Asp Gly Pro Ile Ser Lys Leu Arg Glu Ser Asn His Gln Arg Tyr
305                 310                 315                 320 att tct tat aac att atc gac gtg tat cgt gta ttg caa att gat gct   1008
Ile Ser Tyr Asn Ile Ile Asp Val Tyr Arg Val Leu Gln Ile Asp Ala
                325                 330                 335 aag cgt cag ttc atc aac ttg agt ttg gac atg ggt tat tat gct aag   1056
Lys Arg Gln Phe Ile Asn Leu Ser Leu Asp Met Gly Tyr Tyr Ala Lys
            340                 345                 350 ata cag att caa tct gtg ttt agc cca att aaa aca tgg gat gct att   1104
Ile Gln Ile Gln Ser Val Phe Ser Pro Ile Lys Thr Trp Asp Ala Ile
        355                 360                 365 att ttt aat agc ctt aaa gag cag aac aag gtg att cca caa ggt cgt   1152
Ile Phe Asn Ser Leu Lys Glu Gln Asn Lys Val Ile Pro Gln Gly Arg
    370                 375                 380 tct cac ccg gtt caa cct tat ccc ggc gct ttt gtt aag gaa cct att   1200
Ser His Pro Val Gln Pro Tyr Pro Gly Ala Phe Val Lys Glu Pro Ile
385                 390                 395                 400
```

```
cca aat cga tac aaa tat gta atg agt ttc gac ctt aca tct cta tat    1248
Pro Asn Arg Tyr Lys Tyr Val Met Ser Phe Asp Leu Thr Ser Leu Tyr
            405                 410                 415 cca agt att att cgc caa gtg aat att agc cca gaa aca ata gca gga    1296
Pro Ser Ile Ile Arg Gln Val Asn Ile Ser Pro Glu Thr Ile Ala Gly
        420                 425                 430 acg ttt aaa gta gct cca ttg cat gat tat att aac gct gtt gct gaa    1344
Thr Phe Lys Val Ala Pro Leu His Asp Tyr Ile Asn Ala Val Ala Glu
    435                 440                 445 cgt cct tct gat gtg tac agt tgt tct cct aac ggc atg atg tat tat    1392
Arg Pro Ser Asp Val Tyr Ser Cys Ser Pro Asn Gly Met Met Tyr Tyr
450                 455                 460 aaa gac cgt gat ggt gta gtt cca act gaa atc act aag gtc ttt aat    1440
Lys Asp Arg Asp Gly Val Val Pro Thr Glu Ile Thr Lys Val Phe Asn
465                 470                 475                 480 caa cgt aaa gaa cat aaa ggt tac atg ctt gca gct caa cgt aat ggt    1488
Gln Arg Lys Glu His Lys Gly Tyr Met Leu Ala Ala Gln Arg Asn Gly
                485                 490                 495 gaa ata att aaa gag gca ttg cat aat cct aat ctt tct gtt gac gaa    1536
Glu Ile Ile Lys Glu Ala Leu His Asn Pro Asn Leu Ser Val Asp Glu
            500                 505                 510 cca tta gat gtt gat tat cgt ttc gac ttc agc gat gag att aaa gaa    1584
Pro Leu Asp Val Asp Tyr Arg Phe Asp Phe Ser Asp Glu Ile Lys Glu
        515                 520                 525 aag att aaa aag ttg tct gct aaa tct ctt aat gaa atg ttg ttt aga    1632
Lys Ile Lys Lys Leu Ser Ala Lys Ser Leu Asn Glu Met Leu Phe Arg
    530                 535                 540 gct caa cgt act gaa gtt gca ggt atg act gca caa att aac cgt aaa    1680
Ala Gln Arg Thr Glu Val Ala Gly Met Thr Ala Gln Ile Asn Arg Lys
545                 550                 555                 560 ttg ctt atc aac tca ctt tat ggt gca ctt ggc aac gtt tgg ttc cgt    1728
Leu Leu Ile Asn Ser Leu Tyr Gly Ala Leu Gly Asn Val Trp Phe Arg
                565                 570                 575 tat tat gat ttg cgt aat gct act gca atc aca aca ttc ggg caa atg    1776
Tyr Tyr Asp Leu Arg Asn Ala Thr Ala Ile Thr Thr Phe Gly Gln Met
            580                 585                 590 gct tta cag tgg att gaa cgt aaa gtt aat gaa tat ctg aat gaa gtt    1824
Ala Leu Gln Trp Ile Glu Arg Lys Val Asn Glu Tyr Leu Asn Glu Val
        595                 600                 605 tgt ggt aca gaa ggt gaa gct ttc gtt ctt tat ggt gat aca gac tct    1872
Cys Gly Thr Glu Gly Glu Ala Phe Val Leu Tyr Gly Asp Thr Asp Ser
    610                 615                 620 att tac gta tct gct gat aaa att atc gat aag gtt ggt gaa tct aaa    1920
Ile Tyr Val Ser Ala Asp Lys Ile Ile Asp Lys Val Gly Glu Ser Lys
625                 630                 635                 640 ttc cgt gat acc aac cat tgg gta gac ttc tta gat aag ttt gca cgt    1968
Phe Arg Asp Thr Asn His Trp Val Asp Phe Leu Asp Lys Phe Ala Arg
                645                 650                 655 gaa cgt atg gaa cca gct att gat aga ggt ttc cgt gaa atg tgt gaa    2016
Glu Arg Met Glu Pro Ala Ile Asp Arg Gly Phe Arg Glu Met Cys Glu
            660                 665                 670 tac atg aac aat aaa caa cac tta atg ttc atg gac cga gaa gct atc    2064
Tyr Met Asn Asn Lys Gln His Leu Met Phe Met Asp Arg Glu Ala Ile
        675                 680                 685 gct ggg cct ccg ctt ggt tct aaa ggt att ggc gga ttt tgg act ggt    2112
Ala Gly Pro Pro Leu Gly Ser Lys Gly Ile Gly Gly Phe Trp Thr Gly
    690                 695                 700 aag aaa cgt tat gca tta aac gtg tgg gat atg gaa ggt act cgt tac    2160
Lys Lys Arg Tyr Ala Leu Asn Val Trp Asp Met Glu Gly Thr Arg Tyr
```

```
                705                 710                 715                 720
gct gag cct aaa ctc aaa atc atg ggt cta gag act cag aaa tct tcg        2208
Ala Glu Pro Lys Leu Lys Ile Met Gly Leu Glu Thr Gln Lys Ser Ser
                    725                 730                 735 act cct aaa gca gta cag aaa gct ctt aaa gaa tgt att cgt cgt atg        2256
Thr Pro Lys Ala Val Gln Lys Ala Leu Lys Glu Cys Ile Arg Arg Met
                740                 745                 750 ctt caa gaa ggt gaa gaa tca tta caa gaa tat ttt aaa gag ttt gaa        2304
Leu Gln Glu Gly Glu Glu Ser Leu Gln Glu Tyr Phe Lys Glu Phe Glu
            755                 760                 765 aaa gaa ttc cgt caa ttg aat tat att agc atc gcg tcg gta tct tct        2352
Lys Glu Phe Arg Gln Leu Asn Tyr Ile Ser Ile Ala Ser Val Ser Ser
        770                 775                 780 gcg aat aac att gct aaa tat gac gta ggt gga ttc cct ggt ccc aaa        2400
Ala Asn Asn Ile Ala Lys Tyr Asp Val Gly Gly Phe Pro Gly Pro Lys
785                 790                 795                 800 tgc ccg ttc cat att cgt gga att ctg aca tat aac cga gct atc aaa        2448
Cys Pro Phe His Ile Arg Gly Ile Leu Thr Tyr Asn Arg Ala Ile Lys
                    805                 810                 815 ggt aat att gat gca cca caa gtt gta gaa ggt gaa aaa gta tat gtt        2496
Gly Asn Ile Asp Ala Pro Gln Val Val Glu Gly Glu Lys Val Tyr Val
                820                 825                 830 ctg cct tta cgt gaa gga aac cca ttc ggt gat aaa tgt atc gca tgg        2544
Leu Pro Leu Arg Glu Gly Asn Pro Phe Gly Asp Lys Cys Ile Ala Trp
            835                 840                 845 cct tct ggt act gaa atc aca gat tta att aaa gac gac gta ctt cat        2592
Pro Ser Gly Thr Glu Ile Thr Asp Leu Ile Lys Asp Asp Val Leu His
        850                 855                 860 tgg atg gac tac act gtt ctc ctt gag aag aca ttt att aaa cca ctt        2640
Trp Met Asp Tyr Thr Val Leu Leu Glu Lys Thr Phe Ile Lys Pro Leu
865                 870                 875                 880 gaa gga ttc aca tca gca gcg aaa ctc gat tac gag aag aaa gca tct        2688
Glu Gly Phe Thr Ser Ala Ala Lys Leu Asp Tyr Glu Lys Lys Ala Ser
                    885                 890                 895 ctg ttc gat atg ttc gat ttt                                            2709
Leu Phe Asp Met Phe Asp Phe
                900

<210> SEQ ID NO 10
<211> LENGTH: 2709
<212> TYPE: DNA
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: CDS
<222> LOCATION: (1)..(2709)

<400> SEQUENCE: 10 atg aaa gaa ttt tac tta acg gtt gaa cag att ggt gat tca att ttt         48
Met Lys Glu Phe Tyr Leu Thr Val Glu Gln Ile Gly Asp Ser Ile Phe
1               5                   10                  15 gaa cgt tac atc gat tct aat ggc cgt gaa cgt act cgt gaa gta gaa         96
Glu Arg Tyr Ile Asp Ser Asn Gly Arg Glu Arg Thr Arg Glu Val Glu
                20                  25                  30 tat aaa cca tca ctg ttt gct cat tgt cca gaa agt cag gct acg aaa        144
Tyr Lys Pro Ser Leu Phe Ala His Cys Pro Glu Ser Gln Ala Thr Lys
            35                  40                  45 tat ttc gat atc tac ggt aaa ccg tgt act cgt aag ttg ttc gct aat        192
Tyr Phe Asp Ile Tyr Gly Lys Pro Cys Thr Arg Lys Leu Phe Ala Asn
        50                  55                  60
```

```
atg cgt gat gcc tcc caa tgg att aaa cgc atg gaa gat atc gga ctt    240
Met Arg Asp Ala Ser Gln Trp Ile Lys Arg Met Glu Asp Ile Gly Leu
 65              70                  75                  80 gaa gca ctt ggc atg gac gat ttc aaa ttg gcg tat ttg tct gac act    288
Glu Ala Leu Gly Met Asp Asp Phe Lys Leu Ala Tyr Leu Ser Asp Thr
                 85                  90                  95 tat aac tat gaa atc aaa tac gac cat aca aaa att cgt gtg gct aac    336
Tyr Asn Tyr Glu Ile Lys Tyr Asp His Thr Lys Ile Arg Val Ala Asn
            100                 105                 110 ttc gac atc gaa gta aca tct ccg gat ggg ttc cct gag ccg tca caa    384
Phe Asp Ile Glu Val Thr Ser Pro Asp Gly Phe Pro Glu Pro Ser Gln
        115                 120                 125 gca aaa cat ccg att gat gct atc acc cat tat gac tca att gac gac    432
Ala Lys His Pro Ile Asp Ala Ile Thr His Tyr Asp Ser Ile Asp Asp
    130                 135                 140 agg ttc tac gta ttt gat cta ttg aat tct cca tat ggt aat gta gaa    480
Arg Phe Tyr Val Phe Asp Leu Leu Asn Ser Pro Tyr Gly Asn Val Glu
145                 150                 155                 160 gaa tgg tct att gaa atc gct gct aag ctt caa gaa caa ggt ggt gat    528
Glu Trp Ser Ile Glu Ile Ala Ala Lys Leu Gln Glu Gln Gly Gly Asp
                165                 170                 175 gaa gtt cca tct gaa att att gat aaa atc att tat atg ccg ttc gat    576
Glu Val Pro Ser Glu Ile Ile Asp Lys Ile Ile Tyr Met Pro Phe Asp
            180                 185                 190 aac gaa aaa gaa ttg ttg atg gaa tat ctc aac ttc tgg caa cag aaa    624
Asn Glu Lys Glu Leu Leu Met Glu Tyr Leu Asn Phe Trp Gln Gln Lys
        195                 200                 205 act cct gtc att ttg act gga tgg aac gtt gag tca ttt gct att ccg    672
Thr Pro Val Ile Leu Thr Gly Trp Asn Val Glu Ser Phe Ala Ile Pro
    210                 215                 220 tac gtg tat aac cga atc aag aat att ttt ggc gaa tca act gcg aaa    720
Tyr Val Tyr Asn Arg Ile Lys Asn Ile Phe Gly Glu Ser Thr Ala Lys
225                 230                 235                 240 cgt tta tca cca cat cgt aaa act cgt gtt aaa gtt atc gaa aac atg    768
Arg Leu Ser Pro His Arg Lys Thr Arg Val Lys Val Ile Glu Asn Met
                245                 250                 255 tat ggt tct cgt gaa atc att aca ttg ttc ggt atc tct gtt ctt gat    816
Tyr Gly Ser Arg Glu Ile Ile Thr Leu Phe Gly Ile Ser Val Leu Asp
            260                 265                 270 tac att gac ctt tac aaa aaa ttc tct ttt acc aat caa ccg tcg tat    864
Tyr Ile Asp Leu Tyr Lys Lys Phe Ser Phe Thr Asn Gln Pro Ser Tyr
        275                 280                 285 tct ctg gat tac att tca gaa ttt gaa ttg aac gtt ggt aaa ctg aaa    912
Ser Leu Asp Tyr Ile Ser Glu Phe Glu Leu Asn Val Gly Lys Leu Lys
    290                 295                 300 tat gac ggc cct att tct aag ctt cgt gaa agc aat cac caa cga tat    960
Tyr Asp Gly Pro Ile Ser Lys Leu Arg Glu Ser Asn His Gln Arg Tyr
305                 310                 315                 320 att tct tat aac att atc gct gtg tat cgt gta ttg caa att gat gct   1008
Ile Ser Tyr Asn Ile Ile Ala Val Tyr Arg Val Leu Gln Ile Asp Ala
                325                 330                 335 aag cgt cag ttc atc aac ttg agt ttg gac atg ggt tat tat gct aag   1056
Lys Arg Gln Phe Ile Asn Leu Ser Leu Asp Met Gly Tyr Tyr Ala Lys
            340                 345                 350 ata cag att caa tct gtg ttt agc cca att aaa aca tgg gat gct att   1104
Ile Gln Ile Gln Ser Val Phe Ser Pro Ile Lys Thr Trp Asp Ala Ile
        355                 360                 365 att ttt aat agc ctt aaa gag cag aac aag gtg att cca caa ggt cgt   1152
Ile Phe Asn Ser Leu Lys Glu Gln Asn Lys Val Ile Pro Gln Gly Arg
```

```
                370                 375                 380
tct cac ccg gtt caa cct tat ccc ggc gct ttt gtt aag gaa cct att    1200
Ser His Pro Val Gln Pro Tyr Pro Gly Ala Phe Val Lys Glu Pro Ile
385                 390                 395                 400 cca aat cga tac aaa tat gta atg agt ttc gac ctt aca tct tca gct    1248
Pro Asn Arg Tyr Lys Tyr Val Met Ser Phe Asp Leu Thr Ser Ser Ala
            405                 410                 415 gta agt att att cgc caa gtg aat att agc cca gaa aca ata gca gga    1296
Val Ser Ile Ile Arg Gln Val Asn Ile Ser Pro Glu Thr Ile Ala Gly
        420                 425                 430 acg ttt aaa gta gct cca ttg cat gat tat att aac gct gtt gct gaa    1344
Thr Phe Lys Val Ala Pro Leu His Asp Tyr Ile Asn Ala Val Ala Glu
    435                 440                 445 cgt cct tct gat gtg tac agt tgt tct cct aac ggc atg atg tat tat    1392
Arg Pro Ser Asp Val Tyr Ser Cys Ser Pro Asn Gly Met Met Tyr Tyr
450                 455                 460 aaa gac cgt gat ggt gta gtt cca act gaa atc act aag gtc ttt aat    1440
Lys Asp Arg Asp Gly Val Val Pro Thr Glu Ile Thr Lys Val Phe Asn
465                 470                 475                 480 caa cgt aaa gaa cat aaa ggt tac atg ctt gca gct caa cgt aat ggt    1488
Gln Arg Lys Glu His Lys Gly Tyr Met Leu Ala Ala Gln Arg Asn Gly
            485                 490                 495 gaa ata att aaa gag gca ttg cat aat cct aat ctt tct gtt gac gaa    1536
Glu Ile Ile Lys Glu Ala Leu His Asn Pro Asn Leu Ser Val Asp Glu
        500                 505                 510 cca tta gat gtt gat tat cgt ttc gac ttc agc gat gag att aaa gaa    1584
Pro Leu Asp Val Asp Tyr Arg Phe Asp Phe Ser Asp Glu Ile Lys Glu
    515                 520                 525 aag att aaa aag ttg tct gct aaa tct ctt aat gaa atg ttg ttt aga    1632
Lys Ile Lys Lys Leu Ser Ala Lys Ser Leu Asn Glu Met Leu Phe Arg
530                 535                 540 gct caa cgt act gaa gtt gca ggt atg act gca caa att aac cgt aaa    1680
Ala Gln Arg Thr Glu Val Ala Gly Met Thr Ala Gln Ile Asn Arg Lys
545                 550                 555                 560 ttg ctt atc aac tca ctt tat ggt gca ctt ggc aac gtt tgg ttc cgt    1728
Leu Leu Ile Asn Ser Leu Tyr Gly Ala Leu Gly Asn Val Trp Phe Arg
            565                 570                 575 tat tat gat ttg cgt aat gct act gca atc aca aca ttc ggg caa atg    1776
Tyr Tyr Asp Leu Arg Asn Ala Thr Ala Ile Thr Thr Phe Gly Gln Met
        580                 585                 590 gct tta cag tgg att gaa cgt aaa gtt aat gaa tat ctg aat gaa gtt    1824
Ala Leu Gln Trp Ile Glu Arg Lys Val Asn Glu Tyr Leu Asn Glu Val
    595                 600                 605 tgt ggt aca gaa ggt gaa gct ttc gtt ctt tat ggt gat aca gac tct    1872
Cys Gly Thr Glu Gly Glu Ala Phe Val Leu Tyr Gly Asp Thr Asp Ser
610                 615                 620 att tac gta tct gct gat aaa att atc gat aag gtt ggt gaa tct aaa    1920
Ile Tyr Val Ser Ala Asp Lys Ile Ile Asp Lys Val Gly Glu Ser Lys
625                 630                 635                 640 ttc cgt gat acc aac cat tgg gta gac ttc tta gat aag ttt gca cgt    1968
Phe Arg Asp Thr Asn His Trp Val Asp Phe Leu Asp Lys Phe Ala Arg
            645                 650                 655 gaa cgt atg gaa cca gct att gat aga ggt ttc cgt gaa atg tgt gaa    2016
Glu Arg Met Glu Pro Ala Ile Asp Arg Gly Phe Arg Glu Met Cys Glu
        660                 665                 670 tac atg aac aat aaa caa cac tta atg ttc atg gac cga gaa gct atc    2064
Tyr Met Asn Asn Lys Gln His Leu Met Phe Met Asp Arg Glu Ala Ile
    675                 680                 685 gct ggg cct ccg ctt ggt tct aaa ggt att ggc gga ttt tgg act ggt    2112
```

|  |  |  |  |  |  |  |  |  |  |  |  |  |
|---|---|---|---|---|---|---|---|---|---|---|---|---|
| Ala | Gly | Pro | Pro | Leu | Gly | Ser | Lys | Gly | Ile | Gly | Phe | Trp | Thr | Gly |
|  | 690 |  |  |  | 695 |  |  |  | 700 |  |  |  |  |  |

```
aag aaa cgt tat gca tta aac gtg tgg gat atg gaa ggt act cgt tac    2160
Lys Lys Arg Tyr Ala Leu Asn Val Trp Asp Met Glu Gly Thr Arg Tyr
705             710                 715                 720 gct gag cct aaa ctc aaa atc atg ggt cta gag act cag aaa tct tcg    2208
Ala Glu Pro Lys Leu Lys Ile Met Gly Leu Glu Thr Gln Lys Ser Ser
                725                 730                 735 act cct aaa gca gta cag aaa gct ctt aaa gaa tgt att cgt cgt atg    2256
Thr Pro Lys Ala Val Gln Lys Ala Leu Lys Glu Cys Ile Arg Arg Met
            740                 745                 750 ctt caa gaa ggt gaa gaa tca tta caa gaa tat ttt aaa gag ttt gaa    2304
Leu Gln Glu Gly Glu Glu Ser Leu Gln Glu Tyr Phe Lys Glu Phe Glu
        755                 760                 765 aaa gaa ttc cgt caa ttg aat tat att agc atc gcg tcg gta tct tct    2352
Lys Glu Phe Arg Gln Leu Asn Tyr Ile Ser Ile Ala Ser Val Ser Ser
    770                 775                 780 gcg aat aac att gct aaa tat gac gta ggt gga ttc cct ggt ccc aaa    2400
Ala Asn Asn Ile Ala Lys Tyr Asp Val Gly Gly Phe Pro Gly Pro Lys
785                 790                 795                 800 tgc ccg ttc cat att cgt gga att ctg aca tat aac cga gct atc aaa    2448
Cys Pro Phe His Ile Arg Gly Ile Leu Thr Tyr Asn Arg Ala Ile Lys
                805                 810                 815 ggt aat att gat gca cca caa gtt gta gaa ggt gaa aaa gta tat gtt    2496
Gly Asn Ile Asp Ala Pro Gln Val Val Glu Gly Glu Lys Val Tyr Val
            820                 825                 830 ctg cct tta cgt gaa gga aac cca ttc ggt gat aaa tgt atc gca tgg    2544
Leu Pro Leu Arg Glu Gly Asn Pro Phe Gly Asp Lys Cys Ile Ala Trp
        835                 840                 845 cct tct ggt act gaa atc aca gat tta att aaa gac gac gta ctt cat    2592
Pro Ser Gly Thr Glu Ile Thr Asp Leu Ile Lys Asp Asp Val Leu His
    850                 855                 860 tgg atg gac tac act gtt ctc ctt gag aag aca ttt att aaa cca ctt    2640
Trp Met Asp Tyr Thr Val Leu Leu Glu Lys Thr Phe Ile Lys Pro Leu
865                 870                 875                 880 gaa gga ttc aca tca gca gcg aaa ctc gat tac gag aag aaa gca tct    2688
Glu Gly Phe Thr Ser Ala Ala Lys Leu Asp Tyr Glu Lys Lys Ala Ser
                885                 890                 895 ctg ttc gat atg ttc gat ttt                                         2709
Leu Phe Asp Met Phe Asp Phe
                900

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cagtctcggg atcttgtgcc atttttggc acaagatccc                            40

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
```
cgttccacgc ccgctccttt gcaac                                        25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cgaacctcgc ccgctccttt gcaac                                        25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cgttaaccgc ccgctccttt gcaac                                        25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cgttaagcgc ccgctccttt gcaac                                        25

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gttgcaaagg agcgggcg                                                18

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cagtccagga gttggttgga cggctgcgag gc                                32

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cagtaatgga gttggttgga cggctgcgag gc                                32

```
<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cagtaacgga gttggttgga cggctgcgag gc                                     32

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cagtaaggga gttggttgga cggctgcgag gc                                     32

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcctcgcagc cgtccaacca actcc                                             25

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcctcgcagc cgtccaacca actcc                                             25

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 23

His His His His His His
1               5
```